(12) United States Patent
Stitt et al.

(10) Patent No.: US 7,632,503 B2
(45) Date of Patent: Dec. 15, 2009

(54) METHOD OF TREATING A MUSCLE-RELATED CONDITION WITH MODIFIED IGF1 POLYPEPTIDES

(75) Inventors: Trevor Stitt, Ridgewood, NJ (US); Esther Latres, New York, NY (US); David J. Glass, Cortlandt Manor, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 12/070,213

(22) Filed: Feb. 14, 2008

(65) Prior Publication Data

US 2008/0199479 A1 Aug. 21, 2008

Related U.S. Application Data

(62) Division of application No. 10/954,468, filed on Sep. 30, 2004, now Pat. No. 7,355,018.

(60) Provisional application No. 60/507,168, filed on Sep. 30, 2003, provisional application No. 60/516,806, filed on Nov. 3, 2003, provisional application No. 60/573,525, filed on May 21, 2004, provisional application No. 60/534,819, filed on Jan. 7, 2004, provisional application No. 60/584,956, filed on Jul. 2, 2004, provisional application No. 60/529,826, filed on Dec. 16, 2003, provisional application No. 60/534,654, filed on Jan. 7, 2004, provisional application No. 60/581,833, filed on Jun. 22, 2004, provisional application No. 60/554,640, filed on Mar. 19, 2004.

(51) Int. Cl.
*A61K 39/395* (2006.01)
*A61K 38/00* (2006.01)

(52) U.S. Cl. ..................... 424/158.1; 514/12
(58) Field of Classification Search ............... None
See application file for complete search history.

(56) References Cited

U.S. PATENT DOCUMENTS

| 5,164,370 | A | 11/1992 | Ballard et al. |
|---|---|---|---|
| 6,329,501 | B1 | 12/2001 | Smith |
| 6,509,443 | B1 | 1/2003 | Dubaquie et al. |
| 2002/0137023 | A1 | 9/2002 | Smith et al. |
| 2002/0164702 | A1 | 11/2002 | Valenzuela et al. |

FOREIGN PATENT DOCUMENTS

| WO | WO 90/15142 A | 12/1990 |
|---|---|---|
| WO | WO 96/08274 A2 | 3/1996 |
| WO | WO 97/21811 A | 6/1997 |
| WO | WO 98/50432 A1 | 11/1998 |
| WO | WO 98/53804 A1 | 12/1998 |
| WO | WO 99/10494 A | 3/1999 |
| WO | WO 03/070195 A | 8/2003 |

OTHER PUBLICATIONS

Glass, D. et al., ( 1997), Current Opinion Neurpbiology, vol. 7, No. 3, pp. 379-384.
Glass, D. et al., (1996),Agrin acts via a musk recptor complex, Cell, May 17, vol. 85, No. 4 pp. 513-523.
Liyanage, Y. et al., (2002), Muscle and Nerve, vol. 25 No. 1, Jan., pp. 4-16.
Dubaquite et al.,(1998), Biochemistry, vol. 38, May 18, pp. 6386-6396.
Shin, S-U et al., (1994), Journal of Biological Chemistry, vol. 269, No. 7, Feb. 18, pp. 4979-4985.
Shin, S-U et al., (1990), PNAS, vol. 87, No. 14, pp. 5322-5326.
Water et al., (1999), Angiostatin binds to smooth muscle cells in the coronary . . . , Arteriosclerosis Thrombosis & Vascular Biology, vol. 19, pp. 2041-2048.
Francis et al., (1995), CuZn Superoxide Dismutase (SOD-1): Tetanus Toxin Fragment C Hybrid . . . , J. Biol. Chem., vol. 270, pp. 15434-15442.
Halin et al., (2002), Enhancement of the antitumor activity of interleukin-12 by targeted delivery to neovasculature, Nature Biotechnology vol. 20, pp. 264-269.
Ohno et al., (1995) Cell targeting for gene delivery . . . , Biochemical and molecular medicine, vol. 56, pp. 172-175.
Samoylova et al., (1998), Elucidation of muscle-binding peptides by phage display screen, Muscle and Nerve, vol. 22, pp. 460-466.
Donalies et al., (1991) Expression of m-cadherin, a member of the caderin multigene family . . . , Proc. Natl. Acad. Sci. USA, vol. 88, pp. 8024-8028.
Chappuis-Flament et al., (2001), Multiple cadherin extracellular repeats mediate homophilic bindings and adhesion, J. Cell Bio, vol. 154, pp. 231-243.
Leal, A. M.O. et al., (2002), Endocrinology, vol. 143, No. 3, pp. 964-969.
Hill, J. J. et el., (2002), J. of Biol. Chem, vol. 277, No. 43, pp. 40735-40741.
Wolfman, N. M. et al, (2003), PNAS, vol. 100, No. 26, pp. 15842-154846.
Kaufman. U. et al., (1999), Journal of Cell Science, vol. 112, pp. 55-67.

*Primary Examiner*—Robert Landsman
*Assistant Examiner*—Ian Dang
(74) *Attorney, Agent, or Firm*—Valeta Gregg, Esq.; Izumi Yokoyama, Esq.

(57) ABSTRACT

A targeting fusion protein comprising a component that comprises a (i) ligand or derivative or fragment thereof that binds a pre-selected target surface protein, such as a receptor, and (ii) an active agent or therapeutic agent(s), and further optionally (iii) a multimerizing component and/or (iv) a signal sequence. In a preferred embodiment, the targeting fusion polypeptide targets muscle and is useful to treat a muscle-related disease or condition, such as muscle atrophy.

2 Claims, No Drawings

SEQUENCE LISTING

```
<160> NUMBER OF SEQ ID NOS: 54

<210> SEQ ID NO 1
<211> LENGTH: 633
<212> TYPE: PRT
<213> ORGANISM: homo sapien

<400> SEQUENCE: 1

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Met Phe Pro Ala Met Pro Leu Ser Ser Leu Phe Val Asn Gly Pro Arg
    50                  55                  60

Thr Leu Cys Gly Ala Glu Leu Val Leu Gln Phe Val Cys Gly Asp Arg
65                  70                  75                  80

Gly Phe Tyr Phe Asn Lys Pro Thr Gly Tyr Gly Ser Ser Ser Arg Arg
                85                  90                  95

Ala Pro Gln Thr Gly Ile Val Asp Glu Cys Cys Phe Arg Ser Cys Asp
            100                 105                 110

Leu Arg Arg Leu Glu Met Tyr Cys Ala Pro Leu Lys Pro Ala Lys Ser
        115                 120                 125

Ala Arg Ser Val Arg Ala Gln Arg His Thr Asp Met Pro Lys Thr Gln
    130                 135                 140

Lys Glu Val His Leu Lys Asn Ala Ser Arg Gly Ser Ala Gly Asn Lys
145                 150                 155                 160

Asn Tyr Arg Met Gly Thr Gly Lys Ser Pro Cys Gln Pro Asn Pro
                165                 170                 175

Cys His Gly Ala Ala Pro Cys Arg Val Leu Pro Glu Gly Gly Ala Gln
            180                 185                 190

Cys Glu Cys Pro Leu Gly Arg Glu Gly Thr Phe Cys Gln Thr Ala Ser
        195                 200                 205

Gly Gln Asp Gly Ser Gly Pro Phe Leu Ala Asp Phe Asn Gly Phe Ser
    210                 215                 220
```

```
His Leu Glu Leu Arg Gly Leu His Thr Phe Ala Arg Asp Leu Gly Glu
225                 230                 235                 240

Lys Met Ala Leu Glu Val Val Phe Leu Ala Arg Gly Pro Ser Gly Leu
                245                 250                 255

Leu Leu Tyr Asn Gly Gln Lys Thr Asp Gly Lys Gly Asp Phe Val Ser
            260                 265                 270

Leu Ala Leu Arg Asp Arg Arg Leu Glu Phe Arg Tyr Asp Leu Gly Lys
                275                 280                 285

Gly Ala Ala Val Ile Arg Ser Arg Glu Pro Val Thr Leu Gly Ala Trp
290                 295                 300

Thr Arg Val Ser Leu Glu Arg Asn Gly Arg Lys Gly Ala Leu Arg Val
305                 310                 315                 320

Gly Asp Gly Pro Arg Val Leu Gly Glu Ser Pro Val Pro His Thr Val
                325                 330                 335

Leu Asn Leu Lys Glu Pro Leu Tyr Val Gly Ala Pro Asp Phe Ser
            340                 345                 350

Lys Leu Ala Arg Ala Ala Val Ser Ser Gly Phe Asp Gly Ala Ile
            355                 360                 365

Gln Leu Val Ser Leu Gly Gly Arg Gln Leu Leu Thr Pro Glu His Val
    370                 375                 380

Leu Arg Gln Val Asp Val Thr Ser Phe Ala Gly His Pro Cys Thr Arg
385                 390                 395                 400

Ala Ser Gly His Pro Cys Leu Asn Gly Ala Ser Cys Val Pro Arg Glu
                405                 410                 415

Ala Ala Tyr Val Cys Leu Cys Pro Gly Gly Phe Ser Gly Pro His Cys
                420                 425                 430

Glu Lys Gly Leu Val Glu Lys Ser Ala Gly Asp Val Asp Thr Leu Ala
            435                 440                 445

Phe Asp Gly Arg Thr Phe Val Glu Tyr Leu Asn Ala Val Thr Glu Ser
450                 455                 460

Glu Leu Ala Asn Glu Ile Pro Val Glu Lys Ala Leu Gln Ser Asn His
465                 470                 475                 480

Phe Glu Leu Ser Leu Arg Thr Glu Ala Thr Gln Gly Leu Val Leu Trp
                485                 490                 495

Ser Gly Lys Ala Thr Glu Arg Ala Asp Tyr Val Ala Leu Ala Ile Val
            500                 505                 510

Asp Gly His Leu Gln Leu Ser Tyr Asn Leu Gly Ser Gln Pro Val Val
            515                 520                 525

Leu Arg Ser Thr Val Pro Val Asn Thr Asn Arg Trp Leu Arg Val Val
530                 535                 540

Ala His Arg Glu Gln Arg Glu Gly Ser Leu Gln Val Gly Asn Glu Ala
545                 550                 555                 560

Pro Val Thr Gly Ser Ser Pro Leu Gly Ala Thr Gln Leu Asp Thr Asp
                565                 570                 575

Gly Ala Leu Trp Leu Gly Gly Leu Pro Glu Leu Pro Val Gly Pro Ala
            580                 585                 590

Leu Pro Lys Ala Tyr Gly Thr Gly Phe Val Gly Cys Leu Arg Asp Val
            595                 600                 605

Val Val Gly Arg His Pro Leu His Leu Leu Glu Asp Ala Val Thr Lys
            610                 615                 620

Pro Glu Leu Arg Pro Cys Pro Thr Pro
625                 630
```

```
<210> SEQ ID NO 2
<211> LENGTH: 587
<212> TYPE: PRT
<213> ORGANISM: homo sapien

<400> SEQUENCE: 2

Met Phe Pro Ala Met Pro Leu Ser Ser Leu Phe Val Asn Gly Pro Arg
 1               5                  10                  15

Thr Leu Cys Gly Ala Glu Leu Val Asp Ala Leu Gln Phe Val Cys Gly
            20                  25                  30

Asp Arg Gly Phe Tyr Phe Asn Lys Pro Thr Gly Tyr Gly Ser Ser Ser
        35                  40                  45

Arg Arg Ala Pro Gln Thr Gly Ile Val Asp Glu Cys Cys Phe Arg Ser
    50                  55                  60

Cys Asp Leu Arg Arg Leu Glu Met Tyr Cys Ala Pro Leu Lys Pro Ala
65                  70                  75                  80

Lys Ser Ala Arg Ser Val Arg Ala Gln Arg His Thr Asp Met Pro Lys
                85                  90                  95

Thr Gln Lys Glu Val His Leu Lys Asn Ala Ser Arg Gly Ser Ala Gly
            100                 105                 110

Asn Lys Asn Tyr Arg Met Gly Thr Gly Gly Lys Ser Pro Cys Gln Pro
        115                 120                 125

Asn Pro Cys His Gly Ala Ala Pro Cys Arg Val Leu Pro Glu Gly Gly
    130                 135                 140

Ala Gln Cys Glu Cys Pro Leu Gly Arg Glu Gly Thr Phe Cys Gln Thr
145                 150                 155                 160

Ala Ser Gly Gln Asp Gly Ser Gly Pro Phe Leu Ala Asp Phe Asn Gly
                165                 170                 175

Phe Ser His Leu Glu Leu Arg Gly Leu His Thr Phe Ala Arg Asp Leu
            180                 185                 190

Gly Glu Lys Met Ala Leu Glu Val Phe Leu Ala Arg Gly Pro Ser
        195                 200                 205

Gly Leu Leu Leu Tyr Asn Gly Gln Lys Thr Asp Gly Lys Gly Asp Phe
    210                 215                 220

Val Ser Leu Ala Leu Arg Asp Arg Arg Leu Glu Phe Arg Tyr Asp Leu
225                 230                 235                 240

Gly Lys Gly Ala Ala Val Ile Arg Ser Arg Glu Pro Val Thr Leu Gly
                245                 250                 255

Ala Trp Thr Arg Val Ser Leu Glu Arg Asn Gly Arg Lys Gly Ala Leu
            260                 265                 270

Arg Val Gly Asp Gly Pro Arg Val Leu Gly Glu Ser Pro Val Pro His
        275                 280                 285

Thr Val Leu Asn Leu Lys Glu Pro Leu Tyr Val Gly Gly Ala Pro Asp
    290                 295                 300

Phe Ser Lys Leu Ala Arg Ala Ala Ala Val Ser Ser Gly Phe Asp Gly
305                 310                 315                 320

Ala Ile Gln Leu Val Ser Leu Gly Gly Arg Gln Leu Leu Thr Pro Glu
                325                 330                 335

His Val Leu Arg Gln Val Asp Val Thr Ser Phe Ala Gly His Pro Cys
            340                 345                 350

Thr Arg Ala Ser Gly His Pro Cys Leu Asn Gly Ala Ser Cys Val Pro
        355                 360                 365

Arg Glu Ala Ala Tyr Val Cys Leu Cys Pro Gly Gly Phe Ser Gly Pro
    370                 375                 380
```

```
His Cys Glu Lys Gly Leu Val Glu Lys Ser Ala Gly Asp Val Asp Thr
385                 390                 395                 400

Leu Ala Phe Asp Gly Arg Thr Phe Val Glu Tyr Leu Asn Ala Val Thr
                405                 410                 415

Glu Ser Glu Leu Ala Asn Glu Ile Pro Val Glu Lys Ala Leu Gln Ser
            420                 425                 430

Asn His Phe Glu Leu Ser Leu Arg Thr Glu Ala Thr Gln Gly Leu Val
        435                 440                 445

Leu Trp Ser Gly Lys Ala Thr Glu Arg Ala Asp Tyr Val Ala Leu Ala
450                 455                 460

Ile Val Asp Gly His Leu Gln Leu Ser Tyr Asn Leu Gly Ser Gln Pro
465                 470                 475                 480

Val Val Leu Arg Ser Thr Val Pro Val Asn Thr Asn Arg Trp Leu Arg
                485                 490                 495

Val Val Ala His Arg Glu Gln Arg Glu Gly Ser Leu Gln Val Gly Asn
            500                 505                 510

Glu Ala Pro Val Thr Gly Ser Ser Pro Leu Gly Ala Thr Gln Leu Asp
        515                 520                 525

Thr Asp Gly Ala Leu Trp Leu Gly Leu Pro Glu Leu Pro Val Gly
530                 535                 540

Pro Ala Leu Pro Lys Ala Tyr Gly Thr Gly Phe Val Gly Cys Leu Arg
545                 550                 555                 560

Asp Val Val Val Gly Arg His Pro Leu His Leu Leu Glu Asp Ala Val
                565                 570                 575

Thr Lys Pro Glu Leu Arg Pro Cys Pro Thr Pro
            580                 585

<210> SEQ ID NO 3
<211> LENGTH: 622
<212> TYPE: PRT
<213> ORGANISM: homo sapien

<400> SEQUENCE: 3

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Arg Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met Gly Thr Gly Gly Lys Ser Pro
145                 150                 155                 160

Cys Gln Pro Asn Pro Cys His Gly Ala Ala Pro Cys Arg Val Leu Pro
```

-continued

```
                165                 170                 175
Glu Gly Gly Ala Gln Cys Glu Cys Pro Leu Gly Arg Glu Gly Thr Phe
            180                 185                 190
Cys Gln Thr Ala Ser Gly Gln Asp Gly Ser Gly Pro Phe Leu Ala Asp
            195                 200                 205
Phe Asn Gly Phe Ser His Leu Glu Leu Arg Gly Leu His Thr Phe Ala
            210                 215                 220
Arg Asp Leu Gly Glu Lys Met Ala Leu Glu Val Val Phe Leu Ala Arg
225                 230                 235                 240
Gly Pro Ser Gly Leu Leu Leu Tyr Asn Gly Gln Lys Thr Asp Gly Lys
            245                 250                 255
Gly Asp Phe Val Ser Leu Ala Leu Arg Asp Arg Arg Leu Glu Phe Arg
            260                 265                 270
Tyr Asp Leu Gly Lys Gly Ala Ala Val Ile Arg Ser Arg Glu Pro Val
            275                 280                 285
Thr Leu Gly Ala Trp Thr Arg Val Ser Leu Glu Arg Asn Gly Arg Lys
            290                 295                 300
Gly Ala Leu Arg Val Gly Asp Gly Pro Arg Val Leu Gly Glu Ser Pro
305                 310                 315                 320
Val Pro His Thr Val Leu Asn Leu Lys Glu Pro Leu Tyr Val Gly Gly
            325                 330                 335
Ala Pro Asp Phe Ser Lys Leu Ala Arg Ala Ala Ala Val Ser Ser Gly
            340                 345                 350
Phe Asp Gly Ala Ile Gln Leu Val Ser Leu Gly Gly Arg Gln Leu Leu
            355                 360                 365
Thr Pro Glu His Val Leu Arg Gln Val Asp Val Thr Ser Phe Ala Gly
            370                 375                 380
His Pro Cys Thr Arg Ala Ser Gly His Pro Cys Leu Asn Gly Ala Ser
385                 390                 395                 400
Cys Val Pro Arg Glu Ala Ala Tyr Val Cys Leu Cys Pro Gly Gly Phe
            405                 410                 415
Ser Gly Pro His Cys Glu Lys Gly Leu Val Glu Lys Ser Ala Gly Asp
            420                 425                 430
Val Asp Thr Leu Ala Phe Asp Gly Arg Thr Phe Val Glu Tyr Leu Asn
            435                 440                 445
Ala Val Thr Glu Ser Glu Leu Ala Asn Glu Ile Pro Val Glu Lys Ala
            450                 455                 460
Leu Gln Ser Asn His Phe Glu Leu Ser Leu Arg Thr Glu Ala Thr Gln
465                 470                 475                 480
Gly Leu Val Leu Trp Ser Gly Lys Ala Thr Glu Arg Ala Asp Tyr Val
            485                 490                 495
Ala Leu Ala Ile Val Asp Gly His Leu Gln Leu Ser Tyr Asn Leu Gly
            500                 505                 510
Ser Gln Pro Val Val Leu Arg Ser Thr Val Pro Val Asn Thr Asn Arg
            515                 520                 525
Trp Leu Arg Val Val Ala His Arg Glu Gln Arg Glu Gly Ser Leu Gln
            530                 535                 540
Val Gly Asn Glu Ala Pro Val Thr Gly Ser Ser Pro Leu Gly Ala Thr
545                 550                 555                 560
Gln Leu Asp Thr Asp Gly Ala Leu Trp Leu Gly Gly Leu Pro Glu Leu
            565                 570                 575
Pro Val Gly Pro Ala Leu Pro Lys Ala Tyr Gly Thr Gly Phe Val Gly
            580                 585                 590
```

```
Cys Leu Arg Asp Val Val Gly Arg His Pro Leu His Leu Leu Glu
        595                 600                 605

Asp Ala Val Thr Lys Pro Glu Leu Arg Pro Cys Pro Thr Pro
        610                 615                 620

<210> SEQ ID NO 4
<211> LENGTH: 574
<212> TYPE: PRT
<213> ORGANISM: homo sapien

<400> SEQUENCE: 4

Gly Pro Arg Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
             20                  25                  30

Ser Ser Ser Arg Arg Ala Pro Gln Thr Gly Ile Val Asp Glu Cys Cys
         35                  40                  45

Phe Arg Ser Cys Asp Leu Arg Arg Leu Glu Met Tyr Cys Ala Pro Leu
 50                  55                  60

Lys Pro Ala Lys Ser Ala Arg Ser Val Arg Ala Gln Arg His Thr Asp
65                  70                  75                  80

Met Pro Lys Thr Gln Lys Glu Val His Leu Lys Asn Ala Ser Arg Gly
                 85                  90                  95

Ser Ala Gly Asn Lys Asn Tyr Arg Met Gly Thr Gly Gly Lys Ser Pro
            100                 105                 110

Cys Gln Pro Asn Pro Cys His Gly Ala Ala Pro Cys Arg Val Leu Pro
        115                 120                 125

Glu Gly Gly Ala Gln Cys Glu Cys Pro Leu Gly Arg Glu Gly Thr Phe
    130                 135                 140

Cys Gln Thr Ala Ser Gly Gln Asp Gly Ser Gly Pro Phe Leu Ala Asp
145                 150                 155                 160

Phe Asn Gly Phe Ser His Leu Glu Leu Arg Gly Leu His Thr Phe Ala
                165                 170                 175

Arg Asp Leu Gly Glu Lys Met Ala Leu Glu Val Val Phe Leu Ala Arg
            180                 185                 190

Gly Pro Ser Gly Leu Leu Leu Tyr Asn Gly Gln Lys Thr Asp Gly Lys
        195                 200                 205

Gly Asp Phe Val Ser Leu Ala Leu Arg Asp Arg Arg Leu Glu Phe Arg
    210                 215                 220

Tyr Asp Leu Gly Lys Gly Ala Ala Val Ile Arg Ser Arg Glu Pro Val
225                 230                 235                 240

Thr Leu Gly Ala Trp Thr Arg Val Ser Leu Glu Arg Asn Gly Arg Lys
                245                 250                 255

Gly Ala Leu Arg Val Gly Asp Gly Pro Arg Val Leu Gly Glu Ser Pro
            260                 265                 270

Val Pro His Thr Val Leu Asn Leu Lys Glu Pro Leu Tyr Val Gly Gly
        275                 280                 285

Ala Pro Asp Phe Ser Lys Leu Ala Arg Ala Ala Ala Val Ser Ser Gly
    290                 295                 300

Phe Asp Gly Ala Ile Gln Leu Val Ser Leu Gly Gly Arg Gln Leu Leu
305                 310                 315                 320

Thr Pro Glu His Val Leu Arg Gln Val Asp Val Thr Ser Phe Ala Gly
                325                 330                 335

His Pro Cys Thr Arg Ala Ser Gly His Pro Cys Leu Asn Gly Ala Ser
```

```
                    340                 345                 350
Cys Val Pro Arg Glu Ala Ala Tyr Val Cys Leu Cys Pro Gly Gly Phe
        355                 360                 365

Ser Gly Pro His Cys Glu Lys Gly Leu Val Glu Lys Ser Ala Gly Asp
370                 375                 380

Val Asp Thr Leu Ala Phe Asp Gly Arg Thr Phe Val Glu Tyr Leu Asn
385                 390                 395                 400

Ala Val Thr Glu Ser Glu Leu Ala Asn Glu Ile Pro Val Glu Lys Ala
                405                 410                 415

Leu Gln Ser Asn His Phe Glu Leu Ser Leu Arg Thr Glu Ala Thr Gln
            420                 425                 430

Gly Leu Val Leu Trp Ser Gly Lys Ala Thr Glu Arg Ala Asp Tyr Val
        435                 440                 445

Ala Leu Ala Ile Val Asp Gly His Leu Gln Leu Ser Tyr Asn Leu Gly
    450                 455                 460

Ser Gln Pro Val Val Leu Arg Ser Thr Val Pro Val Asn Thr Asn Arg
465                 470                 475                 480

Trp Leu Arg Val Val Ala His Arg Glu Gln Arg Glu Gly Ser Leu Gln
                485                 490                 495

Val Gly Asn Glu Ala Pro Val Thr Gly Ser Ser Pro Leu Gly Ala Thr
            500                 505                 510

Gln Leu Asp Thr Asp Gly Ala Leu Trp Leu Gly Gly Leu Pro Glu Leu
        515                 520                 525

Pro Val Gly Pro Ala Leu Pro Lys Ala Tyr Gly Thr Gly Phe Val Gly
    530                 535                 540

Cys Leu Arg Asp Val Val Val Gly Arg His Pro Leu His Leu Leu Glu
545                 550                 555                 560

Asp Ala Val Thr Lys Pro Glu Leu Arg Pro Cys Pro Thr Pro
                565                 570

<210> SEQ ID NO 5
<211> LENGTH: 628
<212> TYPE: PRT
<213> ORGANISM: homo sapien

<400> SEQUENCE: 5

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Met Phe Pro Ala Met Pro Leu Ser Ser Leu Phe Val Asn Gly Pro Arg
    50                  55                  60

Thr Leu Cys Gly Ala Glu Leu Val Asp Ala Leu Gln Phe Val Cys Gly
65                  70                  75                  80

Asp Arg Gly Phe Tyr Phe Asn Lys Pro Thr Gly Tyr Gly Ser Ser Ser
                85                  90                  95

Arg Arg Ala Pro Gln Thr Gly Ile Val Asp Glu Cys Cys Phe Arg Ser
            100                 105                 110

Cys Asp Leu Arg Arg Leu Glu Met Tyr Cys Ala Pro Leu Lys Pro Ala
        115                 120                 125

Lys Ser Ala Arg Ser Val Arg Ala Gln Arg His Thr Asp Met Pro Lys
    130                 135                 140
```

-continued

```
Thr Gln Lys Glu Val His Leu Lys Asn Ala Ser Arg Gly Ser Ala Gly
145                 150                 155                 160

Asn Lys Asn Tyr Arg Met Gly Thr Gly Gly Lys Ser Pro Cys Gln Pro
                165                 170                 175

Asn Pro Cys His Gly Ala Ala Pro Cys Arg Val Leu Pro Glu Gly Gly
            180                 185                 190

Ala Gln Cys Glu Cys Pro Leu Gly Arg Glu Gly Thr Phe Cys Gln Thr
        195                 200                 205

Ala Ser Gly Gln Asp Gly Ser Gly Pro Phe Leu Ala Asp Phe Asn Gly
    210                 215                 220

Phe Ser His Leu Glu Leu Arg Gly Leu His Thr Phe Ala Arg Asp Leu
225                 230                 235                 240

Gly Glu Lys Met Ala Leu Glu Val Val Phe Leu Ala Arg Gly Pro Ser
                245                 250                 255

Gly Leu Leu Leu Tyr Asn Gly Gln Lys Thr Asp Gly Lys Gly Asp Phe
            260                 265                 270

Val Ser Leu Ala Leu Arg Asp Arg Arg Leu Glu Phe Arg Tyr Asp Leu
        275                 280                 285

Gly Lys Gly Ala Ala Val Ile Arg Ser Arg Glu Pro Val Thr Leu Gly
    290                 295                 300

Ala Trp Thr Arg Val Ser Leu Glu Arg Asn Gly Arg Lys Gly Ala Leu
305                 310                 315                 320

Arg Val Gly Asp Gly Pro Arg Val Leu Gly Glu Ser Pro Val Pro His
                325                 330                 335

Thr Val Leu Asn Leu Lys Glu Pro Leu Tyr Val Gly Gly Ala Pro Asp
            340                 345                 350

Phe Ser Lys Leu Ala Arg Ala Ala Val Ser Ser Gly Phe Asp Gly
        355                 360                 365

Ala Ile Gln Leu Val Ser Leu Gly Gly Arg Gln Leu Leu Thr Pro Glu
    370                 375                 380

His Val Leu Arg Gln Val Asp Val Thr Ser Phe Ala Gly His Pro Cys
385                 390                 395                 400

Thr Arg Ala Ser Gly His Pro Cys Leu Asn Gly Ala Ser Cys Val Pro
                405                 410                 415

Arg Glu Ala Ala Tyr Val Cys Leu Cys Pro Gly Gly Phe Ser Gly Pro
            420                 425                 430

His Cys Glu Lys Gly Leu Val Glu Lys Ser Ala Gly Asp Val Asp Thr
        435                 440                 445

Leu Ala Phe Asp Gly Arg Thr Phe Val Glu Tyr Leu Asn Ala Val Thr
    450                 455                 460

Glu Ser Glu Glu Lys Ala Leu Gln Ser Asn His Phe Glu Leu Ser Leu
465                 470                 475                 480

Arg Thr Glu Ala Thr Gln Gly Leu Val Leu Trp Ser Gly Lys Ala Thr
                485                 490                 495

Glu Arg Ala Asp Tyr Val Ala Leu Ala Ile Val Asp Gly His Leu Gln
            500                 505                 510

Leu Ser Tyr Asn Leu Gly Ser Gln Pro Val Val Leu Arg Ser Thr Val
        515                 520                 525

Pro Val Asn Thr Asn Arg Trp Leu Arg Val Val Ala His Arg Glu Gln
    530                 535                 540

Arg Glu Gly Ser Leu Gln Val Gly Asn Glu Ala Pro Val Thr Gly Ser
545                 550                 555                 560

Ser Pro Leu Gly Ala Thr Gln Leu Asp Thr Asp Gly Ala Leu Trp Leu
```

```
                   565                 570                 575
Gly Gly Leu Pro Glu Leu Pro Val Gly Pro Ala Leu Pro Lys Ala Tyr
            580                 585                 590
Gly Thr Gly Phe Val Gly Cys Leu Arg Asp Val Val Gly Arg His
            595                 600                 605
Pro Leu His Leu Leu Glu Asp Ala Val Thr Lys Pro Glu Leu Arg Pro
    610                 615                 620
Cys Pro Thr Pro
625

<210> SEQ ID NO 6
<211> LENGTH: 580
<212> TYPE: PRT
<213> ORGANISM: homo sapien

<400> SEQUENCE: 6

Met Phe Pro Ala Met Pro Leu Ser Ser Leu Phe Val Asn Gly Pro Arg
  1               5                  10                  15
Thr Leu Cys Gly Ala Glu Leu Val Asp Ala Leu Gln Phe Val Cys Gly
             20                  25                  30
Asp Arg Gly Phe Tyr Phe Asn Lys Pro Thr Gly Tyr Gly Ser Ser Ser
         35                  40                  45
Arg Arg Ala Pro Gln Thr Gly Ile Val Asp Glu Cys Cys Phe Arg Ser
     50                  55                  60
Cys Asp Leu Arg Arg Leu Glu Met Tyr Cys Ala Pro Leu Lys Pro Ala
 65                  70                  75                  80
Lys Ser Ala Arg Ser Val Arg Ala Gln Arg His Thr Asp Met Pro Lys
                 85                  90                  95
Thr Gln Lys Glu Val His Leu Lys Asn Ala Ser Arg Gly Ser Ala Gly
            100                 105                 110
Asn Lys Asn Tyr Arg Met Gly Thr Gly Gly Lys Ser Pro Cys Gln Pro
        115                 120                 125
Asn Pro Cys His Gly Ala Ala Pro Cys Arg Val Leu Pro Glu Gly Gly
    130                 135                 140
Ala Gln Cys Glu Cys Pro Leu Gly Arg Glu Gly Thr Phe Cys Gln Thr
145                 150                 155                 160
Ala Ser Gly Gln Asp Gly Ser Gly Pro Phe Leu Ala Asp Phe Asn Gly
                165                 170                 175
Phe Ser His Leu Glu Leu Arg Gly Leu His Thr Phe Ala Arg Asp Leu
            180                 185                 190
Gly Glu Lys Met Ala Leu Glu Val Val Phe Leu Ala Arg Gly Pro Ser
        195                 200                 205
Gly Leu Leu Leu Tyr Asn Gly Gln Lys Thr Asp Gly Lys Gly Asp Phe
    210                 215                 220
Val Ser Leu Ala Leu Arg Asp Arg Arg Leu Glu Phe Arg Tyr Asp Leu
225                 230                 235                 240
Gly Lys Gly Ala Ala Val Ile Arg Ser Arg Glu Pro Val Thr Leu Gly
                245                 250                 255
Ala Trp Thr Arg Val Ser Leu Glu Arg Asn Gly Arg Lys Gly Ala Leu
            260                 265                 270
Arg Val Gly Asp Gly Pro Arg Val Leu Gly Glu Ser Pro Val Pro His
        275                 280                 285
Thr Val Leu Asn Leu Lys Glu Pro Leu Tyr Val Gly Gly Ala Pro Asp
    290                 295                 300
```

```
Phe Ser Lys Leu Ala Arg Ala Ala Val Ser Ser Gly Phe Asp Gly
305                 310                 315                 320

Ala Ile Gln Leu Val Ser Leu Gly Gly Arg Gln Leu Leu Thr Pro Glu
            325                 330                 335

His Val Leu Arg Gln Val Asp Val Thr Ser Phe Ala Gly His Pro Cys
            340                 345                 350

Thr Arg Ala Ser Gly His Pro Cys Leu Asn Gly Ala Ser Cys Val Pro
            355                 360                 365

Arg Glu Ala Ala Tyr Val Cys Leu Cys Pro Gly Gly Phe Ser Gly Pro
    370                 375                 380

His Cys Glu Lys Gly Leu Val Glu Lys Ser Ala Gly Asp Val Asp Thr
385                 390                 395                 400

Leu Ala Phe Asp Gly Arg Thr Phe Val Glu Tyr Leu Asn Ala Val Thr
                405                 410                 415

Glu Ser Glu Glu Lys Ala Leu Gln Ser Asn His Phe Glu Leu Ser Leu
            420                 425                 430

Arg Thr Glu Ala Thr Gln Gly Leu Val Leu Trp Ser Gly Lys Ala Thr
    435                 440                 445

Glu Arg Ala Asp Tyr Val Ala Leu Ala Ile Val Asp Gly His Leu Gln
450                 455                 460

Leu Ser Tyr Asn Leu Gly Ser Gln Pro Val Val Leu Arg Ser Thr Val
465                 470                 475                 480

Pro Val Asn Thr Asn Arg Trp Leu Arg Val Val Ala His Arg Glu Gln
                485                 490                 495

Arg Glu Gly Ser Leu Gln Val Gly Asn Glu Ala Pro Val Thr Gly Ser
            500                 505                 510

Ser Pro Leu Gly Ala Thr Gln Leu Asp Thr Asp Gly Ala Leu Trp Leu
    515                 520                 525

Gly Gly Leu Pro Glu Leu Pro Val Gly Pro Ala Leu Pro Lys Ala Tyr
530                 535                 540

Gly Thr Gly Phe Val Gly Cys Leu Arg Asp Val Val Val Gly Arg His
545                 550                 555                 560

Pro Leu His Leu Leu Glu Asp Ala Val Thr Lys Pro Glu Leu Arg Pro
                565                 570                 575

Cys Pro Thr Pro
            580

<210> SEQ ID NO 7
<211> LENGTH: 615
<212> TYPE: PRT
<213> ORGANISM: homo sapien

<400> SEQUENCE: 7

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Arg Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95
```

-continued

```
Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
            115                 120                 125

Met Pro Lys Thr Gln Lys Glu Val His Leu Lys Asn Ala Ser Arg Gly
            130                 135                 140

Ser Ala Gly Asn Lys Asn Tyr Arg Met Gly Thr Gly Gly Lys Ser Pro
145                 150                 155                 160

Cys Gln Pro Asn Pro Cys His Gly Ala Ala Pro Cys Arg Val Leu Pro
                165                 170                 175

Glu Gly Gly Ala Gln Cys Glu Cys Pro Leu Gly Arg Glu Gly Thr Phe
            180                 185                 190

Cys Gln Thr Ala Ser Gly Gln Asp Gly Ser Gly Pro Phe Leu Ala Asp
            195                 200                 205

Phe Asn Gly Phe Ser His Leu Glu Leu Arg Gly Leu His Thr Phe Ala
            210                 215                 220

Arg Asp Leu Gly Glu Lys Met Ala Leu Glu Val Val Phe Leu Ala Arg
225                 230                 235                 240

Gly Pro Ser Gly Leu Leu Leu Tyr Asn Gly Gln Lys Thr Asp Gly Lys
                245                 250                 255

Gly Asp Phe Val Ser Leu Ala Leu Arg Asp Arg Arg Leu Glu Phe Arg
            260                 265                 270

Tyr Asp Leu Gly Lys Gly Ala Ala Val Ile Arg Ser Arg Glu Pro Val
            275                 280                 285

Thr Leu Gly Ala Trp Thr Arg Val Ser Leu Glu Arg Asn Gly Arg Lys
            290                 295                 300

Gly Ala Leu Arg Val Gly Asp Gly Pro Arg Val Leu Gly Glu Ser Pro
305                 310                 315                 320

Val Pro His Thr Val Leu Asn Leu Lys Glu Pro Leu Tyr Val Gly Gly
                325                 330                 335

Ala Pro Asp Phe Ser Lys Leu Ala Arg Ala Ala Ala Val Ser Ser Gly
            340                 345                 350

Phe Asp Gly Ala Ile Gln Leu Val Ser Leu Gly Gly Arg Gln Leu Leu
            355                 360                 365

Thr Pro Glu His Val Leu Arg Gln Val Asp Val Thr Ser Phe Ala Gly
            370                 375                 380

His Pro Cys Thr Arg Ala Ser Gly His Pro Cys Leu Asn Gly Ala Ser
385                 390                 395                 400

Cys Val Pro Arg Glu Ala Ala Tyr Val Cys Leu Cys Pro Gly Gly Phe
            405                 410                 415

Ser Gly Pro His Cys Glu Lys Gly Leu Val Glu Lys Ser Ala Gly Asp
            420                 425                 430

Val Asp Thr Leu Ala Phe Asp Gly Arg Thr Phe Val Glu Tyr Leu Asn
            435                 440                 445

Ala Val Thr Glu Ser Glu Glu Lys Ala Leu Gln Ser Asn His Phe Glu
450                 455                 460

Leu Ser Leu Arg Thr Glu Ala Thr Gln Gly Leu Val Leu Trp Ser Gly
465                 470                 475                 480

Lys Ala Thr Glu Arg Ala Asp Tyr Val Ala Leu Ala Ile Val Asp Gly
                485                 490                 495

His Leu Gln Leu Ser Tyr Asn Leu Gly Ser Gln Pro Val Val Leu Arg
            500                 505                 510
```

```
Ser Thr Val Pro Val Asn Thr Asn Arg Trp Leu Arg Val Ala His
        515                 520                 525

Arg Glu Gln Arg Glu Gly Ser Leu Gln Val Gly Asn Glu Ala Pro Val
        530                 535                 540

Thr Gly Ser Ser Pro Leu Gly Ala Thr Gln Leu Asp Thr Asp Gly Ala
545                 550                 555                 560

Leu Trp Leu Gly Gly Leu Pro Glu Leu Pro Val Gly Pro Ala Leu Pro
                    565                 570                 575

Lys Ala Tyr Gly Thr Gly Phe Val Gly Cys Leu Arg Asp Val Val Val
            580                 585                 590

Gly Arg His Pro Leu His Leu Leu Glu Asp Ala Val Thr Lys Pro Glu
        595                 600                 605

Leu Arg Pro Cys Pro Thr Pro
        610                 615

<210> SEQ ID NO 8
<211> LENGTH: 567
<212> TYPE: PRT
<213> ORGANISM: homo sapien

<400> SEQUENCE: 8

Gly Pro Arg Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
        50                  55                  60

Lys Pro Ala Lys Ser Ala Arg Ser Val Arg Ala Gln Arg His Thr Asp
65                  70                  75                  80

Met Pro Lys Thr Gln Lys Glu Val His Leu Lys Asn Ala Ser Arg Gly
                85                  90                  95

Ser Ala Gly Asn Lys Asn Tyr Arg Met Gly Thr Gly Gly Lys Ser Pro
            100                 105                 110

Cys Gln Pro Asn Pro Cys His Gly Ala Ala Pro Cys Arg Val Leu Pro
        115                 120                 125

Glu Gly Gly Ala Gln Cys Glu Cys Pro Leu Gly Arg Glu Gly Thr Phe
    130                 135                 140

Cys Gln Thr Ala Ser Gly Gln Asp Gly Ser Gly Pro Phe Leu Ala Asp
145                 150                 155                 160

Phe Asn Gly Phe Ser His Leu Glu Leu Arg Gly Leu His Thr Phe Ala
                165                 170                 175

Arg Asp Leu Gly Glu Lys Met Ala Leu Glu Val Val Phe Leu Ala Arg
            180                 185                 190

Gly Pro Ser Gly Leu Leu Leu Tyr Asn Gly Gln Lys Thr Asp Gly Lys
        195                 200                 205

Gly Asp Phe Val Ser Leu Ala Leu Arg Asp Arg Arg Leu Glu Phe Arg
    210                 215                 220

Tyr Asp Leu Gly Lys Gly Ala Ala Val Ile Arg Ser Arg Glu Pro Val
225                 230                 235                 240

Thr Leu Gly Ala Trp Thr Arg Val Ser Leu Glu Arg Asn Gly Arg Lys
                245                 250                 255

Gly Ala Leu Arg Val Gly Asp Gly Pro Arg Val Leu Gly Glu Ser Pro
            260                 265                 270
```

```
Val Pro His Thr Val Leu Asn Leu Lys Glu Pro Leu Tyr Val Gly Gly
            275                 280                 285

Ala Pro Asp Phe Ser Lys Leu Ala Arg Ala Ala Val Ser Ser Gly
            290                 295                 300

Phe Asp Gly Ala Ile Gln Leu Val Ser Leu Gly Gly Arg Gln Leu Leu
305                 310                 315                 320

Thr Pro Glu His Val Leu Arg Gln Val Asp Val Thr Ser Phe Ala Gly
                325                 330                 335

His Pro Cys Thr Arg Ala Ser Gly His Pro Cys Leu Asn Gly Ala Ser
                340                 345                 350

Cys Val Pro Arg Glu Ala Ala Tyr Val Cys Leu Cys Pro Gly Gly Phe
            355                 360                 365

Ser Gly Pro His Cys Glu Lys Gly Leu Val Glu Lys Ser Ala Gly Asp
            370                 375                 380

Val Asp Thr Leu Ala Phe Asp Gly Arg Thr Phe Val Glu Tyr Leu Asn
385                 390                 395                 400

Ala Val Thr Glu Ser Glu Glu Lys Ala Leu Gln Ser Asn His Phe Glu
                405                 410                 415

Leu Ser Leu Arg Thr Glu Ala Thr Gln Gly Leu Val Leu Trp Ser Gly
                420                 425                 430

Lys Ala Thr Glu Arg Ala Asp Tyr Val Ala Leu Ala Ile Val Asp Gly
            435                 440                 445

His Leu Gln Leu Ser Tyr Asn Leu Gly Ser Gln Pro Val Val Leu Arg
            450                 455                 460

Ser Thr Val Pro Val Asn Thr Asn Arg Trp Leu Arg Val Val Ala His
465                 470                 475                 480

Arg Glu Gln Arg Glu Gly Ser Leu Gln Val Gly Asn Glu Ala Pro Val
                485                 490                 495

Thr Gly Ser Ser Pro Leu Gly Ala Thr Gln Leu Asp Thr Asp Gly Ala
            500                 505                 510

Leu Trp Leu Gly Gly Leu Pro Glu Leu Pro Val Gly Pro Ala Leu Pro
            515                 520                 525

Lys Ala Tyr Gly Thr Gly Phe Val Gly Cys Leu Arg Asp Val Val Val
            530                 535                 540

Gly Arg His Pro Leu His Leu Leu Glu Asp Ala Val Thr Lys Pro Glu
545                 550                 555                 560

Leu Arg Pro Cys Pro Thr Pro
                565

<210> SEQ ID NO 9
<211> LENGTH: 296
<212> TYPE: PRT
<213> ORGANISM: homo sapien

<400> SEQUENCE: 9

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
             20                  25                  30

Arg Ala Pro Gln Thr Gly Ile Val Asp Glu Cys Cys Phe Arg Ser Cys
         35                  40                  45

Asp Leu Arg Arg Leu Glu Met Tyr Cys Ala Pro Leu Lys Pro Ala Lys
     50                  55                  60

Ser Ala Gly Thr Gly Asp Lys Thr His Thr Cys Pro Pro Cys Pro Ala
```

```
                65                  70                  75                  80
Pro Glu Leu Leu Gly Gly Pro Ser Val Phe Leu Phe Pro Pro Lys Pro
                    85                  90                  95
Lys Asp Thr Leu Met Ile Ser Arg Thr Pro Glu Val Thr Cys Val Val
                100                 105                 110
Val Asp Val Ser His Glu Asp Pro Glu Val Lys Phe Asn Trp Tyr Val
                115                 120                 125
Asp Gly Val Glu Val His Asn Ala Lys Thr Lys Pro Arg Glu Glu Gln
            130                 135                 140
Tyr Asn Ser Thr Tyr Arg Val Val Ser Val Leu Thr Val Leu His Gln
145                 150                 155                 160
Asp Trp Leu Asn Gly Lys Glu Tyr Lys Cys Lys Val Ser Asn Lys Ala
                165                 170                 175
Leu Pro Ala Pro Ile Glu Lys Thr Ile Ser Lys Ala Lys Gly Gln Pro
            180                 185                 190
Arg Glu Pro Gln Val Tyr Thr Leu Pro Pro Ser Arg Asp Glu Leu Thr
        195                 200                 205
Lys Asn Gln Val Ser Leu Thr Cys Leu Val Lys Gly Phe Tyr Pro Ser
    210                 215                 220
Asp Ile Ala Val Glu Trp Glu Ser Asn Gly Gln Pro Glu Asn Asn Tyr
225                 230                 235                 240
Lys Thr Thr Pro Pro Val Leu Asp Ser Asp Gly Ser Phe Phe Leu Tyr
                245                 250                 255
Ser Lys Leu Thr Val Asp Lys Ser Arg Trp Gln Gln Gly Asn Val Phe
            260                 265                 270
Ser Cys Ser Val Met His Glu Ala Leu His Asn His Tyr Thr Gln Lys
        275                 280                 285
Ser Leu Ser Leu Ser Pro Gly Lys
    290                 295

<210> SEQ ID NO 10
<211> LENGTH: 66
<212> TYPE: PRT
<213> ORGANISM: homo sapien

<400> SEQUENCE: 10

Thr Leu Cys Gly Ala Glu Leu Val Asp Ala Leu Gln Phe Val Cys Gly
1               5                   10                  15
Asp Arg Gly Phe Tyr Phe Asn Lys Pro Thr Gly Tyr Gly Ser Ser Ser
                20                  25                  30
Arg Ala Pro Gln Thr Gly Ile Val Asp Glu Cys Cys Phe Arg Ser Cys
            35                  40                  45
Asp Leu Arg Arg Leu Glu Met Tyr Cys Ala Pro Leu Lys Pro Ala Lys
        50                  55                  60
Ser Ala
65

<210> SEQ ID NO 11
<211> LENGTH: 69
<212> TYPE: PRT
<213> ORGANISM: homo sapien

<400> SEQUENCE: 11

Thr Leu Cys Gly Ala Glu Leu Val Asp Ala Leu Gln Phe Val Cys Gly
1               5                   10                  15
Asp Arg Gly Phe Tyr Phe Asn Lys Pro Thr Gly Tyr Gly Ser Ser Ser
```

```
                    20                  25                  30
Arg Ala Pro Gln Thr Gly Ile Val Asp Glu Cys Cys Phe Arg Ser Cys
            35                  40                  45
Asp Leu Arg Arg Leu Glu Met Tyr Cys Ala Pro Leu Lys Pro Ala Lys
        50                  55                  60
Ser Ala Gly Thr Gly
65

<210> SEQ ID NO 12
<211> LENGTH: 759
<212> TYPE: PRT
<213> ORGANISM: homo sapien

<400> SEQUENCE: 12

Met Ala Thr Gly Ser Arg Thr Ser Leu Leu Leu Ala Phe Gly Leu Leu
 1               5                  10                  15
Cys Leu Pro Trp Leu Gln Glu Gly Ser Ala Phe Pro Thr Ile Pro Leu
            20                  25                  30
Ser Arg Leu Phe Asp Asn Ala Met Leu Arg Ala His Arg Leu His Gln
        35                  40                  45
Leu Ala Phe Asp Thr Tyr Gln Glu Phe Glu Glu Ala Tyr Ile Pro Lys
    50                  55                  60
Glu Gln Lys Tyr Ser Phe Leu Gln Asn Pro Gln Thr Ser Leu Cys Phe
65                  70                  75                  80
Ser Glu Ser Ile Pro Thr Pro Ser Asn Arg Glu Glu Thr Gln Gln Lys
                85                  90                  95
Ser Asn Leu Glu Leu Leu Arg Ile Ser Leu Leu Leu Ile Gln Ser Trp
            100                 105                 110
Leu Glu Pro Val Gln Phe Leu Arg Ser Val Phe Ala Asn Ser Leu Val
        115                 120                 125
Tyr Gly Ala Ser Asp Ser Asn Val Tyr Asp Leu Leu Lys Asp Leu Glu
    130                 135                 140
Glu Gly Ile Gln Thr Leu Met Gly Arg Leu Glu Asp Gly Ser Pro Arg
145                 150                 155                 160
Thr Gly Gln Ile Phe Lys Gln Thr Tyr Ser Lys Phe Asp Thr Asn Ser
                165                 170                 175
His Asn Asp Asp Ala Leu Leu Lys Asn Tyr Gly Leu Leu Tyr Cys Phe
            180                 185                 190
Arg Lys Asp Met Asp Lys Val Glu Thr Phe Leu Arg Ile Val Gln Cys
        195                 200                 205
Arg Ser Val Glu Gly Ser Cys Gly Phe Gly Pro Gly Gly Pro Arg Thr
    210                 215                 220
Leu Cys Gly Ala Glu Leu Val Asp Ala Leu Gln Phe Val Cys Gly Asp
225                 230                 235                 240
Arg Gly Phe Tyr Phe Asn Lys Pro Thr Gly Tyr Gly Ser Ser Ser Arg
                245                 250                 255
Arg Ala Pro Gln Thr Gly Ile Val Asp Glu Cys Cys Phe Arg Ser Cys
            260                 265                 270
Asp Leu Arg Arg Leu Glu Met Tyr Cys Ala Pro Leu Lys Pro Ala Lys
        275                 280                 285
Ser Ala Gly Thr Gly Gly Lys Ser Pro Cys Gln Pro Asn Pro Cys His
    290                 295                 300
Gly Ala Ala Pro Cys Arg Val Leu Pro Glu Gly Gly Ala Gln Cys Glu
305                 310                 315                 320
```

-continued

Cys Pro Leu Gly Arg Glu Gly Thr Phe Cys Gln Thr Ala Ser Gly Gln
                325                 330                 335

Asp Gly Ser Gly Pro Phe Leu Ala Asp Phe Asn Gly Phe Ser His Leu
            340                 345                 350

Glu Leu Arg Gly Leu His Thr Phe Ala Arg Asp Leu Gly Glu Lys Met
        355                 360                 365

Ala Leu Glu Val Val Phe Leu Ala Arg Gly Pro Ser Gly Leu Leu Leu
370                 375                 380

Tyr Asn Gly Gln Lys Thr Asp Gly Lys Gly Asp Phe Val Ser Leu Ala
385                 390                 395                 400

Leu Arg Asp Arg Arg Leu Glu Phe Arg Tyr Asp Leu Gly Lys Gly Ala
                405                 410                 415

Ala Val Ile Arg Ser Arg Glu Pro Val Thr Leu Gly Ala Trp Thr Arg
            420                 425                 430

Val Ser Leu Glu Arg Asn Gly Arg Lys Gly Ala Leu Arg Val Gly Asp
        435                 440                 445

Gly Pro Arg Val Leu Gly Glu Ser Pro Val Pro His Thr Val Leu Asn
450                 455                 460

Leu Lys Glu Pro Leu Tyr Val Gly Gly Ala Pro Asp Phe Ser Lys Leu
465                 470                 475                 480

Ala Arg Ala Ala Ala Val Ser Ser Gly Phe Asp Gly Ala Ile Gln Leu
                485                 490                 495

Val Ser Leu Gly Gly Arg Gln Leu Leu Thr Pro Glu His Val Leu Arg
            500                 505                 510

Gln Val Asp Val Thr Ser Phe Ala Gly His Pro Cys Thr Arg Ala Ser
        515                 520                 525

Gly His Pro Cys Leu Asn Gly Ala Ser Cys Val Pro Arg Glu Ala Ala
530                 535                 540

Tyr Val Cys Leu Cys Pro Gly Phe Ser Gly Pro His Cys Glu Lys
545                 550                 555                 560

Gly Leu Val Glu Lys Ser Ala Gly Asp Val Asp Thr Leu Ala Phe Asp
                565                 570                 575

Gly Arg Thr Phe Val Glu Tyr Leu Asn Ala Val Thr Glu Ser Glu Leu
            580                 585                 590

Ala Asn Glu Ile Pro Val Glu Lys Ala Leu Gln Ser Asn His Phe Glu
        595                 600                 605

Leu Ser Leu Arg Thr Glu Ala Thr Gln Gly Leu Val Leu Trp Ser Gly
610                 615                 620

Lys Ala Thr Glu Arg Ala Asp Tyr Val Ala Leu Ala Ile Val Asp Gly
625                 630                 635                 640

His Leu Gln Leu Ser Tyr Asn Leu Gly Ser Gln Pro Val Val Leu Arg
                645                 650                 655

Ser Thr Val Pro Val Asn Thr Asn Arg Trp Leu Arg Val Val Ala His
            660                 665                 670

Arg Glu Gln Arg Glu Gly Ser Leu Gln Val Gly Asn Glu Ala Pro Val
        675                 680                 685

Thr Gly Ser Ser Pro Leu Gly Ala Thr Gln Leu Asp Thr Asp Gly Ala
690                 695                 700

Leu Trp Leu Gly Gly Leu Pro Glu Leu Pro Val Gly Pro Ala Leu Pro
705                 710                 715                 720

Lys Ala Tyr Gly Thr Gly Phe Val Gly Cys Leu Arg Asp Val Val Val
                725                 730                 735

Gly Arg His Pro Leu His Leu Leu Glu Asp Ala Val Thr Lys Pro Glu

```
                    740                 745                 750
Leu Arg Pro Cys Pro Thr Pro
            755

<210> SEQ ID NO 13
<211> LENGTH: 520
<212> TYPE: PRT
<213> ORGANISM: homo sapien

<400> SEQUENCE: 13

Met Ala Thr Gly Ser Arg Thr Ser Leu Leu Ala Phe Gly Leu Leu
 1               5                  10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Pro Gly Gly Pro Arg Thr
    210                 215                 220

Leu Cys Gly Ala Glu Leu Val Asp Ala Leu Gln Phe Val Cys Gly Asp
225                 230                 235                 240

Arg Gly Phe Tyr Phe Asn Lys Pro Thr Gly Tyr Gly Ser Ser Ser Arg
                245                 250                 255

Arg Ala Pro Gln Thr Gly Ile Val Asp Glu Cys Cys Phe Arg Ser Cys
            260                 265                 270

Asp Leu Arg Arg Leu Glu Met Tyr Cys Ala Pro Leu Lys Pro Ala Lys
        275                 280                 285

Ser Ala Gly Thr Gly Asp Lys Thr His Thr Cys Pro Pro Cys Pro Ala
    290                 295                 300

Pro Glu Leu Leu Gly Gly Pro Ser Val Phe Leu Phe Pro Pro Lys Pro
305                 310                 315                 320

Lys Asp Thr Leu Met Ile Ser Arg Thr Pro Glu Val Thr Cys Val Val
                325                 330                 335

Val Asp Val Ser His Glu Asp Pro Glu Val Lys Phe Asn Trp Tyr Val
            340                 345                 350
```

```
Asp Gly Val Glu Val His Asn Ala Lys Thr Lys Pro Arg Glu Glu Gln
            355                 360                 365

Tyr Asn Ser Thr Tyr Arg Val Val Ser Val Leu Thr Val Leu His Gln
        370                 375                 380

Asp Trp Leu Asn Gly Lys Glu Tyr Lys Cys Lys Val Ser Asn Lys Ala
385                 390                 395                 400

Leu Pro Ala Pro Ile Glu Lys Thr Ile Ser Lys Ala Lys Gly Gln Pro
                405                 410                 415

Arg Glu Pro Gln Val Tyr Thr Leu Pro Pro Ser Arg Asp Glu Leu Thr
            420                 425                 430

Lys Asn Gln Val Ser Leu Thr Cys Leu Val Lys Gly Phe Tyr Pro Ser
        435                 440                 445

Asp Ile Ala Val Glu Trp Glu Ser Asn Gly Gln Pro Glu Asn Asn Tyr
450                 455                 460

Lys Thr Thr Pro Pro Val Leu Asp Ser Asp Gly Ser Phe Phe Leu Tyr
465                 470                 475                 480

Ser Lys Leu Thr Val Asp Lys Ser Arg Trp Gln Gln Gly Asn Val Phe
                485                 490                 495

Ser Cys Ser Val Met His Glu Ala Leu His Asn His Tyr Thr Gln Lys
            500                 505                 510

Ser Leu Ser Leu Ser Pro Gly Lys
        515                 520

<210> SEQ ID NO 14
<211> LENGTH: 293
<212> TYPE: PRT
<213> ORGANISM: homo sapien

<400> SEQUENCE: 14

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205
```

```
Arg Ser Val Glu Gly Ser Cys Gly Phe Gly Pro Gly Pro Arg Thr
    210                 215                 220

Leu Cys Gly Ala Glu Leu Val Asp Ala Leu Gln Phe Val Cys Gly Asp
225                 230                 235                 240

Arg Gly Phe Tyr Phe Asn Lys Pro Thr Gly Tyr Gly Ser Ser Ser Arg
                245                 250                 255

Arg Ala Pro Gln Thr Gly Ile Val Asp Glu Cys Cys Phe Arg Ser Cys
            260                 265                 270

Asp Leu Arg Arg Leu Glu Met Tyr Cys Ala Pro Leu Lys Pro Ala Lys
        275                 280                 285

Ser Ala Gly Thr Gly
        290

<210> SEQ ID NO 15
<211> LENGTH: 756
<212> TYPE: PRT
<213> ORGANISM: homo sapien

<400> SEQUENCE: 15

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Pro Gly Ala Tyr Arg Pro
    210                 215                 220

Ser Glu Thr Leu Cys Gly Gly Glu Leu Val Asp Thr Leu Gln Phe Val
225                 230                 235                 240

Cys Gly Asp Arg Gly Phe Tyr Phe Ser Arg Pro Ala Ser Arg Val Ser
                245                 250                 255

Arg Arg Ser Arg Gly Ile Val Glu Glu Cys Cys Phe Arg Ser Cys Asp
            260                 265                 270

Leu Ala Leu Leu Glu Thr Tyr Cys Ala Thr Pro Ala Lys Ser Ala Gly
```

```
                    275                 280                 285
Thr Gly Gly Lys Ser Pro Cys Gln Pro Asn Pro Cys His Gly Ala Ala
    290                 295                 300

Pro Cys Arg Val Leu Pro Glu Gly Gly Ala Gln Cys Glu Cys Pro Leu
305                 310                 315                 320

Gly Arg Glu Gly Thr Phe Cys Gln Thr Ala Ser Gly Gln Asp Gly Ser
                325                 330                 335

Gly Pro Phe Leu Ala Asp Phe Asn Gly Phe Ser His Leu Glu Leu Arg
            340                 345                 350

Gly Leu His Thr Phe Ala Arg Asp Leu Gly Glu Lys Met Ala Leu Glu
        355                 360                 365

Val Val Phe Leu Ala Arg Gly Pro Ser Gly Leu Leu Leu Tyr Asn Gly
    370                 375                 380

Gln Lys Thr Asp Gly Lys Gly Asp Phe Val Ser Leu Ala Leu Arg Asp
385                 390                 395                 400

Arg Arg Leu Glu Phe Arg Tyr Asp Leu Gly Lys Gly Ala Ala Val Ile
                405                 410                 415

Arg Ser Arg Glu Pro Val Thr Leu Gly Ala Trp Thr Arg Val Ser Leu
            420                 425                 430

Glu Arg Asn Gly Arg Lys Gly Ala Leu Arg Val Gly Asp Gly Pro Arg
        435                 440                 445

Val Leu Gly Glu Ser Pro Val Pro His Thr Val Leu Asn Leu Lys Glu
    450                 455                 460

Pro Leu Tyr Val Gly Gly Ala Pro Asp Phe Ser Lys Leu Ala Arg Ala
465                 470                 475                 480

Ala Ala Val Ser Ser Gly Phe Asp Gly Ala Ile Gln Leu Val Ser Leu
                485                 490                 495

Gly Gly Arg Gln Leu Leu Thr Pro Glu His Val Leu Arg Gln Val Asp
            500                 505                 510

Val Thr Ser Phe Ala Gly His Pro Cys Thr Arg Ala Ser Gly His Pro
        515                 520                 525

Cys Leu Asn Gly Ala Ser Cys Val Pro Arg Glu Ala Ala Tyr Val Cys
    530                 535                 540

Leu Cys Pro Gly Gly Phe Ser Gly Pro His Cys Glu Lys Gly Leu Val
545                 550                 555                 560

Glu Lys Ser Ala Gly Asp Val Asp Thr Leu Ala Phe Asp Gly Arg Thr
                565                 570                 575

Phe Val Glu Tyr Leu Asn Ala Val Thr Glu Ser Glu Leu Ala Asn Glu
            580                 585                 590

Ile Pro Val Glu Lys Ala Leu Gln Ser Asn His Phe Glu Leu Ser Leu
        595                 600                 605

Arg Thr Glu Ala Thr Gln Gly Leu Val Leu Trp Ser Gly Lys Ala Thr
    610                 615                 620

Glu Arg Ala Asp Tyr Val Ala Leu Ala Ile Val Asp Gly His Leu Gln
625                 630                 635                 640

Leu Ser Tyr Asn Leu Gly Ser Gln Pro Val Val Leu Arg Ser Thr Val
                645                 650                 655

Pro Val Asn Thr Asn Arg Trp Leu Arg Val Val Ala His Arg Glu Gln
            660                 665                 670

Arg Glu Gly Ser Leu Gln Val Gly Asn Glu Ala Pro Val Thr Gly Ser
        675                 680                 685

Ser Pro Leu Gly Ala Thr Gln Leu Asp Thr Asp Gly Ala Leu Trp Leu
    690                 695                 700
```

```
Gly Gly Leu Pro Glu Leu Pro Val Gly Pro Ala Leu Pro Lys Ala Tyr
705                 710                 715                 720

Gly Thr Gly Phe Val Gly Cys Leu Arg Asp Val Val Gly Arg His
            725                 730                 735

Pro Leu His Leu Leu Glu Asp Ala Val Thr Lys Pro Glu Leu Arg Pro
        740                 745                 750

Cys Pro Thr Pro
        755

<210> SEQ ID NO 16
<211> LENGTH: 517
<212> TYPE: PRT
<213> ORGANISM: homo sapien

<400> SEQUENCE: 16

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Pro Gly Ala Tyr Arg Pro
    210                 215                 220

Ser Glu Thr Leu Cys Gly Gly Glu Leu Val Asp Thr Leu Gln Phe Val
225                 230                 235                 240

Cys Gly Asp Arg Gly Phe Tyr Phe Ser Arg Pro Ala Ser Arg Val Ser
                245                 250                 255

Arg Arg Ser Arg Gly Ile Val Glu Glu Cys Cys Phe Arg Ser Cys Asp
            260                 265                 270

Leu Ala Leu Leu Glu Thr Tyr Cys Ala Thr Pro Ala Lys Ser Ala Gly
        275                 280                 285

Thr Gly Asp Lys Thr His Thr Cys Pro Pro Cys Pro Ala Pro Glu Leu
    290                 295                 300

Leu Gly Gly Pro Ser Val Phe Leu Phe Pro Pro Lys Pro Lys Asp Thr
```

-continued

```
                305                 310                 315                 320

Leu Met Ile Ser Arg Thr Pro Glu Val Thr Cys Val Val Asp Val
                325                 330                 335

Ser His Glu Asp Pro Glu Val Lys Phe Asn Trp Tyr Val Asp Gly Val
                340                 345                 350

Glu Val His Asn Ala Lys Thr Lys Pro Arg Glu Glu Gln Tyr Asn Ser
                355                 360                 365

Thr Tyr Arg Val Val Ser Val Leu Thr Val Leu His Gln Asp Trp Leu
            370                 375                 380

Asn Gly Lys Glu Tyr Lys Cys Lys Val Ser Asn Lys Ala Leu Pro Ala
385                 390                 395                 400

Pro Ile Glu Lys Thr Ile Ser Lys Ala Lys Gly Gln Pro Arg Glu Pro
                405                 410                 415

Gln Val Tyr Thr Leu Pro Pro Ser Arg Asp Glu Leu Thr Lys Asn Gln
                420                 425                 430

Val Ser Leu Thr Cys Leu Val Lys Gly Phe Tyr Pro Ser Asp Ile Ala
                435                 440                 445

Val Glu Trp Glu Ser Asn Gly Gln Pro Glu Asn Asn Tyr Lys Thr Thr
            450                 455                 460

Pro Pro Val Leu Asp Ser Asp Gly Ser Phe Phe Leu Tyr Ser Lys Leu
465                 470                 475                 480

Thr Val Asp Lys Ser Arg Trp Gln Gln Gly Asn Val Phe Ser Cys Ser
                485                 490                 495

Val Met His Glu Ala Leu His Asn His Tyr Thr Gln Lys Ser Leu Ser
                500                 505                 510

Leu Ser Pro Gly Lys
            515

<210> SEQ ID NO 17
<211> LENGTH: 287
<212> TYPE: PRT
<213> ORGANISM: homo sapien

<400> SEQUENCE: 17

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160
```

```
Thr Gly Gln Ile Phe Lys Gln Thr Tyr Ser Lys Phe Asp Thr Asn Ser
            165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
            195                 200                 205

Arg Ser Val Glu Gly Ser Cys Gly Phe Gly Pro Gly Ala Tyr Arg Pro
210                 215                 220

Ser Glu Thr Leu Cys Gly Gly Glu Leu Val Asp Thr Leu Gln Phe Val
225                 230                 235                 240

Cys Gly Asp Arg Gly Phe Tyr Phe Ser Arg Pro Ala Ser Arg Val Ser
                245                 250                 255

Arg Arg Ser Arg Gly Ile Val Glu Glu Cys Cys Phe Arg Ser Cys Asp
            260                 265                 270

Leu Ala Leu Leu Glu Thr Tyr Cys Ala Thr Pro Ala Lys Ser Ala
            275                 280                 285

<210> SEQ ID NO 18
<211> LENGTH: 290
<212> TYPE: PRT
<213> ORGANISM: homo sapien

<400> SEQUENCE: 18

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Pro Gly Pro Glu Thr
    210                 215                 220

Leu Cys Gly Ala Glu Leu Val Asp Ala Leu Gln Phe Val Cys Gly Asp
225                 230                 235                 240

Arg Gly Phe Tyr Phe Asn Lys Pro Thr Gly Tyr Gly Ser Ser Ser Arg
                245                 250                 255
```

```
Arg Ala Pro Gln Thr Gly Ile Val Asp Glu Cys Cys Phe Arg Ser Cys
            260                 265                 270

Asp Leu Arg Arg Leu Glu Met Tyr Cys Ala Pro Leu Lys Pro Ala Lys
            275                 280                 285

Ser Ala
    290

<210> SEQ ID NO 19
<211> LENGTH: 289
<212> TYPE: PRT
<213> ORGANISM: homo sapien

<400> SEQUENCE: 19

Met Ala Thr Gly Ser Arg Thr Ser Leu Leu Leu Ala Phe Gly Leu Leu
  1               5                  10                  15

Cys Leu Pro Trp Leu Gln Glu Gly Ser Ala Phe Pro Thr Ile Pro Leu
             20                  25                  30

Ser Arg Leu Phe Asp Asn Ala Met Leu Arg Ala His Arg Leu His Gln
         35                  40                  45

Leu Ala Phe Asp Thr Tyr Gln Glu Phe Glu Glu Ala Tyr Ile Pro Lys
     50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
            115                 120                 125

Tyr Gly Ala Ser Asp Ser Asn Val Tyr Asp Leu Leu Lys Asp Leu Glu
130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
            195                 200                 205

Arg Ser Val Glu Gly Ser Cys Gly Phe Thr Gly Gly Pro Glu Thr Leu
        210                 215                 220

Cys Gly Ala Glu Leu Val Asp Ala Leu Gln Phe Val Cys Gly Asp Arg
225                 230                 235                 240

Gly Phe Tyr Phe Asn Lys Pro Thr Gly Tyr Gly Ser Ser Arg Ala
                245                 250                 255

Ala Pro Gln Thr Gly Ile Val Asp Glu Cys Cys Phe Arg Ser Cys Asp
            260                 265                 270

Leu Arg Arg Leu Glu Met Tyr Cys Ala Pro Leu Lys Pro Ala Lys Ser
            275                 280                 285

Ala

<210> SEQ ID NO 20
<211> LENGTH: 288
<212> TYPE: PRT
<213> ORGANISM: homo sapien
```

<400> SEQUENCE: 20

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Thr Gly Gly Pro Glu Thr Leu
    210                 215                 220

Cys Gly Ala Glu Leu Val Asp Ala Leu Gln Phe Val Cys Gly Asp Arg
225                 230                 235                 240

Gly Phe Tyr Phe Asn Lys Pro Thr Gly Tyr Gly Ser Ser Ser Arg Ala
                245                 250                 255

Pro Gln Thr Gly Ile Val Asp Glu Cys Cys Phe Arg Ser Cys Asp Leu
            260                 265                 270

Arg Arg Leu Glu Met Tyr Cys Ala Pro Leu Lys Pro Ala Lys Ser Ala
        275                 280                 285
```

<210> SEQ ID NO 21
<211> LENGTH: 289
<212> TYPE: PRT
<213> ORGANISM: homo sapien

<400> SEQUENCE: 21

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80
```

```
Ser Glu Ser Ile Pro Thr Pro Ser Asn Arg Glu Glu Thr Gln Gln Lys
            85                  90                  95

Ser Asn Leu Glu Leu Leu Arg Ile Ser Leu Leu Leu Ile Gln Ser Trp
        100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
        130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Thr Gly Gly Pro Arg Thr Leu
    210                 215                 220

Cys Gly Ala Glu Leu Val Asp Ala Leu Gln Phe Val Cys Gly Asp Arg
225                 230                 235                 240

Gly Phe Tyr Phe Asn Lys Pro Thr Gly Tyr Gly Ser Ser Ser Arg Ala
                245                 250                 255

Ala Pro Gln Thr Gly Ile Val Asp Glu Cys Cys Phe Arg Ser Cys Asp
            260                 265                 270

Leu Arg Arg Leu Glu Met Tyr Cys Ala Pro Leu Lys Pro Ala Lys Ser
        275                 280                 285

Ala

<210> SEQ ID NO 22
<211> LENGTH: 288
<212> TYPE: PRT
<213> ORGANISM: homo sapien

<400> SEQUENCE: 22

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
            85                  90                  95

Ser Asn Leu Glu Leu Leu Arg Ile Ser Leu Leu Leu Ile Gln Ser Trp
        100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
        130                 135                 140

Glu Gly Ile Gln Thr Leu Met Gly Arg Leu Glu Asp Gly Ser Pro Arg
145                 150                 155                 160
```

```
Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Thr Gly Pro Arg Thr Leu
    210                 215                 220

Cys Gly Ala Glu Leu Val Asp Ala Leu Gln Phe Val Cys Gly Asp Arg
225                 230                 235                 240

Gly Phe Tyr Phe Asn Lys Pro Thr Gly Tyr Gly Ser Ser Ser Arg Ala
                245                 250                 255

Pro Gln Thr Gly Ile Val Asp Glu Cys Cys Phe Arg Ser Cys Asp Leu
            260                 265                 270

Arg Arg Leu Glu Met Tyr Cys Ala Pro Leu Lys Pro Ala Lys Ser Ala
        275                 280                 285

<210> SEQ ID NO 23
<211> LENGTH: 288
<212> TYPE: PRT
<213> ORGANISM: homo sapien

<400> SEQUENCE: 23

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Thr Gly Pro Glu Thr Leu
    210                 215                 220

Cys Gly Ala Glu Leu Val Asp Ala Leu Gln Phe Val Cys Gly Asp Arg
225                 230                 235                 240

Gly Phe Tyr Phe Asn Lys Pro Thr Gly Tyr Gly Ser Ser Ser Arg Ala
```

```
                    245                 250                 255
Pro Gln Thr Gly Ile Val Asp Glu Cys Cys Phe Arg Ser Cys Asp Leu
            260                 265                 270

Arg Arg Leu Glu Met Tyr Cys Ala Pro Leu Lys Pro Ala Lys Ser Ala
        275                 280                 285

<210> SEQ ID NO 24
<211> LENGTH: 287
<212> TYPE: PRT
<213> ORGANISM: homo sapien

<400> SEQUENCE: 24

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Pro Gly Thr Leu Cys Gly
    210                 215                 220

Ala Glu Leu Val Asp Ala Leu Gln Phe Val Cys Gly Asp Arg Gly Phe
225                 230                 235                 240

Tyr Phe Asn Lys Pro Thr Gly Tyr Gly Ser Ser Arg Arg Ala Pro
                245                 250                 255

Gln Thr Gly Ile Val Asp Glu Cys Cys Phe Arg Ser Cys Asp Leu Arg
            260                 265                 270

Arg Leu Glu Met Tyr Cys Ala Pro Leu Lys Pro Ala Lys Ser Ala
        275                 280                 285

<210> SEQ ID NO 25
<211> LENGTH: 286
<212> TYPE: PRT
<213> ORGANISM: homo sapien

<400> SEQUENCE: 25

Met Ala Thr Gly Ser Arg Thr Ser Leu Leu Leu Ala Phe Gly Leu Leu
```

```
            1               5                  10                 15
Cys Leu Pro Trp Leu Gln Glu Gly Ser Ala Phe Pro Thr Ile Pro Leu
                20                  25                 30

Ser Arg Leu Phe Asp Asn Ala Met Leu Arg Ala His Arg Leu His Gln
                35                  40                 45

Leu Ala Phe Asp Thr Tyr Gln Glu Phe Glu Glu Ala Tyr Ile Pro Lys
                50                  55                 60

Glu Gln Lys Tyr Ser Phe Leu Gln Asn Pro Gln Thr Ser Leu Cys Phe
 65                  70                 75                  80

Ser Glu Ser Ile Pro Thr Pro Ser Asn Arg Glu Glu Thr Gln Gln Lys
                85                  90                 95

Ser Asn Leu Glu Leu Leu Arg Ile Ser Leu Leu Leu Ile Gln Ser Trp
                100                 105                110

Leu Glu Pro Val Gln Phe Leu Arg Ser Val Phe Ala Asn Ser Leu Val
                115                 120                125

Tyr Gly Ala Ser Asp Ser Asn Val Tyr Asp Leu Leu Lys Asp Leu Glu
                130                 135                140

Glu Gly Ile Gln Thr Leu Met Gly Arg Leu Glu Asp Gly Ser Pro Arg
145                 150                 155                160

Thr Gly Gln Ile Phe Lys Gln Thr Tyr Ser Lys Phe Asp Thr Asn Ser
                165                 170                175

His Asn Asp Asp Ala Leu Leu Lys Asn Tyr Gly Leu Leu Tyr Cys Phe
                180                 185                190

Arg Lys Asp Met Asp Lys Val Glu Thr Phe Leu Arg Ile Val Gln Cys
                195                 200                205

Arg Ser Val Glu Gly Ser Cys Gly Phe Gly Pro Gly Thr Leu Cys Gly
                210                 215                220

Ala Glu Leu Val Asp Ala Leu Gln Phe Val Cys Gly Asp Arg Gly Phe
225                 230                 235                240

Tyr Phe Asn Lys Pro Thr Gly Tyr Gly Ser Ser Ser Arg Ala Pro Gln
                245                 250                255

Thr Gly Ile Val Asp Glu Cys Cys Phe Arg Ser Cys Asp Leu Arg Arg
                260                 265                270

Leu Glu Met Tyr Cys Ala Pro Leu Lys Pro Ala Lys Ser Ala
                275                 280                285

<210> SEQ ID NO 26
<211> LENGTH: 759
<212> TYPE: PRT
<213> ORGANISM: homo sapien

<400> SEQUENCE: 26

Met Ala Thr Gly Ser Arg Thr Ser Leu Leu Leu Ala Phe Gly Leu Leu
 1               5                  10                 15

Cys Leu Pro Trp Leu Gln Glu Gly Ser Ala Phe Pro Thr Ile Pro Leu
                20                  25                 30

Ser Arg Leu Phe Asp Asn Ala Met Leu Arg Ala His Arg Leu His Gln
                35                  40                 45

Leu Ala Phe Asp Thr Tyr Gln Glu Phe Glu Glu Ala Tyr Ile Pro Lys
                50                  55                 60

Glu Gln Lys Tyr Ser Phe Leu Gln Asn Pro Gln Thr Ser Leu Cys Phe
 65                  70                 75                  80

Ser Glu Ser Ile Pro Thr Pro Ser Asn Arg Glu Glu Thr Gln Gln Lys
                85                  90                 95
```

-continued

```
Ser Asn Leu Glu Leu Leu Arg Ile Ser Leu Leu Ile Gln Ser Trp
            100                 105                 110

Leu Glu Pro Val Gln Phe Leu Arg Ser Val Phe Ala Asn Ser Leu Val
            115                 120                 125

Tyr Gly Ala Ser Asp Ser Asn Val Tyr Asp Leu Leu Lys Asp Leu Glu
            130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
            195                 200                 205

Arg Ser Val Glu Gly Ser Cys Gly Phe Gly Pro Gly Gly Pro Glu Thr
            210                 215                 220

Leu Cys Gly Ala Glu Leu Val Asp Ala Leu Gln Phe Val Cys Gly Asp
225                 230                 235                 240

Arg Gly Phe Tyr Phe Asn Lys Pro Thr Gly Tyr Gly Ser Ser Ser Arg
                245                 250                 255

Arg Ala Pro Gln Thr Gly Ile Val Asp Glu Cys Cys Phe Arg Ser Cys
            260                 265                 270

Asp Leu Arg Arg Leu Glu Met Tyr Cys Ala Pro Leu Lys Pro Ala Lys
            275                 280                 285

Ser Ala Gly Thr Gly Lys Ser Pro Cys Gln Pro Asn Pro Cys His
            290                 295                 300

Gly Ala Ala Pro Cys Arg Val Leu Pro Glu Gly Gly Ala Gln Cys Glu
305                 310                 315                 320

Cys Pro Leu Gly Arg Glu Gly Thr Phe Cys Gln Thr Ala Ser Gly Gln
            325                 330                 335

Asp Gly Ser Gly Pro Phe Leu Ala Asp Phe Asn Gly Phe Ser His Leu
            340                 345                 350

Glu Leu Arg Gly Leu His Thr Phe Ala Arg Asp Leu Gly Glu Lys Met
            355                 360                 365

Ala Leu Glu Val Val Phe Leu Ala Arg Gly Pro Ser Gly Leu Leu Leu
            370                 375                 380

Tyr Asn Gly Gln Lys Thr Asp Gly Lys Gly Asp Phe Val Ser Leu Ala
385                 390                 395                 400

Leu Arg Asp Arg Arg Leu Glu Phe Arg Tyr Asp Leu Gly Lys Gly Ala
                405                 410                 415

Ala Val Ile Arg Ser Arg Glu Pro Val Thr Leu Gly Ala Trp Thr Arg
            420                 425                 430

Val Ser Leu Glu Arg Asn Gly Arg Lys Gly Ala Leu Arg Val Gly Asp
            435                 440                 445

Gly Pro Arg Val Leu Gly Glu Ser Pro Val Pro His Thr Val Leu Asn
450                 455                 460

Leu Lys Glu Pro Leu Tyr Val Gly Gly Ala Pro Asp Phe Ser Lys Leu
465                 470                 475                 480

Ala Arg Ala Ala Ala Val Ser Ser Gly Phe Asp Gly Ala Ile Gln Leu
                485                 490                 495

Val Ser Leu Gly Gly Arg Gln Leu Leu Thr Pro Glu His Val Leu Arg
            500                 505                 510

Gln Val Asp Val Thr Ser Phe Ala Gly His Pro Cys Thr Arg Ala Ser
```

-continued

```
                515                 520                 525
Gly His Pro Cys Leu Asn Gly Ala Ser Cys Val Pro Arg Glu Ala Ala
        530                 535                 540

Tyr Val Cys Leu Cys Pro Gly Phe Ser Gly Pro His Cys Glu Lys
545                 550                 555                 560

Gly Leu Val Glu Lys Ser Ala Gly Asp Val Asp Thr Leu Ala Phe Asp
                565                 570                 575

Gly Arg Thr Phe Val Glu Tyr Leu Asn Ala Val Thr Glu Ser Glu Leu
            580                 585                 590

Ala Asn Glu Ile Pro Val Glu Lys Ala Leu Gln Ser Asn His Phe Glu
        595                 600                 605

Leu Ser Leu Arg Thr Glu Ala Thr Gln Gly Leu Val Leu Trp Ser Gly
    610                 615                 620

Lys Ala Thr Glu Arg Ala Asp Tyr Val Ala Leu Ala Ile Val Asp Gly
625                 630                 635                 640

His Leu Gln Leu Ser Tyr Asn Leu Gly Ser Gln Pro Val Val Leu Arg
                645                 650                 655

Ser Thr Val Pro Val Asn Thr Asn Arg Trp Leu Arg Val Ala His
            660                 665                 670

Arg Glu Gln Arg Glu Gly Ser Leu Gln Val Gly Asn Glu Ala Pro Val
        675                 680                 685

Thr Gly Ser Ser Pro Leu Gly Ala Thr Gln Leu Asp Thr Asp Gly Ala
    690                 695                 700

Leu Trp Leu Gly Gly Leu Pro Glu Leu Pro Val Gly Pro Ala Leu Pro
705                 710                 715                 720

Lys Ala Tyr Gly Thr Gly Phe Val Gly Cys Leu Arg Asp Val Val Val
                725                 730                 735

Gly Arg His Pro Leu His Leu Leu Glu Asp Ala Val Thr Lys Pro Glu
            740                 745                 750

Leu Arg Pro Cys Pro Thr Pro
            755

<210> SEQ ID NO 27
<211> LENGTH: 756
<212> TYPE: PRT
<213> ORGANISM: homo sapien

<400> SEQUENCE: 27

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125
```

-continued

```
Tyr Gly Ala Ser Asp Ser Asn Val Tyr Asp Leu Leu Lys Asp Leu Glu
            130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
            195                 200                 205

Arg Ser Val Glu Gly Ser Cys Gly Phe Gly Pro Gly Thr Leu Cys Gly
            210                 215                 220

Ala Glu Leu Val Asp Ala Leu Gln Phe Val Cys Gly Asp Arg Gly Phe
225                 230                 235                 240

Tyr Phe Asn Lys Pro Thr Gly Tyr Gly Ser Ser Ser Arg Arg Ala Pro
                245                 250                 255

Gln Thr Gly Ile Val Asp Glu Cys Cys Phe Arg Ser Cys Asp Leu Arg
            260                 265                 270

Arg Leu Glu Met Tyr Cys Ala Pro Leu Lys Pro Ala Lys Ser Ala Gly
            275                 280                 285

Thr Gly Gly Lys Ser Pro Cys Gln Pro Asn Pro Cys His Gly Ala Ala
            290                 295                 300

Pro Cys Arg Val Leu Pro Glu Gly Gly Ala Gln Cys Glu Cys Pro Leu
305                 310                 315                 320

Gly Arg Glu Gly Thr Phe Cys Gln Thr Ala Ser Gly Gln Asp Gly Ser
                325                 330                 335

Gly Pro Phe Leu Ala Asp Phe Asn Gly Phe Ser His Leu Glu Leu Arg
            340                 345                 350

Gly Leu His Thr Phe Ala Arg Asp Leu Gly Glu Lys Met Ala Leu Glu
            355                 360                 365

Val Val Phe Leu Ala Arg Gly Pro Ser Gly Leu Leu Leu Tyr Asn Gly
            370                 375                 380

Gln Lys Thr Asp Gly Lys Gly Asp Phe Val Ser Leu Ala Leu Arg Asp
385                 390                 395                 400

Arg Arg Leu Glu Phe Arg Tyr Asp Leu Gly Lys Gly Ala Ala Val Ile
                405                 410                 415

Arg Ser Arg Glu Pro Val Thr Leu Gly Ala Trp Thr Arg Val Ser Leu
            420                 425                 430

Glu Arg Asn Gly Arg Lys Gly Ala Leu Arg Val Gly Asp Gly Pro Arg
            435                 440                 445

Val Leu Gly Glu Ser Pro Val Pro His Thr Val Leu Asn Leu Lys Glu
450                 455                 460

Pro Leu Tyr Val Gly Gly Ala Pro Asp Phe Ser Lys Leu Ala Arg Ala
465                 470                 475                 480

Ala Ala Val Ser Ser Gly Phe Asp Gly Ala Ile Gln Leu Val Ser Leu
                485                 490                 495

Gly Gly Arg Gln Leu Leu Thr Pro Glu His Val Leu Arg Gln Val Asp
            500                 505                 510

Val Thr Ser Phe Ala Gly His Pro Cys Thr Arg Ala Ser Gly His Pro
            515                 520                 525

Cys Leu Asn Gly Ala Ser Cys Val Pro Arg Glu Ala Ala Tyr Val Cys
530                 535                 540

Leu Cys Pro Gly Gly Phe Ser Gly Pro His Cys Glu Lys Gly Leu Val
```

-continued

```
                545                 550                 555                 560
Glu Lys Ser Ala Gly Asp Val Asp Thr Leu Ala Phe Asp Gly Arg Thr
                565                 570                 575

Phe Val Glu Tyr Leu Asn Ala Val Thr Glu Ser Glu Leu Ala Asn Glu
                580                 585                 590

Ile Pro Val Glu Lys Ala Leu Gln Ser Asn His Phe Glu Leu Ser Leu
                595                 600                 605

Arg Thr Glu Ala Thr Gln Gly Leu Val Leu Trp Ser Gly Lys Ala Thr
                610                 615                 620

Glu Arg Ala Asp Tyr Val Ala Leu Ala Ile Val Asp Gly His Leu Gln
625                 630                 635                 640

Leu Ser Tyr Asn Leu Gly Ser Gln Pro Val Val Leu Arg Ser Thr Val
                645                 650                 655

Pro Val Asn Thr Asn Arg Trp Leu Arg Val Val Ala His Arg Glu Gln
                660                 665                 670

Arg Glu Gly Ser Leu Gln Val Gly Asn Glu Ala Pro Val Thr Gly Ser
                675                 680                 685

Ser Pro Leu Gly Ala Thr Gln Leu Asp Thr Asp Gly Ala Leu Trp Leu
                690                 695                 700

Gly Gly Leu Pro Glu Leu Pro Val Gly Pro Ala Leu Pro Lys Ala Tyr
705                 710                 715                 720

Gly Thr Gly Phe Val Gly Cys Leu Arg Asp Val Val Gly Arg His
                725                 730                 735

Pro Leu His Leu Leu Glu Asp Ala Val Thr Lys Pro Glu Leu Arg Pro
                740                 745                 750

Cys Pro Thr Pro
            755

<210> SEQ ID NO 28
<211> LENGTH: 758
<212> TYPE: PRT
<213> ORGANISM: homo sapien

<400> SEQUENCE: 28

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160
```

```
Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Gly Pro Gly Gly Pro Glu Thr
    210                 215                 220

Leu Cys Gly Ala Glu Leu Val Asp Ala Leu Gln Phe Val Cys Gly Asp
225                 230                 235                 240

Arg Gly Phe Tyr Phe Asn Lys Pro Thr Gly Tyr Gly Ser Ser Ser Arg
                245                 250                 255

Ala Pro Gln Thr Gly Ile Val Asp Glu Cys Cys Phe Arg Ser Cys Asp
            260                 265                 270

Leu Arg Arg Leu Glu Met Tyr Cys Ala Pro Leu Lys Pro Ala Lys Ser
        275                 280                 285

Ala Gly Thr Gly Gly Lys Ser Pro Cys Gln Pro Asn Pro Cys His Gly
    290                 295                 300

Ala Ala Pro Cys Arg Val Leu Pro Glu Gly Gly Ala Gln Cys Glu Cys
305                 310                 315                 320

Pro Leu Gly Arg Glu Gly Thr Phe Cys Gln Thr Ala Ser Gly Gln Asp
                325                 330                 335

Gly Ser Gly Pro Phe Leu Ala Asp Phe Asn Gly Phe Ser His Leu Glu
            340                 345                 350

Leu Arg Gly Leu His Thr Phe Ala Arg Asp Leu Gly Glu Lys Met Ala
        355                 360                 365

Leu Glu Val Val Phe Leu Ala Arg Gly Pro Ser Gly Leu Leu Leu Tyr
    370                 375                 380

Asn Gly Gln Lys Thr Asp Gly Lys Gly Asp Phe Val Ser Leu Ala Leu
385                 390                 395                 400

Arg Asp Arg Arg Leu Glu Phe Arg Tyr Asp Leu Gly Lys Gly Ala Ala
                405                 410                 415

Val Ile Arg Ser Arg Glu Pro Val Thr Leu Gly Ala Trp Thr Arg Val
            420                 425                 430

Ser Leu Glu Arg Asn Gly Arg Lys Gly Ala Leu Arg Val Gly Asp Gly
        435                 440                 445

Pro Arg Val Leu Gly Glu Ser Pro Val Pro His Thr Val Leu Asn Leu
    450                 455                 460

Lys Glu Pro Leu Tyr Val Gly Gly Ala Pro Asp Phe Ser Lys Leu Ala
465                 470                 475                 480

Arg Ala Ala Ala Val Ser Ser Gly Phe Asp Gly Ala Ile Gln Leu Val
                485                 490                 495

Ser Leu Gly Gly Arg Gln Leu Leu Thr Pro Glu His Val Leu Arg Gln
            500                 505                 510

Val Asp Val Thr Ser Phe Ala Gly His Pro Cys Thr Arg Ala Ser Gly
        515                 520                 525

His Pro Cys Leu Asn Gly Ala Ser Cys Val Pro Arg Glu Ala Ala Tyr
    530                 535                 540

Val Cys Leu Cys Pro Gly Gly Phe Ser Gly Pro His Cys Glu Lys Gly
545                 550                 555                 560

Leu Val Glu Lys Ser Ala Gly Asp Val Asp Thr Leu Ala Phe Asp Gly
                565                 570                 575

Arg Thr Phe Val Glu Tyr Leu Asn Ala Val Thr Glu Ser Glu Leu Ala
```

-continued

```
                580             585             590
Asn Glu Ile Pro Val Glu Lys Ala Leu Gln Ser Asn His Phe Glu Leu
            595                 600                 605

Ser Leu Arg Thr Glu Ala Thr Gln Gly Leu Val Leu Trp Ser Gly Lys
        610                 615                 620

Ala Thr Glu Arg Ala Asp Tyr Val Ala Leu Ala Ile Val Asp Gly His
625                 630                 635                 640

Leu Gln Leu Ser Tyr Asn Leu Gly Ser Gln Pro Val Val Leu Arg Ser
                645                 650                 655

Thr Val Pro Val Asn Thr Asn Arg Trp Leu Arg Val Val Ala His Arg
            660                 665                 670

Glu Gln Arg Glu Gly Ser Leu Gln Val Gly Asn Glu Ala Pro Val Thr
        675                 680                 685

Gly Ser Ser Pro Leu Gly Ala Thr Gln Leu Asp Thr Asp Gly Ala Leu
    690                 695                 700

Trp Leu Gly Gly Leu Pro Glu Leu Pro Val Gly Pro Ala Leu Pro Lys
705                 710                 715                 720

Ala Tyr Gly Thr Gly Phe Val Gly Cys Leu Arg Asp Val Val Val Gly
                725                 730                 735

Arg His Pro Leu His Leu Leu Glu Asp Ala Val Thr Lys Pro Glu Leu
            740                 745                 750

Arg Pro Cys Pro Thr Pro
            755

<210> SEQ ID NO 29
<211> LENGTH: 759
<212> TYPE: PRT
<213> ORGANISM: homo sapien

<400> SEQUENCE: 29

Met Ala Thr Gly Ser Arg Thr Ser Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190
```

-continued

```
Arg Lys Asp Met Asp Lys Val Glu Thr Phe Leu Arg Ile Val Gln Cys
        195                 200                 205
Arg Ser Val Glu Gly Ser Cys Gly Phe Gly Pro Gly Gly Pro Glu Thr
    210                 215                 220
Leu Cys Gly Ala Glu Leu Val Asp Ala Leu Gln Phe Val Cys Gly Asp
225                 230                 235                 240
Arg Gly Phe Tyr Phe Asn Lys Pro Thr Gly Tyr Gly Ser Ser Ser Arg
                245                 250                 255
Ala Ala Pro Gln Thr Gly Ile Val Asp Glu Cys Cys Phe Arg Ser Cys
            260                 265                 270
Asp Leu Arg Arg Leu Glu Met Tyr Cys Ala Pro Leu Lys Pro Ala Lys
        275                 280                 285
Ser Ala Gly Thr Gly Gly Lys Ser Pro Cys Gln Pro Asn Pro Cys His
    290                 295                 300
Gly Ala Ala Pro Cys Arg Val Leu Pro Glu Gly Gly Ala Gln Cys Glu
305                 310                 315                 320
Cys Pro Leu Gly Arg Glu Gly Thr Phe Cys Gln Thr Ala Ser Gly Gln
                325                 330                 335
Asp Gly Ser Gly Pro Phe Leu Ala Asp Phe Asn Gly Phe Ser His Leu
            340                 345                 350
Glu Leu Arg Gly Leu His Thr Phe Ala Arg Asp Leu Gly Glu Lys Met
        355                 360                 365
Ala Leu Glu Val Val Phe Leu Ala Arg Gly Pro Ser Gly Leu Leu Leu
    370                 375                 380
Tyr Asn Gly Gln Lys Thr Asp Gly Lys Gly Asp Phe Val Ser Leu Ala
385                 390                 395                 400
Leu Arg Asp Arg Arg Leu Glu Phe Arg Tyr Asp Leu Gly Lys Gly Ala
                405                 410                 415
Ala Val Ile Arg Ser Arg Glu Pro Val Thr Leu Gly Ala Trp Thr Arg
            420                 425                 430
Val Ser Leu Glu Arg Asn Gly Arg Lys Gly Ala Leu Arg Val Gly Asp
        435                 440                 445
Gly Pro Arg Val Leu Gly Glu Ser Pro Val Pro His Thr Val Leu Asn
    450                 455                 460
Leu Lys Glu Pro Leu Tyr Val Gly Gly Ala Pro Asp Phe Ser Lys Leu
465                 470                 475                 480
Ala Arg Ala Ala Ala Val Ser Ser Gly Phe Asp Gly Ala Ile Gln Leu
                485                 490                 495
Val Ser Leu Gly Gly Arg Gln Leu Leu Thr Pro Glu His Val Leu Arg
            500                 505                 510
Gln Val Asp Val Thr Ser Phe Ala Gly His Pro Cys Thr Arg Ala Ser
        515                 520                 525
Gly His Pro Cys Leu Asn Gly Ala Ser Cys Val Pro Arg Glu Ala Ala
    530                 535                 540
Tyr Val Cys Leu Cys Pro Gly Phe Ser Gly Pro His Cys Glu Lys
545                 550                 555                 560
Gly Leu Val Glu Lys Ser Ala Gly Asp Val Asp Thr Leu Ala Phe Asp
                565                 570                 575
Gly Arg Thr Phe Val Glu Tyr Leu Asn Ala Val Thr Glu Ser Glu Leu
            580                 585                 590
Ala Asn Glu Ile Pro Val Glu Lys Ala Leu Gln Ser Asn His Phe Glu
        595                 600                 605
Leu Ser Leu Arg Thr Glu Ala Thr Gln Gly Leu Val Leu Trp Ser Gly
```

```
              610                 615                 620
Lys Ala Thr Glu Arg Ala Asp Tyr Val Ala Leu Ala Ile Val Asp Gly
625                 630                 635                 640

His Leu Gln Leu Ser Tyr Asn Leu Gly Ser Gln Pro Val Val Leu Arg
                645                 650                 655

Ser Thr Val Pro Val Asn Thr Asn Arg Trp Leu Arg Val Val Ala His
                660                 665                 670

Arg Glu Gln Arg Glu Gly Ser Leu Gln Val Gly Asn Glu Ala Pro Val
            675                 680                 685

Thr Gly Ser Ser Pro Leu Gly Ala Thr Gln Leu Asp Thr Asp Gly Ala
690                 695                 700

Leu Trp Leu Gly Gly Leu Pro Glu Leu Pro Val Gly Pro Ala Leu Pro
705                 710                 715                 720

Lys Ala Tyr Gly Thr Gly Phe Val Gly Cys Leu Arg Asp Val Val Val
                725                 730                 735

Gly Arg His Pro Leu His Leu Leu Glu Asp Ala Val Thr Lys Pro Glu
                740                 745                 750

Leu Arg Pro Cys Pro Thr Pro
            755

<210> SEQ ID NO 30
<211> LENGTH: 519
<212> TYPE: PRT
<213> ORGANISM: homo sapien

<400> SEQUENCE: 30

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Thr Gly Pro Asp Lys Thr
210                 215                 220
```

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Asp Glu Leu Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

Gly Gly Pro Glu Thr Leu Cys Gly Ala Glu Leu Val Asp Ala Leu Gln
450                 455                 460

Phe Val Cys Gly Asp Arg Gly Phe Tyr Phe Asn Lys Pro Thr Gly Tyr
465                 470                 475                 480

Gly Ser Ser Ser Arg Arg Ala Pro Gln Thr Gly Ile Val Asp Glu Cys
            485                 490                 495

Cys Phe Arg Ser Cys Asp Leu Arg Arg Leu Glu Met Tyr Cys Ala Pro
        500                 505                 510

Leu Lys Pro Ala Lys Ser Ala
        515

<210> SEQ ID NO 31
<211> LENGTH: 518
<212> TYPE: PRT
<213> ORGANISM: homo sapien

<400> SEQUENCE: 31

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

-continued

```
Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Thr Gly Gly Pro Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Gly Pro Glu Thr Leu Cys Gly Ala Glu Leu Val Asp Ala Leu Gln
    450                 455                 460

Phe Val Cys Gly Asp Arg Gly Phe Tyr Phe Asn Lys Pro Thr Gly Tyr
465                 470                 475                 480

Gly Ser Ser Ser Arg Ala Pro Gln Thr Gly Ile Val Asp Glu Cys Cys
                485                 490                 495
```

```
Phe Arg Ser Cys Asp Leu Arg Arg Leu Glu Met Tyr Cys Ala Pro Leu
                500                 505                 510

Lys Pro Ala Lys Ser Ala
            515

<210> SEQ ID NO 32
<211> LENGTH: 516
<212> TYPE: PRT
<213> ORGANISM: homo sapien

<400> SEQUENCE: 32

Met Ala Thr Gly Ser Arg Thr Ser Leu Leu Leu Ala Phe Gly Leu Leu
  1               5                  10                  15

Cys Leu Pro Trp Leu Gln Glu Gly Ser Ala Phe Pro Thr Ile Pro Leu
             20                  25                  30

Ser Arg Leu Phe Asp Asn Ala Met Leu Arg Ala His Arg Leu His Gln
         35                  40                  45

Leu Ala Phe Asp Thr Tyr Gln Glu Phe Glu Glu Ala Tyr Ile Pro Lys
     50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Thr Gly Gly Pro Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350
```

```
Pro Pro Ser Arg Asp Glu Leu Thr Lys Asn Gln Val Ser Leu Thr Cys
    355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

Gly Thr Leu Cys Gly Ala Glu Leu Val Asp Ala Leu Gln Phe Val Cys
    450                 455                 460

Gly Asp Arg Gly Phe Tyr Phe Asn Lys Pro Thr Gly Tyr Gly Ser Ser
465                 470                 475                 480

Ser Arg Arg Ala Pro Gln Thr Gly Ile Val Asp Glu Cys Cys Phe Arg
                485                 490                 495

Ser Cys Asp Leu Arg Arg Leu Glu Met Tyr Cys Ala Pro Leu Lys Pro
                500                 505                 510

Ala Lys Ser Ala
    515

<210> SEQ ID NO 33
<211> LENGTH: 515
<212> TYPE: PRT
<213> ORGANISM: homo sapien

<400> SEQUENCE: 33

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
```

-continued

```
                195                 200                 205
Arg Ser Val Glu Gly Ser Cys Gly Phe Thr Gly Gly Pro Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Thr Leu Cys Gly Ala Glu Leu Val Asp Ala Leu Gln Phe Val Cys
    450                 455                 460

Gly Asp Arg Gly Phe Tyr Phe Asn Lys Pro Thr Gly Tyr Gly Ser Ser
465                 470                 475                 480

Ser Arg Ala Pro Gln Thr Gly Ile Val Asp Glu Cys Cys Phe Arg Ser
                485                 490                 495

Cys Asp Leu Arg Arg Leu Glu Met Tyr Cys Ala Pro Leu Lys Pro Ala
            500                 505                 510

Lys Ser Ala
        515

<210> SEQ ID NO 34
<211> LENGTH: 224
<212> TYPE: PRT
<213> ORGANISM: homo sapien

<400> SEQUENCE: 34

Met Leu Pro Ser Leu Ile Gln Pro Cys Ser Trp Ile Leu Leu Leu Leu
1               5                   10                  15

Leu Val Asn Ser Ser Leu Leu Trp Lys Asn Val Ala Ser Phe Pro Met
            20                  25                  30

Cys Ala Met Arg Asn Gly Arg Cys Phe Met Ser Phe Glu Asp Thr Phe
        35                  40                  45
```

```
Glu Leu Ala Gly Ser Leu Ser His Asn Ile Ser Ile Glu Val Ser Glu
 50                  55                  60

Leu Phe Thr Glu Phe Glu Lys His Tyr Ser Asn Val Ser Gly Leu Arg
 65                  70                  75                  80

Asp Lys Ser Pro Met Arg Cys Asn Thr Ser Phe Leu Pro Thr Pro Glu
                 85                  90                  95

Asn Lys Glu Gln Ala Arg Leu Thr His Tyr Ser Ala Leu Leu Lys Ser
                100                 105                 110

Gly Ala Met Ile Leu Asp Ala Trp Glu Ser Pro Leu Asp Asp Leu Val
            115                 120                 125

Ser Glu Leu Ser Thr Ile Lys Asn Val Pro Asp Ile Ile Ser Lys
    130                 135                 140

Ala Thr Asp Ile Lys Lys Lys Ile Asn Ala Val Arg Asn Gly Val Asn
145                 150                 155                 160

Ala Leu Met Ser Thr Met Leu Gln Asn Gly Asp Glu Glu Lys Lys Asn
                165                 170                 175

Pro Ala Trp Phe Leu Gln Ser Asp Asn Glu Asp Ala Arg Ile His Ser
            180                 185                 190

Leu Tyr Gly Met Ile Ser Cys Leu Asp Asn Asp Phe Lys Lys Val Asp
            195                 200                 205

Ile Tyr Leu Asn Val Leu Lys Cys Tyr Met Leu Lys Ile Asp Asn Cys
210                 215                 220

<210> SEQ ID NO 35
<211> LENGTH: 690
<212> TYPE: PRT
<213> ORGANISM: homo sapien

<400> SEQUENCE: 35

Met Gly Lys Ile Ser Ser Leu Pro Thr Gln Leu Phe Lys Cys Cys Phe
  1               5                  10                  15

Cys Asp Phe Leu Lys Val Lys Met His Thr Met Ser Ser Ser His Leu
                 20                  25                  30

Phe Tyr Leu Ala Leu Cys Leu Leu Thr Phe Thr Ser Ser Ala Thr Ala
             35                  40                  45

Gly Pro Arg Thr Leu Cys Gly Ala Glu Leu Val Asp Ala Leu Gln Phe
 50                  55                  60

Val Cys Gly Arg Gly Phe Tyr Phe Asn Lys Pro Thr Gly Tyr Gly Ser
 65                  70                  75                  80

Ser Ser Arg Arg Ala Pro Gln Thr Gly Ile Val Asp Glu Cys Cys Phe
                 85                  90                  95

Arg Ser Cys Asp Leu Arg Arg Leu Glu Met Tyr Cys Ala Pro Leu Lys
                100                 105                 110

Pro Ala Lys Ser Ala Val Pro Gly Trp Arg Arg Pro Thr Thr Leu Tyr
            115                 120                 125

Pro Trp Arg Arg Ala Pro Ala Leu Ser Arg Val Arg Arg Ala Trp Val
            130                 135                 140

Ile Pro Pro Ile Ser Val Ser Glu Asn His Lys Arg Leu Pro Tyr Pro
145                 150                 155                 160

Leu Val Gln Ile Lys Ser Asp Lys Gln Gln Leu Gly Ser Val Ile Tyr
                165                 170                 175

Ser Ile Gln Gly Pro Gly Val Asp Glu Glu Pro Arg Gly Val Phe Ser
            180                 185                 190

Ile Asp Lys Phe Thr Gly Lys Val Phe Leu Asn Ala Met Leu Asp Arg
            195                 200                 205
```

```
Glu Lys Thr Asp Arg Phe Arg Leu Arg Ala Phe Ala Leu Asp Leu Gly
    210                 215                 220

Gly Ser Thr Leu Glu Asp Pro Thr Asp Leu Glu Ile Val Val Val Asp
225                 230                 235                 240

Gln Asn Asp Asn Arg Pro Ala Phe Leu Gln Glu Ala Phe Thr Gly Arg
                245                 250                 255

Val Leu Glu Gly Ala Val Pro Gly Thr Tyr Val Thr Arg Ala Glu Thr
            260                 265                 270

Asp Ala Asp Asp Pro Glu Thr Asp Asn Ala Ala Leu Arg Phe Ser Ile
        275                 280                 285

Leu Gln Gln Gly Ser Pro Glu Leu Phe Ser Ile Asp Glu Leu Thr Gly
    290                 295                 300

Glu Ile Arg Thr Val Gln Val Gly Leu Asp Arg Glu Val Val Ala Val
305                 310                 315                 320

Tyr Asn Leu Thr Leu Gln Val Ala Asp Met Ser Gly Asp Gly Leu Thr
                325                 330                 335

Ala Thr Ala Ala Ile Ile Thr Leu Asp Asp Ile Asn Asp Asn Ala Pro
            340                 345                 350

Glu Phe Thr Arg Asp Glu Phe Phe Met Glu Ala Ile Glu Ala Val Ser
        355                 360                 365

Gly Val Asp Val Gly Arg Leu Glu Val Glu Asp Arg Asp Leu Pro Gly
    370                 375                 380

Ser Pro Asn Trp Val Ala Arg Phe Thr Ile Leu Glu Gly Asp Pro Asp
385                 390                 395                 400

Gly Gln Phe Thr Ile Arg Asp Pro Lys Thr Asn Glu Gly Val Leu Ser
                405                 410                 415

Ile Val Lys Ala Leu Asp Tyr Glu Ser Cys Glu His Tyr Glu Leu Lys
            420                 425                 430

Val Ser Val Gln Asn Glu Ala Pro Leu Gln Ala Ala Leu Arg Ala
        435                 440                 445

Glu Arg Gly Gln Ala Lys Val Arg Val His Val Gln Asp Thr Asn Glu
    450                 455                 460

Pro Pro Val Phe Gln Glu Asn Pro Leu Thr Ser Leu Ala Glu Gly Ala
465                 470                 475                 480

Pro Pro Gly Thr Leu Val Ala Thr Phe Ser Ala Arg Asp Pro Asp Thr
                485                 490                 495

Glu Gln Leu Gln Arg Leu Ser Tyr Ser Lys Asp Tyr Asp Pro Glu Asp
            500                 505                 510

Trp Leu Gln Val Asp Ala Ala Thr Gly Arg Ile Gln Thr Gln His Val
        515                 520                 525

Leu Ser Pro Ala Ser Pro Phe Leu Lys Gly Gly Trp Arg Ala Ile Val
    530                 535                 540

Leu Ala Gln Asp Asp Ala Ser Gln Pro Arg Thr Ala Thr Gly Thr Leu
545                 550                 555                 560

Ser Ile Glu Ile Leu Glu Val Asn Asp His Ala Pro Met Gly Lys Ile
                565                 570                 575

Ser Ser Leu Pro Thr Gln Leu Phe Lys Cys Cys Phe Cys Asp Phe Leu
            580                 585                 590

Lys Val Lys Met His Thr Met Ser Ser His Leu Phe Tyr Leu Ala
        595                 600                 605

Leu Cys Leu Leu Thr Phe Thr Ser Ser Ala Thr Ala Gly Pro Arg Thr
    610                 615                 620
```

```
Leu Cys Gly Ala Glu Leu Val Asp Ala Leu Gln Phe Val Cys Gly Asp
625                 630                 635                 640

Arg Gly Phe Tyr Phe Asn Lys Pro Thr Gly Tyr Gly Ser Ser Ser Arg
            645                 650                 655

Arg Ala Pro Gln Thr Gly Ile Val Asp Glu Cys Cys Phe Arg Ser Cys
        660                 665                 670

Asp Leu Arg Arg Leu Glu Met Tyr Cys Ala Pro Leu Lys Pro Ala Lys
        675                 680                 685

Ser Ala
    690

<210> SEQ ID NO 36
<211> LENGTH: 76
<212> TYPE: PRT
<213> ORGANISM: homo sapien

<400> SEQUENCE: 36

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Arg Thr Leu Cys Gly Ala Glu Leu Val Asp Ala Leu Gln Phe
    50                  55                  60

Val Cys Gly Asp Arg Gly Phe Tyr Phe Asn Lys Pro
65                  70                  75

<210> SEQ ID NO 37
<211> LENGTH: 810
<212> TYPE: PRT
<213> ORGANISM: homo sapien

<400> SEQUENCE: 37

Met Asp Ala Ala Phe Leu Leu Val Leu Gly Leu Leu Ala Gln Ser Leu
1               5                   10                  15

Cys Leu Ser Leu Gly Val Pro Gly Trp Arg Arg Pro Thr Thr Leu Tyr
            20                  25                  30

Pro Trp Arg Arg Ala Pro Ala Leu Ser Arg Val Arg Arg Ala Trp Val
        35                  40                  45

Ile Pro Pro Ile Ser Val Ser Glu Asn His Lys Arg Leu Pro Tyr Pro
    50                  55                  60

Leu Val Ile Lys Ser Asp Lys Gln Gln Leu Gly Ser Val Ile Tyr Ser
65                  70                  75                  80

Ile Gln Gly Pro Gly Val Asp Glu Glu Pro Arg Gly Val Phe Ser Ile
            85                  90                  95

Asp Lys Phe Thr Gly Lys Val Phe Leu Asn Ala Met Leu Asp Arg Glu
        100                 105                 110

Lys Thr Asp Arg Phe Arg Leu Arg Ala Phe Ala Leu Asp Leu Gly Gly
    115                 120                 125

Ser Thr Leu Glu Asp Pro Thr Asp Leu Glu Ile Val Val Val Asp Gln
130                 135                 140

Asn Asp Asn Arg Pro Ala Phe Leu Gln Glu Ala Phe Thr Gly Arg Val
145                 150                 155                 160

Leu Glu Gly Ala Val Pro Gly Thr Tyr Val Thr Arg Ala Glu Ala Thr
            165                 170                 175
```

-continued

```
Asp Ala Asp Asp Pro Glu Thr Asp Asn Ala Ala Leu Arg Phe Ser Ile
            180                 185                 190
Leu Gln Gln Gly Ser Pro Glu Leu Phe Ser Ile Asp Glu Leu Thr Gly
        195                 200                 205
Glu Ile Arg Thr Val Gln Val Gly Leu Asp Arg Glu Val Val Ala Val
    210                 215                 220
Tyr Asn Leu Thr Leu Gln Val Ala Asp Met Ser Gly Asp Gly Leu Thr
225                 230                 235                 240
Ala Thr Ala Ser Ala Ile Ile Thr Leu Asp Asp Ile Asn Asp Asn Ala
                245                 250                 255
Pro Glu Phe Thr Arg Asp Glu Phe Phe Met Glu Ala Ile Glu Ala Val
            260                 265                 270
Ser Gly Val Asp Val Gly Arg Leu Glu Val Glu Asp Arg Asp Leu Pro
        275                 280                 285
Gly Ser Pro Asn Trp Val Ala Arg Phe Thr Ile Leu Glu Gly Asp Pro
    290                 295                 300
Asp Gly Gln Phe Thr Ile Arg Thr Asp Pro Lys Thr Asn Glu Gly Val
305                 310                 315                 320
Leu Ser Ile Val Lys Ala Leu Asp Tyr Glu Ser Cys Glu His Tyr Glu
                325                 330                 335
Leu Lys Val Ser Val Gln Asn Glu Ala Pro Leu Gln Ala Ala Ala Leu
            340                 345                 350
Arg Ala Glu Arg Gly Gln Ala Lys Val Arg Val His Val Gln Asp Thr
        355                 360                 365
Asn Glu Pro Pro Val Phe Gln Glu Asn Pro Leu Arg Thr Ser Leu Ala
    370                 375                 380
Glu Gly Ala Pro Pro Gly Thr Leu Val Ala Thr Phe Ser Ala Arg Asp
385                 390                 395                 400
Pro Asp Thr Glu Gln Leu Gln Arg Leu Ser Tyr Ser Lys Asp Tyr Asp
                405                 410                 415
Pro Glu Asp Trp Leu Gln Val Asp Ala Ala Thr Gly Arg Ile Gln Thr
            420                 425                 430
Gln His Val Leu Ser Pro Ala Ser Pro Phe Leu Lys Gly Gly Trp Tyr
        435                 440                 445
Arg Ala Ile Val Leu Ala Gln Asp Asp Ala Ser Gln Pro Arg Thr Ala
    450                 455                 460
Thr Gly Thr Leu Ser Ile Glu Ile Leu Glu Val Asn Asp His Ala Pro
465                 470                 475                 480
Val Leu Ala Pro Pro Pro Gly Ser Leu Cys Ser Glu Pro His Gln
                485                 490                 495
Gly Pro Gly Leu Leu Gly Ala Thr Asp Glu Asp Leu Pro Pro His
            500                 505                 510
Gly Ala Pro Phe His Phe Gln Leu Ser Pro Arg Leu Pro Glu Leu Gly
        515                 520                 525
Arg Asn Trp Ser Leu Ser Gln Val Asn Val Ser His Ala Arg Leu Arg
    530                 535                 540
Pro Arg His Gln Val Pro Glu Gly Leu His Arg Leu Ser Leu Leu Leu
545                 550                 555                 560
Arg Asp Ser Gly Gln Pro Pro Gln Arg Glu Gln Pro Leu Asn Val
                565                 570                 575
Thr Val Cys Arg Cys Gly Lys Asp Gly Val Cys Leu Pro Gly Ala Ala
            580                 585                 590
Ala Leu Leu Ala Gly Gly Thr Gly Leu Ser Leu Gly Ala Val Ile Val
```

```
                    595                 600                 605
Leu Ala Ser Ala Leu Leu Leu Val Leu Val Leu Val Ala Leu
            610                 615                 620

Arg Ala Arg Phe Trp Lys Gln Ser Arg Lys Gly Leu Leu His Gly
625                 630                 635                 640

Pro Gln Asp Asp Leu Arg Asp Asn Val Leu Asn Tyr Asp Glu Gln Gly
                        645                 650                 655

Gly Gly Glu Glu Asp Gln Asp Ala Tyr Asp Ile Ser Gln Leu Arg His
                660                 665                 670

Thr Ala Leu Ser Leu Pro Leu Gly Pro Pro Leu Arg Arg Asp Ala
            675                 680                 685

Pro Gln Gly Arg Leu His Pro Gln Pro Arg Val Leu Pro Thr Ser
690                 695                 700

Pro Leu Asp Ile Ala Asp Phe Ile Asn Asp Gly Leu Glu Ala Ala Asp
705                 710                 715                 720

Ser Asp Pro Ser Val Pro Pro Tyr Asp Thr Ala Leu Ile Tyr Asp Tyr
                    725                 730                 735

Glu Gly Asp Gly Val Ala Gly Thr Leu Ser Ser Ile Leu Ser Ser Gln
                740                 745                 750

Gly Asp Glu Asp Gln Asp Tyr Asp Tyr Leu Arg Asp Trp Gly Pro Arg
                755                 760                 765

Phe Ala Arg Leu Ala Asp Met Tyr Gly His Pro Cys Gly Leu Glu Tyr
770                 775                 780

Gly Ala Arg Trp Asp His Gln Ala Arg Glu Gly Leu Ser Pro Gly Ala
785                 790                 795                 800

Leu Leu Pro Arg His Arg Gly Arg Thr Ala
                805                 810

<210> SEQ ID NO 38
<211> LENGTH: 463
<212> TYPE: PRT
<213> ORGANISM: homo sapien

<400> SEQUENCE: 38

Ser Leu Gly Val Pro Gly Trp Arg Arg Pro Thr Thr Leu Tyr Pro Trp
1               5                   10                  15

Arg Arg Ala Pro Ala Leu Ser Arg Val Arg Arg Ala Trp Val Ile Pro
                20                  25                  30

Pro Ile Ser Val Ser Glu Asn His Lys Arg Leu Pro Tyr Pro Leu Val
            35                  40                  45

Gln Ile Lys Ser Asp Lys Gln Gln Leu Gly Ser Val Ile Tyr Ser Ile
        50                  55                  60

Gln Gly Pro Gly Val Asp Glu Glu Pro Arg Gly Val Phe Ser Ile Asp
65                  70                  75                  80

Lys Phe Thr Gly Lys Val Phe Leu Asn Ala Met Leu Asp Arg Glu Lys
                85                  90                  95

Thr Asp Arg Phe Arg Leu Arg Ala Phe Ala Leu Asp Leu Gly Gly Ser
                100                 105                 110

Thr Leu Glu Asp Pro Thr Asp Leu Glu Ile Val Val Val Asp Gln Asn
            115                 120                 125

Asp Asn Arg Pro Ala Phe Leu Gln Glu Ala Phe Thr Gly Arg Val Leu
        130                 135                 140

Glu Gly Ala Val Pro Gly Thr Tyr Val Thr Arg Ala Glu Ala Thr Asp
145                 150                 155                 160
```

```
Ala Asp Asp Pro Glu Thr Asp Asn Ala Ala Leu Arg Phe Ser Ile Leu
            165                 170                 175

Gln Gln Gly Ser Pro Glu Leu Phe Ser Ile Asp Glu Leu Thr Gly Glu
        180                 185                 190

Ile Arg Thr Val Gln Val Gly Leu Asp Arg Glu Val Val Ala Val Tyr
            195                 200                 205

Asn Leu Thr Leu Gln Val Ala Asp Met Ser Gly Asp Gly Leu Thr Ala
        210                 215                 220

Thr Ala Ser Ala Ile Ile Thr Leu Asp Asp Ile Asn Asp Asn Ala Pro
225                 230                 235                 240

Glu Phe Thr Arg Asp Glu Phe Phe Met Glu Ala Ile Glu Ala Val Ser
                245                 250                 255

Gly Val Asp Val Gly Arg Leu Glu Val Glu Asp Arg Asp Leu Pro Gly
            260                 265                 270

Ser Pro Asn Trp Val Ala Arg Phe Thr Ile Leu Glu Gly Asp Pro Asp
        275                 280                 285

Gly Gln Phe Thr Ile Arg Thr Asp Pro Lys Thr Asn Glu Gly Val Leu
    290                 295                 300

Ser Ile Val Lys Ala Leu Asp Tyr Glu Ser Cys Glu His Tyr Glu Leu
305                 310                 315                 320

Lys Val Ser Val Gln Asn Glu Ala Pro Leu Gln Ala Ala Leu Arg
                325                 330                 335

Ala Glu Arg Gly Gln Ala Lys Val Arg Val His Val Gln Asp Thr Asn
            340                 345                 350

Glu Pro Pro Val Phe Gln Glu Asn Pro Leu Arg Thr Ser Leu Ala Glu
        355                 360                 365

Gly Ala Pro Pro Gly Thr Leu Val Ala Thr Phe Ser Ala Arg Asp Pro
    370                 375                 380

Asp Thr Glu Gln Leu Gln Arg Leu Ser Tyr Ser Lys Asp Tyr Asp Pro
385                 390                 395                 400

Glu Asp Trp Leu Gln Val Asp Ala Ala Thr Gly Arg Ile Gln Thr Gln
                405                 410                 415

His Val Leu Ser Pro Ala Ser Pro Phe Leu Lys Gly Trp Tyr Arg
            420                 425                 430

Ala Ile Val Leu Ala Gln Asp Asp Ala Ser Gln Pro Arg Thr Ala Thr
        435                 440                 445

Gly Thr Leu Ser Ile Glu Ile Leu Glu Val Asn Asp His Ala Pro
    450                 455                 460

<210> SEQ ID NO 39
<211> LENGTH: 985
<212> TYPE: PRT
<213> ORGANISM: homo sapien

<400> SEQUENCE: 39

Met Asp Ala Ala Phe Leu Leu Val Leu Gly Leu Leu Ala Gln Ser Leu
  1               5                  10                  15

Cys Leu Ser Leu Gly Val Pro Gly Trp Arg Arg Pro Thr Thr Leu Tyr
                20                  25                  30

Pro Trp Arg Arg Ala Pro Ala Leu Ser Arg Val Arg Arg Ala Trp Val
            35                  40                  45

Ile Pro Pro Ile Ser Val Ser Glu Asn His Lys Arg Leu Pro Tyr Pro
        50                  55                  60

Leu Val Gln Ile Lys Ser Asp Lys Gln Gln Leu Gly Ser Val Ile Tyr
65                  70                  75                  80
```

-continued

```
Ser Ile Gln Gly Pro Gly Val Asp Glu Pro Arg Gly Val Phe Ser
             85                  90                  95

Ile Asp Lys Phe Thr Gly Lys Val Phe Leu Asn Ala Met Leu Asp Arg
            100                 105                 110

Glu Lys Thr Asp Arg Phe Arg Leu Arg Ala Phe Ala Leu Asp Leu Gly
            115                 120                 125

Gly Ser Thr Leu Glu Asp Pro Thr Asp Leu Ile Val Val Asp
        130                 135                 140

Gln Asn Asp Asn Arg Pro Ala Phe Leu Gln Glu Ala Phe Thr Gly Arg
145                 150                 155                 160

Val Leu Glu Gly Ala Val Pro Gly Thr Tyr Val Thr Arg Ala Glu Ala
            165                 170                 175

Thr Asp Ala Asp Asp Pro Glu Thr Asp Asn Ala Ala Leu Arg Phe Ser
            180                 185                 190

Ile Leu Gln Gln Gly Ser Pro Glu Leu Phe Ser Ile Asp Glu Leu Thr
            195                 200                 205

Gly Glu Ile Arg Thr Val Gln Val Gly Leu Asp Arg Glu Val Val Ala
        210                 215                 220

Val Tyr Asn Leu Thr Leu Gln Val Ala Asp Met Ser Gly Asp Gly Leu
225                 230                 235                 240

Thr Ala Thr Ala Ser Ala Ile Ile Thr Leu Asp Asp Ile Asn Asp Asn
            245                 250                 255

Ala Pro Glu Phe Thr Arg Asp Glu Phe Phe Met Glu Ala Ile Glu Ala
            260                 265                 270

Val Ser Gly Val Asp Val Gly Arg Leu Glu Val Glu Asp Arg Asp Leu
            275                 280                 285

Pro Gly Ser Pro Asn Trp Val Ala Arg Phe Thr Ile Leu Glu Gly Asp
        290                 295                 300

Pro Asp Gly Gln Phe Thr Ile Arg Thr Asp Pro Lys Thr Asn Glu Gly
305                 310                 315                 320

Val Leu Ser Ile Val Lys Ala Leu Asp Tyr Glu Ser Cys Glu His Tyr
            325                 330                 335

Glu Leu Lys Val Ser Val Gln Asn Glu Ala Pro Leu Gln Ala Ala Ala
            340                 345                 350

Leu Arg Ala Glu Arg Gly Gln Ala Lys Val Arg Val His Val Gln Asp
        355                 360                 365

Thr Asn Glu Pro Pro Val Phe Gln Glu Asn Pro Leu Arg Thr Ser Leu
        370                 375                 380

Ala Glu Gly Ala Pro Pro Gly Thr Leu Val Ala Thr Phe Ser Ala Arg
385                 390                 395                 400

Asp Pro Asp Thr Glu Gln Leu Gln Arg Leu Ser Tyr Ser Lys Asp Tyr
            405                 410                 415

Asp Pro Glu Asp Trp Leu Gln Val Asp Ala Ala Thr Gly Arg Ile Gln
            420                 425                 430

Thr Gln His Val Leu Ser Pro Ala Ser Pro Phe Leu Lys Gly Gly Trp
        435                 440                 445

Tyr Arg Ala Ile Val Leu Ala Gln Asp Asp Ala Ser Gln Pro Arg Thr
450                 455                 460

Ala Thr Gly Thr Leu Ser Ile Glu Ile Leu Glu Val Asn Asp His Ala
465                 470                 475                 480

Pro Ser Gly Ile Ile Pro Val Glu Glu Glu Asn Pro Asp Phe Trp Asn
            485                 490                 495
```

```
Arg Glu Ala Ala Glu Ala Leu Gly Ala Ala Lys Lys Leu Gln Pro Ala
            500                 505                 510

Gln Thr Ala Ala Lys Asn Leu Ile Ile Phe Leu Gly Asp Gly Met Gly
        515                 520                 525

Val Ser Thr Val Thr Ala Ala Arg Ile Leu Lys Gly Gln Lys Lys Asp
    530                 535                 540

Lys Leu Gly Pro Glu Ile Pro Leu Ala Met Asp Arg Phe Pro Tyr Val
545                 550                 555                 560

Ala Leu Ser Lys Thr Tyr Asn Val Asp Lys His Val Pro Asp Ser Gly
                565                 570                 575

Ala Thr Ala Thr Ala Tyr Leu Cys Gly Val Lys Gly Asn Phe Gln Thr
            580                 585                 590

Ile Gly Leu Ser Ala Ala Arg Phe Asn Gln Cys Asn Thr Thr Arg
        595                 600                 605

Gly Asn Glu Val Ile Ser Val Met Asn Arg Ala Lys Lys Ala Gly Lys
    610                 615                 620

Ser Val Gly Val Val Thr Thr Thr Arg Val Gln His Ala Ser Pro Ala
625                 630                 635                 640

Gly Thr Tyr Ala His Thr Val Asn Arg Asn Trp Tyr Ser Asp Ala Asp
                645                 650                 655

Val Pro Ala Ser Ala Arg Gln Glu Gly Cys Gln Asp Ile Ala Thr Gln
            660                 665                 670

Leu Ile Ser Asn Met Asp Ile Asp Val Ile Leu Gly Gly Gly Arg Lys
        675                 680                 685

Tyr Met Phe Arg Met Gly Thr Pro Asp Pro Glu Tyr Pro Asp Asp Tyr
    690                 695                 700

Ser Gln Gly Gly Thr Arg Leu Asp Gly Lys Asn Leu Val Gln Glu Trp
705                 710                 715                 720

Leu Ala Lys Arg Gln Gly Ala Arg Tyr Val Trp Asn Arg Thr Glu Leu
                725                 730                 735

Met Gln Ala Ser Leu Asp Pro Ser Val Thr His Leu Met Gly Leu Phe
            740                 745                 750

Glu Pro Gly Asp Met Lys Tyr Glu Ile His Arg Asp Ser Thr Leu Asp
        755                 760                 765

Pro Ser Leu Met Glu Met Thr Glu Ala Ala Leu Arg Leu Leu Ser Arg
    770                 775                 780

Asn Pro Arg Gly Phe Phe Leu Phe Val Glu Gly Gly Arg Ile Asp His
785                 790                 795                 800

Gly His His Glu Ser Arg Ala Tyr Arg Ala Leu Thr Glu Thr Ile Met
                805                 810                 815

Phe Asp Asp Ala Ile Glu Arg Ala Gly Gln Leu Thr Ser Glu Glu Asp
            820                 825                 830

Thr Leu Ser Leu Val Thr Ala Asp His Ser His Val Phe Ser Phe Gly
        835                 840                 845

Gly Tyr Pro Leu Arg Gly Ser Ser Ile Phe Gly Leu Ala Pro Gly Lys
    850                 855                 860

Ala Arg Asp Arg Lys Ala Tyr Thr Val Leu Leu Tyr Gly Asn Gly Pro
865                 870                 875                 880

Gly Tyr Val Leu Lys Asp Gly Ala Arg Pro Asp Val Thr Glu Ser Glu
                885                 890                 895

Ser Gly Ser Pro Glu Tyr Arg Gln Gln Ser Ala Val Pro Leu Asp Glu
            900                 905                 910

Glu Thr His Ala Gly Glu Asp Val Ala Val Phe Ala Arg Gly Pro Gln
```

```
                915                 920                 925
Ala His Leu Val His Gly Val Gln Glu Gln Thr Phe Ile Ala His Val
    930                 935                 940

Met Ala Phe Ala Ala Cys Leu Glu Pro Tyr Thr Ala Cys Asp Leu Ala
945                 950                 955                 960

Pro Pro Ala Gly Thr Thr Asp Ala Ala His Pro Gly Tyr Ser Arg Val
                965                 970                 975

Gly Ala Ala Gly Arg Phe Glu Gln Thr
            980                 985

<210> SEQ ID NO 40
<211> LENGTH: 374
<212> TYPE: PRT
<213> ORGANISM: homo sapien

<400> SEQUENCE: 40

Met Asp Ala Ala Phe Leu Leu Val Leu Gly Leu Ala Gln Ser Leu
 1               5                  10                  15

Cys Leu Ser Leu Gly Val Pro Gly Trp Arg Arg Pro Thr Thr Leu Tyr
                20                  25                  30

Pro Trp Arg Arg Ala Pro Ala Leu Ser Arg Val Arg Arg Ala Trp Val
            35                  40                  45

Ile Pro Pro Ile Ser Val Ser Glu Asn His Lys Arg Leu Pro Tyr Pro
        50                  55                  60

Leu Val Gln Ile Lys Ser Asp Lys Gln Leu Gly Ser Val Ile Tyr
65                  70                  75                  80

Ser Ile Gln Gly Pro Gly Val Asp Glu Glu Pro Arg Gly Val Phe Ser
                85                  90                  95

Ile Asp Lys Phe Thr Gly Lys Val Phe Leu Asn Ala Met Leu Asp Arg
            100                 105                 110

Glu Lys Thr Asp Arg Phe Arg Leu Arg Ala Phe Ala Leu Asp Leu Gly
        115                 120                 125

Gly Ser Thr Leu Glu Asp Pro Thr Asp Leu Glu Ile Val Val Asp
    130                 135                 140

Gln Asn Asp Asn Arg Pro Ala Phe Leu Gln Glu Ala Phe Thr Gly Arg
145                 150                 155                 160

Val Leu Glu Gly Ala Val Pro Gly Thr Tyr Val Thr Arg Ala Glu Ala
                165                 170                 175

Thr Asp Ala Asp Asp Pro Glu Thr Asp Asn Ala Ala Leu Arg Phe Ser
            180                 185                 190

Ile Leu Gln Gln Gly Ser Pro Glu Leu Phe Ser Ile Asp Glu Leu Thr
        195                 200                 205

Gly Glu Ile Arg Thr Val Gln Val Gly Leu Asp Arg Glu Val Val Ala
    210                 215                 220

Val Tyr Asn Leu Thr Leu Gln Val Ala Asp Met Ser Gly Asp Gly Leu
225                 230                 235                 240

Thr Ala Thr Ala Ser Ala Ile Ile Thr Leu Asp Asp Ile Asn Asp Asn
                245                 250                 255

Ala Pro Glu Phe Thr Arg Asp Glu Phe Phe Met Glu Ala Ile Glu Ala
            260                 265                 270

Val Ser Gly Val Asp Val Gly Arg Leu Glu Val Glu Asp Arg Asp Leu
        275                 280                 285

Pro Gly Ser Pro Asn Trp Val Ala Arg Phe Thr Ile Leu Glu Gly Asp
    290                 295                 300
```

```
Pro Asp Gly Gln Phe Thr Ile Arg Thr Asp Pro Lys Thr Asn Glu Gly
305                 310                 315                 320

Val Leu Ser Ile Val Lys Ala Leu Asp Tyr Glu Ser Cys Glu His Tyr
                325                 330                 335

Glu Leu Lys Val Ser Val Gln Asn Glu Ala Pro Leu Gln Ala Ala Ala
            340                 345                 350

Leu Arg Ala Glu Arg Gly Gln Ala Lys Val Arg Val His Val Gln Asp
        355                 360                 365

Thr Asn Glu Pro Pro Val
    370
```

<210> SEQ ID NO 41
<211> LENGTH: 878
<212> TYPE: PRT
<213> ORGANISM: homo sapien

<400> SEQUENCE: 41

```
Met Asp Ala Ala Phe Leu Leu Val Leu Gly Leu Leu Ala Gln Ser Leu
1               5                   10                  15

Cys Leu Ser Leu Gly Val Pro Gly Trp Arg Arg Pro Thr Thr Leu Tyr
            20                  25                  30

Pro Trp Arg Arg Ala Pro Ala Leu Ser Arg Val Arg Arg Ala Trp Val
        35                  40                  45

Ile Pro Pro Ile Ser Val Ser Glu Asn His Lys Arg Leu Pro Tyr Pro
50                  55                  60

Leu Val Gln Ile Lys Ser Asp Lys Gln Gln Leu Gly Ser Val Ile Tyr
65                  70                  75                  80

Ser Ile Gln Gly Pro Gly Val Asp Glu Glu Pro Arg Gly Val Phe Ser
                85                  90                  95

Ile Asp Lys Phe Thr Gly Lys Val Phe Leu Asn Ala Met Leu Asp Arg
            100                 105                 110

Glu Lys Thr Asp Arg Phe Arg Leu Arg Ala Phe Ala Leu Asp Leu Gly
        115                 120                 125

Gly Ser Thr Leu Glu Asp Pro Thr Asp Leu Glu Ile Val Val Val Asp
130                 135                 140

Gln Asn Asp Asn Arg Pro Ala Phe Leu Gln Glu Ala Phe Thr Gly Arg
145                 150                 155                 160

Val Leu Glu Gly Ala Val Pro Gly Thr Tyr Val Thr Arg Ala Glu Ala
                165                 170                 175

Thr Asp Ala Asp Asp Pro Glu Thr Asp Asn Ala Ala Leu Arg Phe Ser
            180                 185                 190

Ile Leu Gln Gln Gly Ser Pro Glu Leu Phe Ser Ile Asp Glu Leu Thr
        195                 200                 205

Gly Glu Ile Arg Thr Val Gln Val Gly Leu Asp Arg Glu Val Val Ala
    210                 215                 220

Val Tyr Asn Leu Thr Leu Gln Val Ala Asp Met Ser Gly Asp Gly Leu
225                 230                 235                 240

Thr Ala Thr Ala Ser Ala Ile Ile Thr Leu Asp Asp Ile Asn Asp Asn
                245                 250                 255

Ala Pro Glu Phe Thr Arg Asp Glu Phe Phe Met Glu Ala Ile Glu Ala
            260                 265                 270

Val Ser Gly Val Asp Val Gly Arg Leu Glu Val Glu Asp Arg Asp Leu
        275                 280                 285

Pro Gly Ser Pro Asn Trp Val Ala Arg Phe Thr Ile Leu Glu Gly Asp
    290                 295                 300
```

-continued

```
Pro Asp Gly Gln Phe Thr Ile Arg Thr Asp Pro Lys Thr Asn Glu Gly
305                 310                 315                 320

Val Leu Ser Ile Val Lys Ala Leu Asp Tyr Glu Ser Cys Glu His Tyr
                325                 330                 335

Glu Leu Lys Val Ser Val Gln Asn Glu Ala Pro Leu Gln Ala Ala Ala
            340                 345                 350

Leu Arg Ala Glu Arg Gly Gln Ala Lys Val Arg Val His Val Gln Asp
        355                 360                 365

Thr Asn Glu Pro Pro Val Ser Gly Ile Ile Pro Val Glu Glu Glu Asn
    370                 375                 380

Pro Asp Phe Trp Asn Arg Glu Ala Ala Glu Ala Leu Gly Ala Ala Lys
385                 390                 395                 400

Lys Leu Gln Pro Ala Gln Thr Ala Ala Lys Asn Leu Ile Ile Phe Leu
                405                 410                 415

Gly Asp Gly Met Gly Val Ser Thr Val Thr Ala Ala Arg Ile Leu Lys
            420                 425                 430

Gly Gln Lys Lys Asp Lys Leu Gly Pro Glu Ile Pro Leu Ala Met Asp
        435                 440                 445

Arg Phe Pro Tyr Val Ala Leu Ser Lys Thr Tyr Asn Val Asp Lys His
        450                 455                 460

Val Pro Asp Ser Gly Ala Thr Ala Thr Ala Tyr Leu Cys Gly Val Lys
465                 470                 475                 480

Gly Asn Phe Gln Thr Ile Gly Leu Ser Ala Ala Ala Arg Phe Asn Gln
                485                 490                 495

Cys Asn Thr Thr Arg Gly Asn Glu Val Ile Ser Val Met Asn Arg Ala
            500                 505                 510

Lys Lys Ala Gly Lys Ser Val Gly Val Val Thr Thr Thr Arg Val Gln
        515                 520                 525

His Ala Ser Pro Ala Gly Thr Tyr Ala His Thr Val Asn Arg Asn Trp
    530                 535                 540

Tyr Ser Asp Ala Asp Val Pro Ala Ser Ala Arg Gln Glu Gly Cys Gln
545                 550                 555                 560

Asp Ile Ala Thr Gln Leu Ile Ser Asn Met Asp Ile Asp Val Ile Leu
                565                 570                 575

Gly Gly Gly Arg Lys Tyr Met Phe Arg Met Gly Thr Pro Asp Pro Glu
            580                 585                 590

Tyr Pro Asp Asp Tyr Ser Gln Gly Gly Thr Arg Leu Asp Gly Lys Asn
        595                 600                 605

Leu Val Gln Glu Trp Leu Ala Lys Arg Gln Gly Ala Arg Tyr Val Trp
    610                 615                 620

Asn Arg Thr Glu Leu Met Gln Ala Ser Leu Asp Pro Ser Val Thr His
625                 630                 635                 640

Leu Met Gly Leu Phe Glu Pro Gly Asp Met Lys Tyr Glu Ile His Arg
                645                 650                 655

Asp Ser Thr Leu Asp Pro Ser Leu Met Glu Met Thr Glu Ala Ala Leu
            660                 665                 670

Arg Leu Leu Ser Arg Asn Pro Arg Gly Phe Phe Leu Phe Val Glu Gly
        675                 680                 685

Gly Arg Ile Asp His Gly His His Glu Ser Arg Ala Tyr Arg Ala Leu
    690                 695                 700

Thr Glu Thr Ile Met Phe Asp Asp Ala Ile Glu Arg Ala Gly Gln Leu
705                 710                 715                 720
```

```
Thr Ser Glu Glu Asp Thr Leu Ser Leu Val Thr Ala Asp His Ser His
                725                 730                 735

Val Phe Ser Phe Gly Tyr Pro Leu Arg Gly Ser Ser Ile Phe Gly
            740                 745                 750

Leu Ala Pro Gly Lys Ala Arg Asp Arg Lys Ala Tyr Thr Val Leu Leu
            755                 760                 765

Tyr Gly Asn Gly Pro Gly Tyr Val Leu Lys Asp Gly Ala Arg Pro Asp
            770                 775                 780

Val Thr Glu Ser Glu Ser Gly Ser Pro Glu Tyr Arg Gln Gln Ser Ala
785                 790                 795                 800

Val Pro Leu Asp Glu Glu Thr His Ala Gly Glu Asp Val Ala Val Phe
                805                 810                 815

Ala Arg Gly Pro Gln Ala His Leu Val His Gly Val Gln Glu Gln Thr
            820                 825                 830

Phe Ile Ala His Val Met Ala Phe Ala Ala Cys Leu Glu Pro Tyr Thr
            835                 840                 845

Ala Cys Asp Leu Ala Pro Pro Ala Gly Thr Thr Asp Ala Ala His Pro
            850                 855                 860

Gly Tyr Ser Arg Val Gly Ala Ala Gly Arg Phe Glu Gln Thr
865                 870                 875

<210> SEQ ID NO 42
<211> LENGTH: 762
<212> TYPE: PRT
<213> ORGANISM: homo sapien

<400> SEQUENCE: 42

Met Asp Ala Ala Phe Leu Leu Val Leu Gly Leu Leu Ala Gln Ser Leu
1               5                   10                  15

Cys Leu Ser Leu Gly Val Pro Gly Trp Arg Arg Pro Thr Thr Leu Tyr
            20                  25                  30

Pro Trp Arg Arg Ala Pro Ala Leu Ser Arg Val Arg Arg Ala Trp Val
            35                  40                  45

Ile Pro Pro Ile Ser Val Ser Glu Asn His Lys Arg Leu Pro Tyr Pro
            50                  55                  60

Leu Val Gln Ile Lys Ser Asp Lys Gln Gln Leu Gly Ser Val Ile Tyr
65                  70                  75                  80

Ser Ile Gln Gly Pro Gly Val Asp Glu Glu Pro Arg Gly Val Phe Ser
                85                  90                  95

Ile Asp Lys Phe Thr Gly Lys Val Phe Leu Asn Ala Met Leu Asp Arg
            100                 105                 110

Glu Lys Thr Asp Arg Phe Arg Leu Arg Ala Phe Ala Leu Asp Leu Gly
            115                 120                 125

Gly Ser Thr Leu Glu Asp Pro Thr Asp Leu Glu Ile Val Val Asp
            130                 135                 140

Gln Asn Asp Asn Arg Pro Ala Phe Leu Gln Glu Ala Phe Thr Gly Arg
145                 150                 155                 160

Val Leu Glu Gly Ala Val Pro Gly Thr Tyr Val Thr Arg Ala Glu Ala
                165                 170                 175

Thr Asp Ala Asp Asp Pro Glu Thr Asp Asn Ala Ala Leu Arg Phe Ser
            180                 185                 190

Ile Leu Gln Gln Gly Ser Pro Glu Leu Phe Ser Ile Asp Glu Leu Thr
            195                 200                 205

Gly Glu Ile Arg Thr Val Gln Val Gly Leu Asp Arg Glu Val Val Ala
            210                 215                 220
```

```
Val Tyr Asn Leu Thr Leu Gln Val Ala Asp Met Ser Gly Asp Gly Leu
225                 230                 235                 240

Thr Ala Thr Ala Ser Ala Ile Ile Thr Leu Asp Asp Ile Asn Asp Asn
            245                 250                 255

Ala Pro Ser Gly Ile Ile Pro Val Glu Glu Asn Pro Asp Phe Trp
            260                 265                 270

Asn Arg Glu Ala Ala Glu Ala Leu Gly Ala Ala Lys Lys Leu Gln Pro
        275                 280                 285

Ala Gln Thr Ala Ala Lys Asn Leu Ile Ile Phe Leu Gly Asp Gly Met
    290                 295                 300

Gly Val Ser Thr Val Thr Ala Ala Arg Ile Leu Lys Gly Gln Lys Lys
305                 310                 315                 320

Asp Lys Leu Gly Pro Glu Ile Pro Leu Ala Met Asp Arg Phe Pro Tyr
                325                 330                 335

Val Ala Leu Ser Lys Thr Tyr Asn Val Asp Lys His Val Pro Asp Ser
            340                 345                 350

Gly Ala Thr Ala Thr Ala Tyr Leu Cys Gly Val Lys Gly Asn Phe Gln
        355                 360                 365

Thr Ile Gly Leu Ser Ala Ala Ala Arg Phe Asn Gln Cys Asn Thr Thr
    370                 375                 380

Arg Gly Asn Glu Val Ile Ser Val Met Asn Arg Ala Lys Lys Ala Gly
385                 390                 395                 400

Lys Ser Val Gly Val Val Thr Thr Thr Arg Val Gln His Ala Ser Pro
                405                 410                 415

Ala Gly Thr Tyr Ala His Thr Val Asn Arg Asn Trp Tyr Ser Asp Ala
            420                 425                 430

Asp Val Pro Ala Ser Ala Arg Gln Glu Gly Cys Gln Asp Ile Ala Thr
        435                 440                 445

Gln Leu Ile Ser Asn Met Asp Ile Asp Val Ile Leu Gly Gly Gly Arg
    450                 455                 460

Lys Tyr Met Phe Arg Met Gly Thr Pro Asp Pro Glu Tyr Pro Asp Asp
465                 470                 475                 480

Tyr Ser Gln Gly Gly Thr Arg Leu Asp Gly Lys Asn Leu Val Gln Glu
                485                 490                 495

Trp Leu Ala Lys Arg Gln Gly Ala Arg Tyr Val Trp Asn Arg Thr Glu
            500                 505                 510

Leu Met Gln Ala Ser Leu Asp Pro Ser Val Thr His Leu Met Gly Leu
        515                 520                 525

Phe Glu Pro Gly Asp Met Lys Tyr Glu Ile His Arg Asp Ser Thr Leu
    530                 535                 540

Asp Pro Ser Leu Met Glu Met Thr Glu Ala Ala Leu Arg Leu Leu Ser
545                 550                 555                 560

Arg Asn Pro Arg Gly Phe Phe Leu Phe Val Glu Gly Gly Arg Ile Asp
                565                 570                 575

His Gly His His Glu Ser Arg Ala Tyr Arg Ala Leu Thr Glu Thr Ile
            580                 585                 590

Met Phe Asp Asp Ala Ile Glu Arg Ala Gly Gln Leu Thr Ser Glu Glu
        595                 600                 605

Asp Thr Leu Ser Leu Val Thr Ala Asp His Ser His Val Phe Ser Phe
    610                 615                 620

Gly Gly Tyr Pro Leu Arg Gly Ser Ser Ile Phe Gly Leu Ala Pro Gly
625                 630                 635                 640
```

```
Lys Ala Arg Asp Arg Lys Ala Tyr Thr Val Leu Leu Tyr Gly Asn Gly
                645                 650                 655

Pro Gly Tyr Val Leu Lys Asp Gly Ala Arg Pro Asp Val Thr Glu Ser
            660                 665                 670

Glu Ser Gly Ser Pro Glu Tyr Arg Gln Gln Ser Ala Val Pro Leu Asp
        675                 680                 685

Glu Glu Thr His Ala Gly Glu Asp Val Ala Val Phe Ala Arg Gly Pro
    690                 695                 700

Gln Ala His Leu Val His Gly Val Gln Glu Gln Thr Phe Ile Ala His
705                 710                 715                 720

Val Met Ala Phe Ala Ala Cys Leu Glu Pro Tyr Thr Ala Cys Asp Leu
                725                 730                 735

Ala Pro Pro Ala Gly Thr Thr Asp Ala Ala His Pro Gly Tyr Ser Arg
            740                 745                 750

Val Gly Ala Ala Gly Arg Phe Glu Gln Thr
        755                 760

<210> SEQ ID NO 43
<211> LENGTH: 317
<212> TYPE: PRT
<213> ORGANISM: homo sapien

<400> SEQUENCE: 43

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255
```

```
Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
            275                 280                 285

Ala Thr Tyr Ala Ser Glu Cys Ala Met Lys Glu Ala Ala Cys Ser Ser
            290                 295                 300

Gly Val Leu Leu Glu Val Lys His Ser Gly Ser Cys Asn
305                 310                 315

<210> SEQ ID NO 44
<211> LENGTH: 308
<212> TYPE: PRT
<213> ORGANISM: homo sapien

<400> SEQUENCE: 44

Met Trp Lys Arg Trp Leu Ala Leu Ala Leu Ala Leu Ala Val Ala
 1               5                  10                  15

Trp Val Arg Ala Glu Glu Leu Arg Ser Lys Ser Lys Ile Cys Ala
                20                  25                  30

Asn Val Phe Cys Gly Ala Gly Arg Glu Cys Ala Val Thr Glu Lys Gly
            35                  40                  45

Glu Pro Thr Cys Leu Cys Ile Glu Gln Cys Lys Pro His Lys Arg Pro
            50                  55                  60

Val Cys Gly Ser Asn Gly Lys Thr Tyr Leu Asn His Cys Glu Leu His
65                  70                  75                  80

Arg Asp Ala Cys Leu Thr Gly Ser Lys Ile Gln Val Asp Tyr Asp Gly
                85                  90                  95

His Cys Lys Glu Lys Lys Ser Val Ser Pro Ser Ala Ser Pro Val Val
            100                 105                 110

Cys Tyr Gln Ser Asn Arg Asp Glu Leu Arg Arg Arg Ile Ile Gln Trp
            115                 120                 125

Leu Glu Ala Glu Ile Ile Pro Asp Gly Trp Phe Ser Lys Gly Ser Asn
130                 135                 140

Tyr Ser Glu Ile Leu Asp Lys Tyr Phe Lys Asn Phe Asp Asn Gly Asp
145                 150                 155                 160

Ser Arg Leu Asp Ser Ser Glu Phe Leu Lys Phe Val Glu Gln Asn Glu
                165                 170                 175

Thr Ala Ile Asn Ile Thr Thr Tyr Pro Asp Gln Glu Asn Asn Lys Leu
            180                 185                 190

Leu Arg Gly Leu Cys Val Asp Ala Leu Ile Glu Leu Ser Asp Glu Asn
            195                 200                 205

Ala Asp Trp Lys Leu Ser Phe Gln Glu Phe Leu Lys Cys Leu Asn Pro
            210                 215                 220

Ser Phe Asn Pro Pro Glu Lys Lys Cys Ala Leu Glu Asp Glu Thr Tyr
225                 230                 235                 240

Ala Asp Gly Ala Glu Thr Glu Val Asp Cys Asn Arg Cys Val Cys Ala
                245                 250                 255

Cys Gly Asn Trp Val Cys Thr Ala Met Thr Cys Asp Gly Lys Asn Gln
            260                 265                 270

Lys Gly Ala Gln Thr Gln Thr Glu Glu Met Thr Arg Tyr Val Gln
            275                 280                 285

Glu Leu Gln Lys His Gln Glu Thr Ala Glu Lys Thr Lys Arg Val Ser
            290                 295                 300

Thr Lys Glu Ile
```

<210> SEQ ID NO 45
<211> LENGTH: 263
<212> TYPE: PRT
<213> ORGANISM: homo sapien

<400> SEQUENCE: 45

```
Met Arg Pro Gly Ala Pro Gly Pro Leu Trp Pro Leu Pro Trp Gly Ala
 1               5                  10                  15

Leu Ala Trp Ala Val Gly Phe Val Ser Ser Met Gly Ser Gly Asn Pro
            20                  25                  30

Ala Pro Gly Gly Val Cys Trp Leu Gln Gln Gly Gln Glu Ala Thr Cys
        35                  40                  45

Ser Leu Val Leu Gln Thr Asp Val Thr Arg Ala Glu Cys Cys Ala Ser
    50                  55                  60

Gly Asn Ile Asp Thr Ala Trp Ser Asn Leu Thr His Pro Gly Asn Lys
65                  70                  75                  80

Ile Asn Leu Leu Gly Phe Leu Gly Leu Val His Cys Leu Pro Cys Lys
                85                  90                  95

Asp Ser Cys Asp Gly Val Glu Cys Gly Pro Gly Lys Ala Cys Arg Met
            100                 105                 110

Leu Gly Gly Arg Pro Arg Cys Glu Cys Ala Pro Asp Cys Ser Gly Leu
        115                 120                 125

Pro Ala Arg Leu Gln Val Cys Gly Ser Asp Gly Ala Thr Tyr Arg Asp
    130                 135                 140

Glu Cys Glu Leu Arg Ala Ala Arg Cys Arg Gly His Pro Asp Leu Ser
145                 150                 155                 160

Val Met Tyr Arg Gly Arg Cys Arg Lys Ser Cys Glu His Val Val Cys
                165                 170                 175

Pro Arg Pro Gln Ser Cys Val Val Asp Gln Thr Gly Ser Ala His Cys
            180                 185                 190

Val Val Cys Arg Ala Ala Pro Cys Pro Val Pro Ser Ser Pro Gly Gln
        195                 200                 205

Glu Leu Cys Gly Asn Asn Asn Val Thr Tyr Ile Ser Ser Cys His Met
    210                 215                 220

Arg Gln Ala Thr Cys Phe Leu Gly Arg Ser Ile Gly Val Arg His Ala
225                 230                 235                 240

Gly Ser Cys Ala Gly Thr Pro Glu Glu Pro Pro Gly Gly Glu Ser Ala
                245                 250                 255

Glu Glu Glu Glu Asn Phe Val
            260
```

<210> SEQ ID NO 46
<211> LENGTH: 82
<212> TYPE: PRT
<213> ORGANISM: homo sapien

<400> SEQUENCE: 46

```
Val Gly Lys Ile Lys Ser Ser Val Ser Arg Lys Asn Ala Lys Tyr Leu
 1               5                  10                  15

Leu Lys Gly Glu Tyr Val Gly Lys Val Phe Arg Val Asp Ala Glu Thr
            20                  25                  30

Gly Asp Val Phe Ala Ile Glu Arg Leu Asp Arg Glu Asn Ile Ser Glu
        35                  40                  45

Tyr His Leu Thr Ala Val Ile Val Asp Lys Asp Thr Gly Glu Asn Leu
```

```
                50                  55                  60
Glu Thr Pro Ser Ser Phe Thr Ile Lys Val His Asp Val Asn Asp Asn
 65                  70                  75                  80

Trp Pro
```

<210> SEQ ID NO 47
<211> LENGTH: 84
<212> TYPE: PRT
<213> ORGANISM: homo sapien

<400> SEQUENCE: 47

```
Val Thr Ala Val Asp Ala Asp Pro Thr Val Gly Asp His Ala Ser
 1               5                  10                  15

Val Met Tyr Gln Ile Leu Lys Gly Lys Glu Tyr Phe Ala Ile Asp Asn
                20                  25                  30

Ser Gly Arg Ile Ile Thr Ile Thr Lys Ser Leu Asp Arg Glu Lys Gln
            35                  40                  45

Ala Arg Tyr Glu Ile Val Val Glu Ala Arg Asp Ala Gln Gly Leu Arg
        50                  55                  60

Gly Asp Ser Gly Thr Ala Thr Val Leu Val Thr Leu Gln Asp Ile Asn
 65                  70                  75                  80

Asp Asn Phe Pro
```

<210> SEQ ID NO 48
<211> LENGTH: 91
<212> TYPE: PRT
<213> ORGANISM: homo sapien

<400> SEQUENCE: 48

```
Leu Phe Val Glu Asp Pro Asp Glu Pro Gln Asn Arg Met Thr Lys Tyr
 1               5                  10                  15

Ser Ile Leu Arg Gly Asp Tyr Gln Asp Ala Phe Thr Ile Glu Thr Asn
                20                  25                  30

Pro Ala His Asn Glu Gly Ile Ile Lys Pro Met Lys Pro Leu Asp Tyr
            35                  40                  45

Glu Tyr Ile Gln Gln Tyr Ser Phe Ile Val Glu Ala Thr Asp Pro Thr
        50                  55                  60

Ile Asp Leu Arg Tyr Met Ser Pro Pro Ala Gly Asn Arg Ala Gln Val
 65                  70                  75                  80

Ile Ile Asn Ile Thr Asp Val Asp Glu Pro Pro
                85                  90
```

<210> SEQ ID NO 49
<211> LENGTH: 85
<212> TYPE: PRT
<213> ORGANISM: homo sapien

<400> SEQUENCE: 49

```
Val Leu Ala Met Asp Pro Asp Ala Ala Arg His Ser Ile Gly Tyr Ser
 1               5                  10                  15

Ile Arg Arg Thr Ser Asp Lys Gly Gln Phe Phe Arg Val Thr Lys Lys
                20                  25                  30

Gly Asp Ile Tyr Asn Glu Lys Glu Leu Asp Arg Glu Val Tyr Pro Trp
            35                  40                  45

Tyr Asn Leu Thr Val Glu Ala Lys Glu Leu Asp Ser Thr Gly Thr Pro
        50                  55                  60

Thr Gly Lys Glu Ser Ile Val Gln Val His Ile Glu Val Leu Asp Glu
```

```
                65                  70                  75                  80
Asn Asp Asn Ala Pro
                85

<210> SEQ ID NO 50
<211> LENGTH: 84
<212> TYPE: PRT
<213> ORGANISM: homo sapien

<400> SEQUENCE: 50

Ile Ser Ala Ile Asp Lys Asp Ile Thr Pro Arg Asn Val Lys Phe Lys
1               5                   10                  15

Phe Thr Leu Asn Thr Glu Asn Asn Phe Thr Leu Thr Asp Asn His Asp
                20                  25                  30

Asn Thr Ala Asn Ile Thr Val Lys Tyr Gly Gln Phe Asp Arg Glu His
            35                  40                  45

Thr Lys Val His Phe Leu Pro Val Val Ile Ser Asp Asn Gly Met Pro
        50                  55                  60

Ser Arg Thr Gly Thr Ser Thr Leu Thr Val Ala Val Cys Lys Cys Asn
65                  70                  75                  80

Glu Gln Gly Glu

<210> SEQ ID NO 51
<211> LENGTH: 732
<212> TYPE: PRT
<213> ORGANISM: homo sapien

<400> SEQUENCE: 51

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
                20                  25                  30

Val Glu Lys Glu Gly Leu Cys Asn Ala Cys Thr Trp Arg Gln Asn Thr
            35                  40                  45

Lys Ser Ser Arg Ile Glu Ala Ile Lys Ile Gln Ile Leu Ser Lys Leu
        50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
                100                 105                 110

Ala Thr Thr Glu Thr Ile Ile Thr Met Pro Thr Glu Ser Asp Phe Leu
            115                 120                 125

Met Gln Val Asp Gly Lys Pro Lys Cys Cys Phe Phe Lys Phe Ser Ser
        130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
210                 215                 220
```

-continued

```
Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
            245                 250                 255

Val Thr Asp Thr Pro Lys Ser Gly Asn Glu Asn Ser Glu Gln Lys Glu
                260                 265                 270

Asn Val Glu Lys Glu Gly Leu Cys Asn Ala Cys Thr Trp Arg Gln Asn
            275                 280                 285

Thr Lys Ser Ser Arg Ile Glu Ala Ile Lys Ile Gln Ile Leu Ser Lys
        290                 295                 300

Leu Arg Leu Glu Thr Ala Pro Asn Ile Ser Lys Asp Val Ile Arg Gln
305                 310                 315                 320

Leu Leu Pro Lys Ala Pro Pro Leu Arg Glu Leu Ile Asp Gln Tyr Asp
                325                 330                 335

Val Gln Arg Asp Asp Ser Ser Asp Gly Ser Leu Glu Asp Asp Asp Tyr
            340                 345                 350

His Ala Thr Thr Glu Thr Ile Ile Thr Met Pro Thr Glu Ser Asp Phe
        355                 360                 365

Leu Met Gln Val Asp Gly Lys Pro Lys Cys Cys Phe Phe Lys Phe Ser
370                 375                 380

Ser Lys Ile Gln Tyr Asn Lys Val Val Lys Ala Gln Leu Trp Ile Tyr
385                 390                 395                 400

Leu Arg Pro Val Glu Thr Pro Thr Thr Val Phe Val Gln Ile Leu Arg
                405                 410                 415

Leu Ile Lys Pro Met Lys Asp Gly Thr Arg Tyr Thr Gly Ile Arg Ser
            420                 425                 430

Leu Lys Leu Asp Met Asn Pro Gly Thr Gly Ile Trp Gln Ser Ile Asp
        435                 440                 445

Val Lys Thr Val Leu Gln Asn Trp Leu Lys Gln Pro Glu Ser Asn Leu
450                 455                 460

Gly Ile Glu Ile Lys Ala Leu Asp Glu Asn Gly His Asp Leu Ala Val
465                 470                 475                 480

Thr Phe Pro Gly Pro Gly Glu Asp Gly Leu Asn Pro Phe Leu Glu Val
                485                 490                 495

Lys Val Thr Asp Thr Pro Lys Ser Gly Asp Lys Thr His Thr Cys Pro
            500                 505                 510

Pro Cys Pro Ala Pro Glu Leu Leu Gly Gly Pro Ser Val Phe Leu Phe
        515                 520                 525

Pro Pro Lys Pro Lys Asp Thr Leu Met Ile Ser Arg Thr Pro Glu Val
530                 535                 540

Thr Cys Val Val Val Asp Val Ser His Glu Asp Pro Glu Val Lys Phe
545                 550                 555                 560

Asn Trp Tyr Val Asp Gly Val Glu Val His Asn Ala Lys Thr Lys Pro
                565                 570                 575

Arg Glu Glu Gln Tyr Asn Ser Thr Tyr Arg Val Val Ser Val Leu Thr
            580                 585                 590

Val Leu His Gln Asp Trp Leu Asn Gly Lys Glu Tyr Lys Cys Lys Val
        595                 600                 605

Ser Asn Lys Ala Leu Pro Ala Pro Ile Glu Lys Thr Ile Ser Lys Ala
610                 615                 620

Lys Gly Gln Pro Arg Glu Pro Gln Val Tyr Thr Leu Pro Pro Ser Arg
625                 630                 635                 640
```

-continued

```
Asp Glu Leu Thr Lys Asn Gln Val Ser Leu Thr Cys Leu Val Lys Gly
                645                 650                 655

Phe Tyr Pro Ser Asp Ile Ala Val Glu Trp Glu Ser Asn Gly Gln Pro
            660                 665                 670

Glu Asn Asn Tyr Lys Thr Thr Pro Pro Val Leu Asp Ser Asp Gly Ser
        675                 680                 685

Phe Phe Leu Tyr Ser Lys Leu Thr Val Asp Lys Ser Arg Trp Gln Gln
    690                 695                 700

Gly Asn Val Phe Ser Cys Ser Val Met His Glu Ala Leu His Asn His
705                 710                 715                 720

Tyr Thr Gln Lys Ser Leu Ser Leu Ser Pro Gly Lys
                725                 730

<210> SEQ ID NO 52
<211> LENGTH: 970
<212> TYPE: PRT
<213> ORGANISM: homo sapien

<400> SEQUENCE: 52

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Ser Gly Asn Glu Asn Ser Glu Gln Lys Glu
            260                 265                 270

Asn Val Glu Lys Glu Gly Leu Cys Asn Ala Cys Thr Trp Arg Gln Asn
        275                 280                 285
```

```
Thr Lys Ser Ser Arg Ile Glu Ala Ile Lys Ile Gln Ile Leu Ser Lys
    290                 295                 300

Leu Arg Leu Glu Thr Ala Pro Asn Ile Ser Lys Asp Val Ile Arg Gln
305                 310                 315                 320

Leu Leu Pro Lys Ala Pro Pro Leu Arg Glu Leu Ile Asp Gln Tyr Asp
                325                 330                 335

Val Gln Arg Asp Asp Ser Ser Asp Gly Ser Leu Glu Asp Asp Tyr
            340                 345                 350

His Ala Thr Thr Glu Thr Ile Ile Thr Met Pro Thr Glu Ser Asp Phe
                355                 360                 365

Leu Met Gln Val Asp Gly Lys Pro Lys Cys Cys Phe Phe Lys Phe Ser
    370                 375                 380

Ser Lys Ile Gln Tyr Asn Lys Val Val Lys Ala Gln Leu Trp Ile Tyr
385                 390                 395                 400

Leu Arg Pro Val Glu Thr Pro Thr Thr Val Phe Val Gln Ile Leu Arg
                405                 410                 415

Leu Ile Lys Pro Met Lys Asp Gly Thr Arg Tyr Thr Gly Ile Arg Ser
            420                 425                 430

Leu Lys Leu Asp Met Asn Pro Gly Thr Gly Ile Trp Gln Ser Ile Asp
    435                 440                 445

Val Lys Thr Val Leu Gln Asn Trp Leu Lys Gln Pro Glu Ser Asn Leu
    450                 455                 460

Gly Ile Glu Ile Lys Ala Leu Asp Glu Asn Gly His Asp Leu Ala Val
465                 470                 475                 480

Thr Phe Pro Gly Pro Gly Glu Asp Gly Leu Asn Pro Phe Leu Glu Val
                485                 490                 495

Lys Val Thr Asp Thr Pro Lys Ser Gly Lys Ser Pro Cys Gln Pro Asn
            500                 505                 510

Pro Cys His Gly Ala Ala Pro Cys Arg Val Leu Pro Glu Gly Gly Ala
        515                 520                 525

Gln Cys Glu Cys Pro Leu Gly Arg Glu Gly Thr Phe Cys Gln Thr Ala
    530                 535                 540

Ser Gly Gln Asp Gly Ser Gly Pro Phe Leu Ala Asp Phe Asn Gly Phe
545                 550                 555                 560

Ser His Leu Glu Leu Arg Gly Leu His Thr Phe Ala Arg Asp Leu Gly
                565                 570                 575

Glu Lys Met Ala Leu Glu Val Val Phe Leu Ala Arg Gly Pro Ser Gly
            580                 585                 590

Leu Leu Leu Tyr Asn Gly Gln Lys Thr Asp Gly Lys Gly Asp Phe Val
    595                 600                 605

Ser Leu Ala Leu Arg Asp Arg Arg Leu Glu Phe Arg Tyr Asp Leu Gly
    610                 615                 620

Lys Gly Ala Ala Val Ile Arg Ser Arg Glu Pro Val Thr Leu Gly Ala
625                 630                 635                 640

Trp Thr Arg Val Ser Leu Glu Arg Asn Gly Arg Lys Gly Ala Leu Arg
                645                 650                 655

Val Gly Asp Gly Pro Arg Val Leu Gly Glu Ser Pro Val Pro His Thr
            660                 665                 670

Val Leu Asn Leu Lys Glu Pro Leu Tyr Val Gly Gly Ala Pro Asp Phe
    675                 680                 685

Ser Lys Leu Ala Arg Ala Ala Ala Val Ser Ser Gly Phe Asp Gly Ala
    690                 695                 700
```

```
Ile Gln Leu Val Ser Leu Gly Gly Arg Gln Leu Leu Thr Pro Glu His
705                 710                 715                 720

Val Leu Arg Gln Val Asp Val Thr Ser Phe Ala Gly His Pro Cys Thr
                725                 730                 735

Arg Ala Ser Gly His Pro Cys Leu Asn Gly Ala Ser Cys Val Pro Arg
            740                 745                 750

Glu Ala Ala Tyr Val Cys Leu Cys Pro Gly Gly Phe Ser Gly Pro His
                755                 760                 765

Cys Glu Lys Gly Leu Val Glu Lys Ser Ala Gly Asp Val Asp Thr Leu
    770                 775                 780

Ala Phe Asp Gly Arg Thr Phe Val Glu Tyr Leu Asn Ala Val Thr Glu
785                 790                 795                 800

Ser Glu Leu Ala Asn Glu Ile Pro Val Glu Lys Ala Leu Gln Ser Asn
                805                 810                 815

His Phe Glu Leu Ser Leu Arg Thr Glu Ala Thr Gln Gly Leu Val Leu
                820                 825                 830

Trp Ser Gly Lys Ala Thr Glu Arg Ala Asp Tyr Val Ala Leu Ala Ile
                835                 840                 845

Val Asp Gly His Leu Gln Leu Ser Tyr Asn Leu Gly Ser Gln Pro Val
    850                 855                 860

Val Leu Arg Ser Thr Val Pro Val Asn Thr Asn Arg Trp Leu Arg Val
865                 870                 875                 880

Val Ala His Arg Glu Gln Arg Glu Gly Ser Leu Gln Val Gly Asn Glu
                885                 890                 895

Ala Pro Val Thr Gly Ser Ser Pro Leu Gly Ala Thr Gln Leu Asp Thr
                900                 905                 910

Asp Gly Ala Leu Trp Leu Gly Gly Leu Pro Glu Leu Pro Val Gly Pro
                915                 920                 925

Ala Leu Pro Lys Ala Tyr Gly Thr Gly Phe Val Gly Cys Leu Arg Asp
                930                 935                 940

Val Val Val Gly Arg His Pro Leu His Leu Leu Glu Asp Ala Val Thr
945                 950                 955                 960

Lys Pro Glu Leu Arg Pro Cys Pro Thr Pro
                965                 970

<210> SEQ ID NO 53
<211> LENGTH: 729
<212> TYPE: PRT
<213> ORGANISM: homo sapien

<400> SEQUENCE: 53

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
                20                  25                  30

Val Glu Lys Glu Gly Leu Cys Asn Ala Cys Thr Trp Arg Gln Asn Thr
            35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Asp Tyr His
                100                 105                 110
```

```
Ala Thr Thr Glu Thr Ile Ile Thr Met Pro Thr Glu Ser Asp Phe Leu
            115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
            195                 200                 205

Lys Thr Val Leu Gln Asn Trp Leu Lys Gln Pro Glu Ser Asn Leu Gly
            210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Ser Gly Lys Ser Pro Cys Gln Pro Asn Pro
            260                 265                 270

Cys His Gly Ala Ala Pro Cys Arg Val Leu Pro Glu Gly Gly Ala Gln
            275                 280                 285

Cys Glu Cys Pro Leu Gly Arg Glu Gly Thr Phe Cys Gln Thr Ala Ser
290                 295                 300

Gly Gln Asp Gly Ser Gly Pro Phe Leu Ala Asp Phe Asn Gly Phe Ser
305                 310                 315                 320

His Leu Glu Leu Arg Gly Leu His Thr Phe Ala Arg Asp Leu Gly Glu
                325                 330                 335

Lys Met Ala Leu Glu Val Val Phe Leu Ala Arg Gly Pro Ser Gly Leu
            340                 345                 350

Leu Leu Tyr Asn Gly Gln Lys Thr Asp Gly Lys Gly Asp Phe Val Ser
            355                 360                 365

Leu Ala Leu Arg Asp Arg Arg Leu Glu Phe Arg Tyr Asp Leu Gly Lys
370                 375                 380

Gly Ala Ala Val Ile Arg Ser Arg Glu Pro Val Thr Leu Gly Ala Trp
385                 390                 395                 400

Thr Arg Val Ser Leu Glu Arg Asn Gly Arg Lys Gly Ala Leu Arg Val
                405                 410                 415

Gly Asp Gly Pro Arg Val Leu Gly Glu Ser Pro Val Pro His Thr Val
            420                 425                 430

Leu Asn Leu Lys Glu Pro Leu Tyr Val Gly Gly Ala Pro Asp Phe Ser
            435                 440                 445

Lys Leu Ala Arg Ala Ala Ala Val Ser Ser Gly Phe Asp Gly Ala Ile
450                 455                 460

Gln Leu Val Ser Leu Gly Gly Arg Gln Leu Leu Thr Pro Glu His Val
465                 470                 475                 480

Leu Arg Gln Val Asp Val Thr Ser Phe Ala Gly His Pro Cys Thr Arg
                485                 490                 495

Ala Ser Gly His Pro Cys Leu Asn Gly Ala Ser Cys Val Pro Arg Glu
            500                 505                 510

Ala Ala Tyr Val Cys Leu Cys Pro Gly Gly Phe Ser Gly Pro His Cys
            515                 520                 525
```

-continued

```
Glu Lys Gly Leu Val Glu Lys Ser Ala Gly Asp Val Asp Thr Leu Ala
    530                 535                 540
Phe Asp Gly Arg Thr Phe Val Glu Tyr Leu Asn Ala Val Thr Glu Ser
545                 550                 555                 560
Glu Leu Ala Asn Glu Ile Pro Val Glu Lys Ala Leu Gln Ser Asn His
                565                 570                 575
Phe Glu Leu Ser Leu Arg Thr Glu Ala Thr Gln Gly Leu Val Leu Trp
            580                 585                 590
Ser Gly Lys Ala Thr Glu Arg Ala Asp Tyr Val Ala Leu Ala Ile Val
        595                 600                 605
Asp Gly His Leu Gln Leu Ser Tyr Asn Leu Gly Ser Gln Pro Val Val
    610                 615                 620
Leu Arg Ser Thr Val Pro Val Asn Thr Asn Arg Trp Leu Arg Val Val
625                 630                 635                 640
Ala His Arg Glu Gln Arg Glu Gly Ser Leu Gln Val Gly Asn Glu Ala
                645                 650                 655
Pro Val Thr Gly Ser Ser Pro Leu Gly Ala Thr Gln Leu Asp Thr Asp
            660                 665                 670
Gly Ala Leu Trp Leu Gly Gly Leu Pro Glu Leu Pro Val Gly Pro Ala
        675                 680                 685
Leu Pro Lys Ala Tyr Gly Thr Gly Phe Val Gly Cys Leu Arg Asp Val
    690                 695                 700
Val Val Gly Arg His Pro Leu His Leu Leu Glu Asp Ala Val Thr Lys
705                 710                 715                 720
Pro Glu Leu Arg Pro Cys Pro Thr Pro
                725

<210> SEQ ID NO 54
<211> LENGTH: 491
<212> TYPE: PRT
<213> ORGANISM: homo sapien

<400> SEQUENCE: 54

Met Gln Lys Leu Gln Leu Cys Val Tyr Ile Tyr Leu Phe Met Leu Ile
1               5                   10                  15
Val Ala Gly Pro Val Asp Leu Asn Glu Asn Ser Glu Gln Lys Glu Asn
            20                  25                  30
Val Glu Lys Glu Gly Leu Cys Asn Ala Cys Thr Trp Arg Gln Asn Thr
        35                  40                  45
Lys Ser Ser Arg Ile Glu Ala Ile Lys Ile Gln Ile Leu Ser Lys Leu
    50                  55                  60
Arg Leu Glu Thr Ala Pro Asn Ile Ser Lys Asp Val Ile Arg Gln Leu
65                  70                  75                  80
Leu Pro Lys Ala Pro Pro Leu Arg Glu Leu Ile Asp Gln Tyr Asp Val
                85                  90                  95
Gln Arg Asp Asp Ser Ser Asp Gly Ser Leu Glu Asp Asp Asp Tyr His
            100                 105                 110
Ala Thr Thr Glu Thr Ile Ile Thr Met Pro Thr Glu Ser Asp Phe Leu
        115                 120                 125
Met Gln Val Asp Gly Lys Pro Lys Cys Cys Phe Phe Lys Phe Ser Ser
    130                 135                 140
Lys Ile Gln Tyr Asn Lys Val Val Lys Ala Gln Leu Trp Ile Tyr Leu
145                 150                 155                 160
Arg Pro Val Glu Thr Pro Thr Thr Val Phe Val Gln Ile Leu Arg Leu
                165                 170                 175
```

```
Ile Lys Pro Met Lys Asp Gly Thr Arg Tyr Thr Gly Ile Arg Ser Leu
            180             185             190

Lys Leu Asp Met Asn Pro Gly Thr Gly Ile Trp Gln Ser Ile Asp Val
            195             200             205

Lys Thr Val Leu Gln Asn Trp Leu Lys Gln Pro Glu Ser Asn Leu Gly
            210             215             220

Ile Glu Ile Lys Ala Leu Asp Glu Asn Gly His Asp Leu Ala Val Thr
225             230             235             240

Phe Pro Gly Pro Gly Glu Asp Gly Leu Asn Pro Phe Leu Glu Val Lys
            245             250             255

Val Thr Asp Thr Pro Lys Ser Gly Asp Lys Thr His Thr Cys Pro Pro
            260             265             270

Cys Pro Ala Pro Glu Leu Leu Gly Gly Pro Ser Val Phe Leu Phe Pro
            275             280             285

Pro Lys Pro Lys Asp Thr Leu Met Ile Ser Arg Thr Pro Glu Val Thr
            290             295             300

Cys Val Val Val Asp Val Ser His Glu Asp Pro Glu Val Lys Phe Asn
305             310             315             320

Trp Tyr Val Asp Gly Val Glu Val His Asn Ala Lys Thr Lys Pro Arg
            325             330             335

Glu Glu Gln Tyr Asn Ser Thr Tyr Arg Val Val Ser Val Leu Thr Val
            340             345             350

Leu His Gln Asp Trp Leu Asn Gly Lys Glu Tyr Lys Cys Lys Val Ser
            355             360             365

Asn Lys Ala Leu Pro Ala Pro Ile Glu Lys Thr Ile Ser Lys Ala Lys
            370             375             380

Gly Gln Pro Arg Glu Pro Gln Val Tyr Thr Leu Pro Pro Ser Arg Asp
385             390             395             400

Glu Leu Thr Lys Asn Gln Val Ser Leu Thr Cys Leu Val Lys Gly Phe
            405             410             415

Tyr Pro Ser Asp Ile Ala Val Glu Trp Glu Ser Asn Gly Gln Pro Glu
            420             425             430

Asn Asn Tyr Lys Thr Thr Pro Pro Val Leu Asp Ser Asp Gly Ser Phe
            435             440             445

Phe Leu Tyr Ser Lys Leu Thr Val Asp Lys Ser Arg Trp Gln Gln Gly
            450             455             460

Asn Val Phe Ser Cys Ser Val Met His Glu Ala Leu His Asn His Tyr
465             470             475             480

Thr Gln Lys Ser Leu Ser Leu Ser Pro Gly Lys
            485             490
```

METHOD OF TREATING A MUSCLE-RELATED CONDITION WITH MODIFIED IGF1 POLYPEPTIDES

CROSS-REFERENCE TO RELATED APPLICATIONS

This application is a divisional of U.S. patent application Ser. No. 10/954,468, filed 30 Sep. 2004, now U.S. Pat. No. 7,355,018, which claims the benefit under 35 USC 119(e) of U.S. Provisional Application Nos. 60/507,168 filed 30 Sep. 2003, 60/516,806 filed 3 Nov. 2003, 60/573,525 filed 21 May 2004, 60/534,819 filed 7 Jan. 2004, 60/584,956 filed 2 Jul. 2004, 60/529,826 filed 16 Dec. 2003, 60/534,654 filed 7 Jan. 2004, 60/581,833 filed 22 Jun. 2004, and 60/554,640 filed 19 Mar. 2004, which applications are herein incorporated by reference in their entirety.

BACKGROUND OF THE INVENTION

Field of the Invention

This invention relates to therapeutic fusion proteins, methods of producing such fusion proteins, and methods for treating, diagnosing, or monitoring diseases or conditions using these proteins.

BRIEF SUMMARY OF THE INVENTION

In the broadest embodiment, the present invention comprises compositions and methods for delivering one or more active or therapeutic agent(s). In one embodiment, the present invention provides compositions and methods for specifically delivering one or more active or therapeutic agent(s) to a pre-selected target site. In this embodiment, the present invention provides fusion polypeptides capable of delivering one or more active or therapeutic agent(s) to a target site defined by the presence of one or more expressed cell surface proteins. The targeting fusion polypeptides are therapeutically useful, as well as useful in a variety of in vitro and in vivo diagnostic and prognostic assays.

In a first aspect, the invention provides a targeting fusion polypeptide comprising (i) a targeting ligand, or derivative or fragment thereof, capable of binding specifically to a pre-selected cell surface protein, and (ii) an active or therapeutic agent. In specific embodiments, the targeting fusion polypeptide optionally further comprises (iii) a multimerizing component capable of forming a multimer with another targeting fusion polypeptide, and/or (iv) a signal sequence.

In a second aspect, the invention provides a muscle-targeting fusion polypeptide, comprising (i) a targeting ligand, or derivative or fragment thereof, capable of binding specifically to a muscle cell surface protein, and (ii) an active or therapeutic agent. In specific embodiments, the muscle-targeting fusion polypeptide optionally further comprises (iii) a multimerizing component capable of forming a multimer with another targeting fusion polypeptide, and/or (iv) a signal sequence.

In specific embodiments, the muscle-targeting ligand specifically binds a muscle surface protein, such as a receptor. In a more specific embodiment, the muscle surface receptor is MuSK. In an even more specific embodiment, the muscle-targeting fusion polypeptide specifically targets skeletal muscle, and comprises a MuSK ligand, or fragment of a MuSK ligand capable of binding the MuSK receptor. In specific embodiments, the MuSK-specific ligand is agrin or a fragment or derivative thereof capable of binding MuSK, or an anti-MuSK antibody or fragment or derivative thereof, including, for example, an scFv.

In other specific embodiments, the muscle-targeting ligand of the muscle-targeting fusion polypeptide comprises three or more muscle cadherin (M-cadherin) extracellular cadherin domains, or derivatives or fragments thereof, capable of binding specifically to a muscle cells or other cells that express homophilic muscle cadherins. In one specific embodiment, the muscle-targeting ligand consists essentially of the first three (3) or four (4) N-terminal extracellular domains of M-cadherin.

The active or therapeutic agent may be any agent that is desirable to deliver to a pre-selected site for therapeutic purposes. In specific embodiments, the active or therapeutic agent is a ligand for a second cell surface receptor, and is capable of binding and activating a second receptor. In other embodiments, the active or therapeutic agent is an agent capable of blocking the activity of another agent that is active on the target cell. In a specific embodiment, the active or therapeutic agent is selected from the group consisting of IL-15, myotrophin, urocortin, urocortin II, a natural or mutant IGF-1 or IGF-2, insulin, the pro domain of myostatin, hGH, proliferin, follistatin, FSTL1, and FLRG, and a biologically active fragments thereof.

In one specific embodiment, the invention provides a muscle-targeting fusion polypeptide, comprising (i) agrin, or a fragment or derivative thereof capable of binding the MuSK receptor; and (ii) an active or therapeutic agents selected from the group consisting of IL-15, myotrophin, urocortin, urocortin II, a natural or mutant IGF-1 or IGF-2, insulin, the pro domain of myostatin, hGH, proliferin, follistatin, FSTL1, and FLRG, or a biologically active fragment thereof; and optionally (iii) a multimerizing component, and/or (iv) a signal sequence. In another specific embodiment, the invention provides a muscle-targeting fusion polypeptide comprising (i) three (3) N-terminal extracellular domains of M cadherin; and (ii) an active or therapeutic agents selected from the group consisting of IL-15, myotrophin, urocortin, urocortin II, a natural or mutant IGF-1 or IGF-2, insulin, the pro domain of myostatin, hGH, proliferin, follistatin, FSTL1, and FLRG, or a biologically active fragment thereof; and optionally (iii) a multimerizing component, and/or (iv) a signal sequence.

In a separate embodiment, the invention provides composition for delivering two active or therapeutic agents. The two active or therapeutic agents may act synergistically when present together. Accordingly, in a third aspect, the invention features a fusion polypeptide comprising (i) a first active or therapeutic agent, and (ii) a second active or therapeutic agent. In specific embodiments, the fusion polypeptide optionally further comprises (iii) a multimerizing component capable of forming a multimer with another targeting fusion polypeptide, and/or (iv) a signal sequence. In a preferred embodiment, one active or therapeutic agent is natural or mutant human growth hormone (hGH) or proliferin, or a biologically active fragment thereof and the other agent is natural or mutant IGF-1 or IGF-2, or a biologically active fragment thereof.

In another embodiment, the invention provides compositions for delivering IGF-related polypeptides, which may be used alone or as a components of the targeting or therapeutic fusion molecules described herein. Such polypeptides comprise a mutant IGF-1 or IGF-2 molecule having (i) deletion of the first three amino acids ($\Delta 3$), or substitution of either arginine (R) or alanine (A) for glutamic acid (E) at position 3 (E3R or E3A); and (ii) modification in the double arginines (RR) at positions 36 and 37 by either substitution of an alanine (A) for an arginine (A) at position 36 or 37 or deletion of R36 (del36) or R37 (del37); wherein the IGF-derived polypeptides optionally comprise (iii) a multimerizing component capable of forming a multimer with another IGF-related polypeptide, and/or (iv) a signal sequence.

In other embodiment, the invention provides compositions for delivering myostatin-inhibiting fusion polypeptides, which may be used alone or as components of the targeting or therapeutic fusion molecules described herein. Such compositions comprise the propeptide of human myostatin. In one specific embodiment, the fusion proteins comprise the propeptide of myostatin fused to a multimerizing component, such as the Fc domain of IgG.

In a fourth aspect, the invention features a targeting fusion polypeptide comprising (i) a targeting ligand, or derivative or fragment thereof, capable of binding specifically to a preselected cell surface protein, (ii) a first active or therapeutic agent, and (ii) a second active or therapeutic agent. In specific embodiments, the fusion polypeptide optionally further comprises (iii) a multimerizing component capable of forming a multimer with another targeting fusion polypeptide, and/or (iv) a signal sequence. In a preferred embodiment, one active or therapeutic agent is natural or mutant human growth hormone (hGH) or proliferin, or a biologically active fragment thereof and the other agent is natural or mutant IGF-1 or IGF-2, or a biologically active fragment thereof. In one preferred embodiment, the targeting ligand is agrin, one active agent is IGF1 or mutant thereof, and one active agent is hGH, such as in the targeting fusion polypeptides of SEQ ID NOS: 23-26.

In one embodiment, the targeting fusion polypeptide is a muscle-targeting fusion polypeptide, comprising (i) a targeting ligand, or derivative or fragment thereof, capable of binding specifically to a muscle cell surface protein, (ii) a first active or therapeutic agent, and (ii) a second active or therapeutic agent, optionally further comprises (iii) a multimerizing component capable of forming a multimer with another targeting fusion polypeptide, and/or (iv) a signal sequence. In a preferred embodiment, one active or therapeutic agent is natural or mutant human growth hormone (hGH), or a biologically active fragment thereof and another active or therapeutic agent is natural or mutant IGF-1 or IGF-2, or a biologically active fragment thereof.

In a specific embodiment, the muscle-targeting fusion polypeptide comprises (i) agrin, or a fragment or derivative thereof capable of binding the MuSK receptor; and (ii) a first active or therapeutic agent, wherein the first active or therapeutic agent is natural or mutant human growth hormone or a biologically active fragment thereof; (iii) a second active or therapeutic agent, wherein the second active or therapeutic agent is natural or mutant IGF-1 or IGF-2, or a biologically active fragment thereof; and optionally (iv) a multimerizing component, and/or (v) a signal sequence. In another embodiment, the muscle-targeting fusion polypeptide comprises a sequence selected from the group consisting of SEQ ID NOS: 9-31. In preferred embodiments, the muscle-targeting fusion polypeptide comprises a sequence selected from the group consisting of SEQ ID NOS:26-29.

In a fifth aspect, the invention provides an IGF-related polypeptide comprising a mutant IGF-1 or IGF-2 molecule having (i) deletion of the first three amino acids (Δ3), or substitution of either arginine (R) or alanine (A) for glutamic acid (E) at position 3; and (ii) modification in the double arginines (RR) at positions 36 and 37 by either substitution of an alanine (A) at position 36 or position 37 or deletion or R36 or R37; wherein the IGF-derived polypeptides optionally comprise (iii) a multimerizing component capable of forming a multimer with another IGF-related polypeptide, and/or (iv) a signal sequence.

In a sixth aspect, the invention provides a fusion polypeptide comprising the propeptide of human myostatin fused to a multimerizing component, such as the Fc domain of IgG.

In specific embodiments wherein the fusion polypeptides of the invention comprise a multimerizing component, the multimerizing component may be selected from the group consisting of (i) a multimerizing component comprising a cleavable region (C-region), (ii) a truncated multimerizing component, (iii) an amino acid sequence between 1 to about 500 amino acids in length, optionally comprising at least one cysteine residue, (iv) a leucine zipper, (v) a helix loop motif, (vi) a coil-coil motif, (vii) an Fc-protein, and (viii) a combination thereof. In specific embodiments in which the targeting fusion polypeptide comprises a signal sequence, the signal sequence may comprise any sequence known to a skilled artisan for directing secretion of a polypeptide or protein from a cell, include natural or synthetic sequences. Generally, a signal sequence is placed at the beginning or amino-terminus of the fusion polypeptide of the invention. Such a signal sequence may be native to the cell, recombinant, or synthetic.

The components of the fusion polypeptides of the invention may be connected directly to each other or connected via one or more spacer sequences. In one preferred embodiment, the components are fused directly to each other. In another preferred embodiment, the components are connected with a nucleic acid sequence encoding a spacer of 1-200 amino acids. Any spacer known to the art may be used to connect the polypeptide components. A spacer sequence may also include a sequence used to enhance expression of the fusion polypeptide, provide restriction sites, and allow component domains to form optimal tertiary and quaternary structures and/or to enhance the interaction of a component with its receptor. In one embodiment, the fusion polypeptide of the invention comprises one or more peptide sequences between one or more components which is (are) between 1-25 amino acids.

The components of the fusion polypeptide of the invention may be arranged in a variety of configurations. For example, the targeting ligand component (1), the active or therapeutic agent(s) component (2), and the optional multimerizing component (3) may be arranged in one of the following configurations: 1-2; 2-1; 1-2-3; 1-3-2; 3-1-2; 2-1-3; 2-3-1, or 3-2-1. Still further, multiple components of a targeting ligand or active agent may be included in the fusion polypeptide, e.g., 1-1-2, 2-1-1, 1-2-1, 2-2-1, 1-1-2-1-1, etc.

When the active or therapeutic agent(s) component of the fusion polypeptide of the invention comprises two active or therapeutic agents, these agents may be arranged in a variety of configurations. For example, active agent (1) and agent (2) may be arrange either 1-2 or 2-1. Still further, the same agent may be included more than once in the component, e.g., 1-1-2; 1-2-2; 1-2-1, etc.

In a seventh aspect, the invention provides nucleic acid molecules encoding the fusion polypeptides of the invention.

In related aspects, the invention features a vector comprising a nucleic acid molecule of the invention, including expression vectors comprising the nucleic acid molecules operatively linked to an expression control sequence, and host-vector systems for the production of a fusion polypeptide which comprise the expression vector, in a suitable host cell; host-vector systems wherein the suitable host cell is, without limitation, a bacterial, yeast, insect, or mammalian cell. Examples of suitable cells include *E. coli, B. subtilis*, BHK, COS and CHO cells. Additionally encompassed are fusion polypeptides of the invention modified by acetylation or pegylation. Methods for acetylating or pegylating a protein are well known in the art.

The invention further provides a method of producing a fusion polypeptide of the invention, comprising culturing a host cell transfected with a vector comprising a nucleic acid molecule of the invention, under conditions suitable for expression of the protein from the host cell, and recovering the polypeptide so produced.

The invention features therapeutic methods for the treatment of a disease or condition, comprising administering a therapeutically effective amount of a fusion protein of the invention to a subject in need thereof, or a subject at risk for development of that disease or condition. When the disease or condition is a muscle condition, such as atrophy, the therapeutic method of the invention comprises administering a therapeutically effective amount of a muscle-targeting fusion protein of the invention to a subject in need thereof, wherein the muscle-related disease or condition is ameliorated or inhibited. In one specific embodiment, the invention features a method of inhibiting or ameliorating muscle atrophy, comprising administering a therapeutically effective amount of a fusion polypeptide comprising IGF-1 and agrin, or biologically active fragments or derivatives of IGF-1 and/or agrin, wherein IGF-1 is specifically delivered to the desired site by agrin binding to the muscle-specific surface receptor MuSK. In another embodiment, the muscle-specific fusion polypeptide comprises agrin and IL-15, or biologically active fragments or derivatives of agrin and/or IL-15. In another embodiment, the muscle-specific fusion polypeptide comprises agrin; natural or mutant hGH, or a biologically active fragment or a derivative thereof; and natural or mutant IGF-1, or a biologically active fragment or a derivative thereof. In yet another embodiment, the muscle-specific fusion polypeptide comprises agrin; natural or mutant hGH, or a biologically active fragment or a derivative thereof; and natural or mutant IGF-2, or a biologically active fragment or a derivative thereof. The muscle-related condition or disorder treated by the fusion polypeptides of the invention may arise from a number of sources, including for example: denervation; degenerative, metabolic or inflammatory neuropathy; infantile and juvenile spinal muscular atrophies; autoimmune motor neuropathy; from chronic disease, including cachexia resulting from cancer, AIDS, fasting or rhabdomyolysis; and from muscular dystrophy syndromes such as Duchenne.

Accordingly, in a seventeenth aspect, the invention features pharmaceutical compositions comprising a targeting fusion protein of the invention with a pharmaceutically acceptable carrier. Such pharmaceutical compositions may comprise the fusion proteins or nucleic acids which encode them. In specific embodiments, the pharmaceutical composition of the invention comprises a muscle-targeting polypeptide comprising (i) agrin, or a biologically active fragment or derivative thereof, capable of binding the muscle-specific surface protein MuSK, and (ii) an active agent selected from the group consisting of insulin like growth factor 1 (IGF-1) and interleukin-15 (IL-15), optionally further comprising (iii) a multimerizing component, together with a pharmaceutically acceptable carrier. In another embodiment, the pharmaceutical composition of the invention comprises a muscle-targeting polypeptide comprising (i) agrin, or a fragment or derivative thereof capable of binding the MuSK receptor; and (ii) a first active or therapeutic agent, wherein the first active or therapeutic agent is natural or mutant human growth hormone or proliferin, or a biologically active fragment thereof; (iii) a second active or therapeutic agent, wherein the second active or therapeutic agent is natural or mutant IGF-1 or IGF-2, or a biologically active fragment thereof; and optionally (iv) a multimerizing component, together with a pharmaceutically acceptable carrier.

The invention features a method of activating and/or phosphorylation multiple cell surface receptors simultaneously, by providing a fusion polypeptide capable of binding multiple cell surface receptor to a cell expressing multiple receptors. In one embodiment, the invention features a fusion polypeptide capable of binding both MuSK and IGF-R. In another embodiment, the invention provides a fusion polypeptide capable of binding both GHR and IFG-R. In yet another embodiment, the invention provides a fusion polypeptide capable of binding MuSK, GHR, and IGF-R simultaneously. Preferably, the method of the invention is achieved by providing a targeting fusion polypeptide described above.

Other objects and advantages will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, references to "a method" include one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference.

General Description

The invention encompasses fusion polypeptides and nucleic acids that encode them which comprise one or more active or therapeutic agent(s). The invention further provides targeting fusion polypeptides and nucleic acids which encode then comprise a targeting ligand that specifically binds a pre-selected cell surface protein, such as a receptor, and one or more active or therapeutic agent(s) capable of achieving a desired effect when delivered to the desired cell or tissue.

Definitions

"Biologically active" fragments or derivatives of a targeting ligand or an active or therapeutic component of the targeting fusion polypeptides of the invention encompass any naturally occurring molecule, or mutant or derivative thereof capable of achieving the desired effect at the target site. For example, when the active or therapeutic agent is IGF-1, the invention envisions the use of a mutant or derivative IGF-1 molecule capable of binding the IGF-1 receptor. Examples of such mutants, which retain the activity of the native molecule but which have greater stability and potency, are described herein. A "biologically active" fragment of derivative of any targeting component is any portion or mutant thereof capable of binding the target cell. Thus, for example, when the targeting ligand is agrin, a biologically active fragment or derivative is any portion or mutant of agrin capable of binding the MuSK receptor.

The terms "treatment", "treating", and the like are used herein to generally mean obtaining a desired pharmacologic and/or physiologic effect. The effect may be prophylactic in terms of completely or partially preventing a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; or (c) relieving the disease or condition, i.e., causing regression of the disease or condition. The population of subjects treated by the method of the disease includes subject suffering from the undesirable condition or disease, as well as subjects at risk for development of the condition or disease.

By the term "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

As used herein, a "condition or disease" generally encompasses a condition of a mammalian host, particularly a human host, which is undesirable and/or injurious to the host. Thus, treating a muscle-related condition with a fusion polypeptide which specifically targets skeletal muscle will encompass the treatment of a mammal, in particular, a human, who has symptoms reflective of decreased target muscle receptor activation, or who is expected to have such decreased levels in response to a disease, condition or treatment regimen. Treating a muscle-related condition or disease encompasses the treatment of a human subject wherein enhancing the activation of a target muscle receptor with the muscle specific fusion polypeptide of the invention results in amelioration of an undesirable symptom resulting from the muscle-related condition or disease. As used herein, a "muscle-related condition" also includes a condition in which it is desirable to alter, either transiently, or long-term, activation of a particular target muscle receptor.

Targeting Fusion Polypeptide Components

The first component of the targeting fusion polypeptides of the invention is a targeting ligand. A targeting ligand is a molecule, e.g., a protein or fragment thereof that specifically binds with high affinity to a target on a pre-selected cell, such as a surface protein such as a receptor that is present to a greater degree on the pre-selected cell target than on any other body tissue. For example, as described in U.S. Pat. Nos. 5,814,478 and 6,413,740, the MuSK receptor is highly specific to muscle. Accordingly, the cognate ligand agrin, as well as MuSK binding portions thereof is an example of a targeting ligand useful as a first component in the fusion polypeptides of the present invention. Another example of a targeting ligand is a group of cadherin domains from a human cadherin. Accordingly, human cadherin domains from, for example, human muscle cadherin may be used in the targeting fusion polypeptides of the invention to target muscle cells. The targeting ligand component of the fusion polypeptide of the invention may include a naturally occurring or engineered ligand, or a fragment thereof, capable of binding the pre-selected target cell.

In another embodiment of the invention, the first component targeting ligand of the targeting fusion polypeptides of the invention consists of at least three, four or five cadherin domains, or derivatives or fragments thereof, capable of binding specifically to target cells that express homophilic cadherins. By the term "cadherin" is meant a molecule that is a member of a family of calcium-dependent cell-cell adhesion molecules consisting of several distinct proteins. Several human cadherins have been identified and characterized, including, but not limited to, vascular endothelial cadherin (VE-cadherin; Ludwig et al. (2000) Mamm. Genome 11(11): 1030-1033), nerve cadherin (N-cadherin; Reid et al. (1990) J. Nucleic Acids Res. 18 (19), 5896), muscle cadherin (M-cadherin; Shimoyama et al. (1998) J. Biol. Chem. 273(16): 10011-10018; Shibata et al. (1997) J. Biol. Chem. 272(8): 5236-5270), liver-intestine cadherin (Cadherin-17; Dantzig et al. (1994) Science 264(5157):430-433), heart cadherin (Cadherin-13; Tanihara et al. (1994) Cell Adhes. Commun. 2(1):15-26), tissue-lung cadherin (Cadherin-26; Ota et al. (2004) Nat. Genet. 36(1):40-45), Cadherin-24 (Katafiasz et al. (2003) J. Biol. Chem. 278(30):27513-27519; Clark et al. (2003) Genome Res. 13(10):2265-2270), and epithelial cadherin (E-cadherin; Cadherin-1; Bussemakers et al. (1993) Mol. Biol. Rep. 17(2):123-128).

Typically, each cadherin molecule consists of an extracellular domain, which consists of five (5) cadherin domains, as well as a transmembrane domain and intracellular domain. The extracellular cadherin domains interact with homophilic cadherins on adjacent cells, thus cadherins act as both ligands and receptors. Cadherins are also believed to exclude or repel heterophilic cadherins on adjacent cells. A common feature of human cadherins is the presence of 5 tandomly repeated cadherin domains. Such cadherin domains bind to homophilic cadherin domains on adjacent cells, thus causing cell-cell adhesion.

As described herein, applicants have discovered that the ability of cadherin domains to attract homophilic cadherins can be used to create targeting molecules that are directed to specific cell types. Further, such cell-cell adhesion can be mimicked using a minimum of three and up to five cadherin domains from any human cadherin. Accordingly, constructs are provided which utilize the specificity of cadherin domains to target the fusion polypeptides of the invention to specific cells. Thus, for example, if the desired target is muscle tissue, a fusion polypeptide of the invention would comprise at least three cadherin domains from the extracellular domain of human M-cadherin (or biologically active fragments or derivatives thereof that are capable of binding homophilic M-cadherin), fused to a second component that is active on muscle cells. Alternatively, if the desired target were heart tissue, the first component would comprise at least three cadherin domains from the extracellular domain of H-cadherin, or biologically active fragments or derivatives thereof that are capable of binding homophilic H-cadherin.

Further examples of targeting ligands also include, but are not limited to, antibodies and portions thereof that bind a pre-selected cells surface protein with high affinity. By "high affinity" is meant an equilibrium dissociation constant of at least $10^{-7}$ molar, as determined by assay methods known in the art, for example, BiaCore analysis. In one embodiment, the targeting ligand component of the targeting fusion polypeptides of the invention may also comprise one or more immunoglobulin binding domains isolated from antibodies generated against a selected tissue-specific surface protein or target tissue-specific receptor. The term "immunoglobulin or antibody" as used herein refers to a mammalian, including human, polypeptide comprising a framework region from an immunoglobulin gene or fragments thereof that specifically binds and recognizes an antigen, which, in the case of the present invention, is a tissue-specific surface protein, a target tissue-specific receptor, or portion thereof. If the intended targeting fusion polypeptide will be used as a mammalian therapeutic, immunoglobulin binding regions should be derived from the corresponding mammalian immunoglobulins. If the targeting fusion polypeptide is intended for non-therapeutic use, such as for diagnostics and ELISAs, the immunoglobulin binding regions may be derived from either human or non-human mammals, such as mice. The human immunoglobulin genes or gene fragments include the kappa, lambda, alpha, gamma, delta, epsilon, and mu constant regions, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Within each IgG class, there are different isotypes (e.g. $IgG_1$, $IgG_2$, etc.). Typically, the antigen-binding region of an antibody will be the most critical in determining specificity and affinity of binding.

An exemplary immunoglobulin (antibody) structural unit of human IgG, comprises a tetramer. Each tetramer is composed of two identical pairs of polypeptide chains, each pair having one light chain (about 25 kD) and one heavy chain (about 50-70 kD). The N-terminus of each chain defines a variable region of about 100-110 or more amino acids primarily responsible for antigen recognition. The terms "variable light chain" ($V_L$) and variable heavy chain ($V_H$) refer to these light and heavy chains respectively.

Antibodies exist as intact immunoglobulins, or as a number of well-characterized fragments produced by digestion with various peptidases. For example, pepsin digests an antibody below the disulfide linkages in the hinge region to produce $F(ab)'_2$, a dimer of Fab which itself is a light chain joined to $V_H$—$C_H$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the terms immunoglobulin or antibody, as used herein, also includes antibody fragments either produced by the modification of whole antibodies, or those synthesized de novo using recombinant DNA methodologies (e.g., single chain Fv)(scFv)) or those identified using phage display libraries (see, for example, McCafferty et al. (1990) Nature 348:552-554). In addition, the fusion polypeptides of the invention include the variable regions of the heavy ($V_H$) or the light ($V_L$) chains of immunoglobulins, as well as tissue-specific surface protein and target receptor-binding portions thereof. Methods for producing such variable regions are described in Reiter, et al. (1999) J. Mol. Biol. 290:685-698.

Methods for preparing antibodies are known to the art. See, for example, Kohler & Milstein (1975) Nature 256:495-497; Harlow & Lane (1988) *Antibodies: a Laboratory Manual*, Cold Spring Harbor Lab., Cold Spring Harbor, N.Y.). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity. Techniques for the production of single chain antibodies or recombinant antibodies (U.S. Pat. No. 4,946,778; U.S. Pat. No. 4,816,567) can be adapted to produce antibodies used in the fusion polypeptides and methods of the instant invention. Also, transgenic mice, or other organisms such as other mammals, may be used to express human or humanized antibodies. Alternatively, phage display technology can be used to identify antibodies, antibody fragments, such as variable domains, and heteromeric Fab fragments that specifically bind to selected antigens.

Screening and selection of preferred immunoglobulins (antibodies) can be conducted by a variety of methods known to the art. Initial screening for the presence of monoclonal antibodies specific to a tissue-specific or target receptor may be conducted through the use of ELISA-based methods or phage display, for example. A secondary screen is preferably conducted to identify and select a desired monoclonal antibody for use in construction of the tissue-specific fusion polypeptides of the invention. Secondary screening may be conducted with any suitable method known to the art. One preferred method, termed "Biosensor Modification-Assisted Profiling" ("BiaMAP") is described in US patent publication 2004/101920, herein specifically incorporated by reference in its entirety. BiaMAP allows rapid identification of hybridoma clones producing monoclonal antibodies with desired characteristics. More specifically, monoclonal antibodies are sorted into distinct epitope-related groups based on evaluation of antibody: antigen interactions.

Active or Therapeutic Agent

Another component of the fusion polypeptides of the invention is an active or therapeutic agent or mutant or derivative thereof, i.e. a molecule capable of having a desired effect when delivered to the pre-selected target site, e.g., cell or tissue, Active or therapeutic agents, include, but are not limited to, small molecules, hormones, growth factors, therapeutic biologics, activating antibodies and portions thereof, and blocking antibodies and portions thereof, that are capable of having a desirable effect upon delivery to a target cell or tissue.

In particular embodiments wherein the targeting fusion polypeptide is directed at muscle cells or tissue, the fusion polypeptide comprises a targeting ligand, and a therapeutic agent that is active on muscle cells. Such agents include, but are not limited to, insulin, IL-15, myotrophin, urocortin, urocortin II, human myostatin propeptide, IGF-1, hGH, proliferin, follistatin, FSTL1, and FLRG, or mutants, derivative, or fragments thereof having biologically activity. In addition, the active or therapeutic agent may comprise a blocking antibody or biologically active derivative thereof, which blocks, for example, myostatin, activin receptor, BMP receptor 1, TNF receptor and IL-1 receptor. Alternatively, the active or therapeutic agent may comprise an activating antibody that activates, for example, the IFG1 receptor, B2adrenergic receptor or the IL-15 receptor complex.

In embodiments wherein the targeting fusion polypeptide is directed at vascular endothelial cells, the fusion polypeptide comprises a targeting ligand, for example, at least 3 cadherin domains of human VE-cadherin and a therapeutic agent that is active on endothelial cells, such as angiopoietin or VEGF, or activating or blocking antibodies or portions thereof.

Optional Multimerizing Component

In specific embodiments, the fusion polypeptides of the invention comprise a multimerizing component. A multimerizing component includes any natural or synthetic sequence capable of interacting with another multimerizing component to form a higher order structure, e.g., a dimer, a trimer, etc. The multimerizing component may be selected from the group consisting of (i) a multimerizing component comprising a cleavable region (C-region), (ii) a truncated multimerizing component, (iii) an amino acid sequence between 1 to about 500 amino acids in length, (iv) a leucine zipper, (v) a helix loop motif, and (vi) a coil-coil motif. When the multimerizing component comprises an amino acid sequence between 1 to about 500 amino acids in length, the sequence may contain one or more cysteine residues capable of forming a disulfide bond with a corresponding cysteine residue on another fusion polypeptide comprising a multimerizing component with one or more cysteine residues. In some embodiments, the multimerizing component comprises an immunoglobulin-derived domain from, for example, human IgG, IgM or IgA, or comparable immunoglobulin domains from other animals, including, but not limited to, mice. In specific embodiments, the immunoglobulin-derived domain may be selected from the group consisting of the constant region of IgG, the Fc domain of IgG, an Fc-protein, the heavy chain of IgG, and the light chain of IgG. The Fc domain of IgG may be selected from the isotypes IgG1, IgG2, IgG3, and IgG4, as well as any allotype within each isotype group.

Optional Component Spacers

The components of the targeting fusion polypeptides of the invention may be connected directly to each other or be connected via spacers. The term "spacer" or "linker" means one or more molecules, e.g., nucleic acids or amino acids, or non-peptide moieties, such as polyethylene glycol, which may be inserted between one or more component domains. For example, spacer sequences may be used to provide a restriction site between components for ease of manipulation. A spacer may also be provided to enhance expression of the fusion polypeptide from a host cell, to decrease steric hindrance such that the component may assume its optimal tertiary or quaternary structure and/or interact appropriately with its target molecule. For spacers and methods of identifying desirable spacers, see, for example, George et al. (2003) Protein Engineering 15:871-879, herein specifically incorporated by reference.

A spacer sequence may include one or more amino acids naturally connected to a receptor component, or may be an added sequence used to enhance expression of the fusion protein, provide specifically desired sites of interest, allow component domains to form optimal tertiary structures and/or to enhance the interaction of a component with its target molecule. In one embodiment, the spacer comprises one or more peptide sequences between one or more components which is (are) between 1-100 amino acids, preferably 1-25. In one specific embodiment, the spacer is a three amino acid sequence; more specifically, the three amino acid sequence of Gly Pro Gly.

Nucleic Acid Construction and Expression

Individual components of the fusion polypeptides of the invention may be produced from nucleic acids molecules using any suitable method known in the art. The nucleic acids encode fusion polypeptides which comprise one or more active or therapeutic agent(s). The nucleic acids encode targeting fusion polypeptides which comprise (i) a component that comprises a ligand or derivative or fragment thereof that binds a tissue-specific receptor, (ii) a component that comprises one or more agent(s) capable of providing a therapeutic effect or activating the target tissue, and optionally, (iii) a multimerizing component, wherein the multimerizing component multimerizes with a multimerizing component on another fusion polypeptide to form a multimeric tissue-specific fusion protein of the invention. The nucleic acid molecules can be inserted into a vector that is able to express the fusion polypeptides when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion polypeptides of the invention under control of transcriptional/translational control signals. These methods may include in vitro recombinant DNA and synthetic techniques and in vivo recombinations (See Sambrook et al. *Molecular Cloning, A Laboratory Manual*, Cold Spring Harbor Laboratory; Current Protocols in Molecular Biology, Eds. Ausubel, et al., Greene Publ. Assoc., Wiley-Interscience, NY).

Expression of the nucleic acid molecules of the invention may be regulated by a second nucleic acid sequence so that the molecule is expressed in a host transformed with the recombinant DNA molecule. For example, expression of the nucleic acid molecules of the invention may be controlled by any promoter/enhancer element known in the art. Promoters which may be used to control expression of the fusion polypeptide molecules include, but are not limited to, the long terminal repeat as described in Squinto et al. (1991) Cell 65:1-20; the SV40 early promoter region, the CMV promoter, the M-MuLV 5' terminal repeat the promoter contained in the 3' long terminal repeat of Rous sarcoma virus, the herpes thymidine kinase promoter, the regulatory sequences of the metallothionine gene; prokaryotic expression vectors such as the b-lactamase promoter, or the tac promoter (see also "Useful proteins from recombinant bacteria" in Scientific American (1980) 242:74-94); promoter elements from yeast or fungi such as the Gal 4 promoter, the ADH (alcohol dehydrogenase) promoter, PGK (phosphoglycerol kinase) promoter, alkaline phosphatase promoter, and tissue-specific transcriptional control regions derived from elastase I gene, insulin gene, immunoglobulin gene, mouse mammary tumor virus, albumin gene, α-fetoprotein gene, α1-antitrypsin gene, β-globin gene, myelin basic protein gene, myosin light chain-2 gene, and gonadotropic releasing hormone gene.

In accordance with the invention, the nucleic acid constructs may include components which are derived from immunoglobulins (antibodies). In general, such components will be derived from heavy ($V_H$) or light ($V_L$) chain variable regions. After identification and selection of antibodies exhibiting the desired binding characteristics, the variable regions of the heavy chains and/or light chains of each antibody is isolated, amplified, cloned and sequenced. Modifications may be made to the $V_H$ and $V_L$ nucleotide sequences, including additions of nucleotide sequences encoding amino acids and/or carrying restriction sites, deletions of nucleotide sequences encoding amino acids, or substitutions of nucleotide sequences encoding amino acids.

After identification of such ligands or portions thereof exhibiting desired characteristics, the nucleic acids that encode such domains are used in the nucleic acid constructs. Such nucleic acids may be modified, including additions of nucleotide sequences encoding amino acids and/or carrying restriction sites, deletions of nucleotide sequences encoding amino acids, or substitutions of nucleotide sequences encoding amino acids.

The nucleic acid constructs of the invention are inserted into an expression vector or viral vector by methods known to the art, wherein the nucleic acid molecule is operatively linked to an expression control sequence. Also provided is a host-vector system for the production of a tissue-specific fusion polypeptide of the invention, which comprises the expression vector of the invention, which has been introduced into a host cell suitable for expression of the fusion polypeptide. The suitable host cell may be a bacterial cell such as *E. coli*, a yeast cell, such as *Pichia pastoris*, an insect cell, such as *Spodoptera frugiperda*, or a mammalian cell, such as a COS, CHO, 293, BHK or NS0 cell.

The invention further encompasses methods for producing the fusion polypeptides of the invention by growing cells transformed with an expression vector under conditions permitting production of the tissue-specific fusion polypeptides and recovery of the fusion polypeptides so produced. Cells may also be transduced with a recombinant virus comprising the nucleic acid construct of the invention.

The fusion polypeptides may be purified by any technique, which allows for the subsequent formation of a stable polypeptide. For example, and not by way of limitation, the fusion polypeptides may be recovered from cells either as soluble polypeptides or as inclusion bodies, from which they may be extracted quantitatively by 8M guanidinium hydrochloride and dialysis. In order to further purify the fusion polypeptides, conventional ion exchange chromatography, hydrophobic interaction chromatography, reverse phase chromatography or gel filtration may be used. The fusion polypeptides may also be recovered from conditioned media following secretion from eukaryotic or prokaryotic cells.

In one embodiment of the invention, cells expressing a targeting fusion polypeptide of the invention are selected having a desired high production rate. A variety of selection processes known to the art may be used.

Screening and Detection Methods

The fusion polypeptides of the invention may also be used in in vitro or in vivo screening methods where it is desirable to detect and/or measure target protein levels or, for example, levels of receptor-bearing cells. Screening methods are well known to the art and include cell-free, cell-based, and animal assays. In vitro assays can be either solid state or soluble. Receptor detection may be achieved in a number of ways known to the art, including the use of a label or detectable group capable of identifying a tissue-specific polypeptide which is bound to a target cell. Detectable labels are well developed in the field of immunoassays and may generally be used in conjunction with assays using the tissue-specific fusion polypeptide of the invention.

A fusion polypeptide of the invention may also be directly or indirectly coupled to a label or detectable group when desirable for the purpose it is being used. A wide variety of labels may be used, depending on the sensitivity required, ease of conjugation, stability requirements, available instrumentation, and disposal provisions.

Therapeutic Methods

The invention herein further provides for the development of muscle-targeting fusion polypeptide described herein as a therapeutic for the treatment of patients suffering from disorders involving muscle cells or tissue which express any target muscle receptor. For example, a decrease in muscle mass, or atrophy, is associated with various physiological and pathological states. For example, muscle atrophy can result from denervation due to nerve trauma; degenerative, metabolic or inflammatory neuropathy, e.g. Guillian-Barré syndrome; peripheral neuropathy; or nerve damage caused by environmental toxins or drugs. Muscle atrophy may also result from denervation due to a motor neuropathy including, for example, adult motor neuron disease, such as Amyotrophic Lateral Sclerosis (ALS or Lou Gehrig's disease); infantile and juvenile spinal muscular atrophies; and autoimmune motor neuropathy with multifocal conductor block. Muscle atrophy may also result from chronic disease resulting from, for example, paralysis due to stroke or spinal cord injury; skeletal immobilization due to trauma, such as, for example, fracture, ligament or tendon injury, sprain or dislocation; or prolonged bed rest. Metabolic stress or nutritional insufficiency, which may also result in muscle atrophy, include the cachexia of cancer and other chronic illnesses including AIDS, fasting or rhabdomyolysis, and endocrine disorders such as disorders of the thyroid gland and diabetes. Muscle atrophy may also be due to a muscular dystrophy syndromes such as Duchenne, Becker, myotonic, fascioscapulohumeral, Emery-Dreifuss, oculopharyngeal, scapulohumeral, limb girdle, and congenital types, as well as the dystrophy known as Hereditary Distal Myopathy. Muscle atrophy may also be due to a congenital myopathy, such as benign congenital hypotonia, central core disease, nemalene myopathy, and myotubular (centronuclear) myopathy. Muscle atrophy also occurs during the aging process. Muscle atrophy in various pathological states is associated with enhanced proteolysis and decreased production of muscle proteins. Follistatin and related molecule FSTL1 and FLRG have been shown to block myostatin-a secreted protein that inhibits muscle growth. Myostatin-inhibitors have been suggested to be useful to increase muscle mass and to treat myopathy diseases (Bogdanovitch, et al. (2002) Nature 420:418-421.) Accordingly, a muscle-targeting fusion protein of the invention, wherein the active agent is follistatin, FSTL-1 or FLRG or a related myostatin-blocking molecule would be useful to increase muscle mass or to treat myopathy diseases. In addition, human myostatin propeptide, which also blocks myostatin, may be used to treat these diseases.

The ability of the targeting fusion proteins of the invention to exhibit a high degree of specificity for pre-selected target surface proteins makes them therapeutically useful for efficiently treating and/or activating a protein(s) at a desired pre-selected site. For example, the utility of IGF-1 for the treatment of a muscle-related condition, such as atrophy has, to date, been limited due to the presence of the IGF-1 receptor in non-muscle tissue. A muscle-specific fusion polypeptide of the invention wherein the ligand specific for a muscle surface protein is agrin or a MuSK binding fragment thereof, and the active and/or therapeutic agent is IGF-1 or fragment thereof has high degree of specificity for muscle tissue. IGF-1 has been used to treat humans suffering from growth hormone deficiencies, tissue wasting including burns, skeletal trauma, infection, cancer, cystic fibrosis, Duchenne muscular dystrophy, Becker dystrophy, autosomal recessive dystrophy, polymyositis, as well as myopathies and AIDS (U.S. Pat. No. 5,622,932).

Methods of Administration

Methods known in the art for the therapeutic delivery of agents such as proteins or nucleic acids can be used for the therapeutic delivery of a fusion polypeptide or a nucleic acid encoding a fusion polypeptide of the invention for treating and/or activating target tissue-specific surface proteins in a subject, e.g., cellular transfection, gene therapy, direct administration with a delivery vehicle or pharmaceutically acceptable carrier, indirect delivery by providing recombinant cells comprising a nucleic acid encoding a targeting fusion polypeptide of the invention.

Various delivery systems are known and can be used to administer the fusion polypeptide of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, pulmonary, intranasal, intraocular, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

In another embodiment, the active agent can be delivered in a vesicle, in particular a liposome (see Langer (1990) Science 249:1527-1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Aced. Sci. USA 88:1864-1868), etc. Alternatively, a nucleic acid can be introduced intracellularly and incorporated within host cell DNA for expression, by homologous recombination.

Cellular Transfection and Gene Therapy

The present invention encompasses the use of nucleic acids encoding the fusion polypeptides of the invention for transfection of cells in vitro and in vivo. These nucleic acids can be inserted into any of a number of well-known vectors for transfection of target cells and organisms. The nucleic acids are transfected into cells ex vivo and in vivo, through the interaction of the vector and the target cell. The compositions are administered (e.g., by injection into a muscle) to a subject in an amount sufficient to elicit a therapeutic response.

In another aspect, the invention provides a method of treating a target site, i.e., a target cell or tissue, in a human or other animal comprising transfecting a cell with a nucleic acid encoding a tissue-specific fusion polypeptide of the invention, wherein the nucleic acid comprises an inducible promoter operably linked to the nucleic acid encoding the targeting fusion polypeptide. For gene therapy procedures in the treatment or prevention of human disease, see for example, Van Brunt (1998) Biotechnology 6:1149-1154.

Combination Therapies

In numerous embodiments, the fusion polypeptides of the present invention may be administered in combination with one or more additional compounds or therapies. For example, multiple fusion polypeptides can be co-administered in conjunction with one or more therapeutic compounds. The combination therapy may encompass simultaneous or alternating administration. In addition, the combination may encompass acute or chronic administration.

Pharmaceutical Compositions

The present invention also provides pharmaceutical compositions comprising a fusion protein of the invention and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the tissue-specific fusion polypeptide of the invention which will be effective in the treatment of a tissue-related condition or disease can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 20-5000 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Kits

The invention also provides a pharmaceutical pack or kit comprising one or more containers filled with at least one targeting fusion polypeptide or nucleic acid encoding a fusion polypeptide of the invention. The kits of the invention may be used in any applicable method, including, for example, diagnostically. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Transgenic Animals

The invention includes transgenic non-human animals expressing a fusion polypeptide of the invention. A transgenic animal can be produced by introducing nucleic acid into the male pronuclei of a fertilized oocyte, e.g., by microinjection, retroviral infection, and allowing the oocyte to develop in a pseudopregnant female foster animal. Any of the regulatory or other sequences useful in expression vectors can form part of the transgenic sequence. A tissue-specific regulatory sequence(s) can be operably linked to the transgene to direct expression of the transgene to particular cells. A transgenic non-human animal expressing a tissue-specific fusion polypeptide of the invention is useful in a variety of applications, including as a means of producing such fusion proteins. Further, the transgene may be placed under the control of an inducible promoter such that expression of the tissue-specific fusion polypeptide may be controlled by, for example, administration of a small molecule.

Specific Embodiments

Example 1 illustrates embodiments of the fusion proteins of the invention targeted to skeletal muscle for the treatment of a deleterious skeletal muscle condition. More specifically described are muscle-specific fusion proteins comprising agrin and human insulin like growth factor 1 (hIGF-1) and variants thereof, as well as fusion polypeptides comprising agrin, hIGF1 and hIGF1 variants and human growth hormone (hGH) and fusion polypeptides comprising hIGF1 and variants thereof and hGH. Example 2 describes inventions which demonstrate the use of cadherins to produce the targeted fusion polypeptides of the invention. Example 3 described embodiments that demonstrate the use of follistatin and related molecules as the active or therapeutic agents in the fusion polypeptides of the invention. Example 4 describes embodiments of the fusion proteins of the invention that are active on endothelial cells. Example 5 describes myostatin-inhibiting fusion polypeptides of the invention.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Muscle Targeting Fusion Polypeptides

Exemplification of the fusion polypeptides of the invention include: human IGF-1 (r3long)-linker-50 Kd COOH terminal of human agrin 0.8 (SEQ ID NO:1); Processed form of human IGF-1 (r3long)-linker-50 Kd COOH terminal of human agrin 0.8 (without signal sequence) (SEQ ID NO:2); hIGF-1-linker-50 Kd COOH terminal of human agrin 0.8 (without signal sequence) (SEQ ID NO:3); processed form of hIGF-1-linker-50 Kd COOH terminal of human agrin 0.8 (without signal sequence) (SEQ ID NO:4); hIGF1 (r3long)-linker-50 Kd COOH terminal of human agrin 0.8 (SEQ ID NO:5); processed form of hIGF-1 (r3long)-linker-50 Kd COOH terminal of human agrin 0.8 (without signal sequence) (SEQ ID NO:6); hIGF1-linker-50 Kd COOH terminal of human agrin 0.0 (without signal sequence) (SEQ ID NO:7); processed form of hIGF-1-linker-50 Kd COOH terminal of human agrin 0.0 (without signal sequence) (SEQ ID NO:8); mature human IGF1 (del GPE, delR37)-Fc (SEQ ID NO:9); mature human IGF1 (del GPE, delR37) (SEQ ID NO:10); mature human IGF1 (del GPE, delR37) with GTG linker (SEQ ID NO:11); hGH-hIGF1-hAgrin 0.8 (SEQ ID NO:12); hGH-hIGF1-hFc (SEQ ID NO:13); hGH-hIGF1 with GTG linker (SEQ ID NO:14); hGH-hIGF2-hAgrin 0.8 (SEQ ID NO:15); hGH-hIGF2-hFc (SEQ ID NO:16); hGH-hIGF2 (SEQ ID NO:17); hGH-IGF1 (SEQ ID NO:18); hGH-hIGF1 (A37) (SEQ ID NO:19); hGH-hIGF1 (delete R37) (SEQ ID NO:20); hGHe-hIGF1 (mutated R3, A37) (SEQ ID NO:21); hGH-hIGF1 (mutated R3, delete R 37) (SEQ ID NO:22); hGH-hIGF1 (delete R37) (SEQ ID NO:23); hGH-hIGF1 (Del GPE) (SEQ ID NO:24); hGH-hIGF1 (Del GPE, del R37) (SEQ ID NO:25); hGH-hIGF1-human agrin 0.8 (SEQ ID NO:26); hGH-hIGF1 (del GPE)-human agrin 0.8 (SEQ ID NO:27); hGH-hIGF1 (del R37)-human agrin 0.8 (SEQ ID NO:28); hGH-hIGF1 (A37)-human agrin 0.8 (SEQ ID NO:29); hGH-hFc-hIGF1 (SEQ ID NO:30); hGH-hFc-hIGF1 (del R37) (SEQ ID NO:31); hGH-hFc-hIGF1 (del GPE) (SEQ ID NO:32); hGH-hFc-hIGF1 (del GPE, del R37) (SEQ ID NO:33). Further embodiments include the Tercera mutant form of IGF-1 linked to human agrin (0.8 or 0.0), and mutant forms of human IGF1 or IGF2 (such as set forth in SEQ ID NOS:10 or 11) used alone, linked to a multimerizing component (such as Fc; SEQ ID NO:9) or linked to human agrin.

The fusion protein constructs or molecules (1) human growth hormone-human IGF1; (2) human growth hormone-human IGF1-human Fc; (3) human growth hormone-human IGF1-human agrin 0.8; (4) human IGF1-Fc (A3, delR37); (5) human growth hormone and (6) human IGF1-agrin, were compared on C2C12 myotubes for their ability to activate various receptors and signaling pathways. The activity of IGF-1 was measured by its ability to phosphorylate the IGF-1 receptor and Akt kinase. The activity of human growth hormone (hGH) was measured by its ability to phosphorylate Stat5. The activity of agrin was measured by its ability to phosphorylate the MuSK receptor. Glass et al. (1996) 85:513-523; Beguinot et al. (1988) Biochemistry. 27(9):3222-8.

Phosphorylation assays indicated that fusion proteins having the configuration hGH-IGF1 which includes both hGH and hIGF1 is capable of simultaneously activating the IGF1 Receptor, Akt, and Stat5. Such phosphorylation was determined by a Western blot, using phospho-specific antibodies to the various molecules, or by immune-precipitating the receptors (such as IGFR), and Westerning with an antibody specific to anti-phospho-tyrosine. In addition, all of the above fusion polypeptides were made using human IGF1 mutants which had the first three amino acids deleted (Δ3) and either elimination or substitution of the arginines at positions 36 and/or 37. Such mutant IGF1 molecules demonstrated both resistance to cleavage as well as reduced binding by IGF-1 binding proteins (specifically IGF1 binding protein 5) without affecting signaling ability on C2C12 myotubes.

A fusion protein which includes hGH and hIGF1 and agrin simultaneously activates the IGF1 Receptor, Akt, Stat5, and the MuSK receptor, as determined by a Western blot, using phospho-specific antibodies to the various molecules, or by immune-precipitating the receptors (such as IGFR or MuSK), and Westerning with an antibody specific to anti-phospho-tyrosine. A fusion protein which includes IGF1 and agrin 0.8 activates the IGF1 receptor and binds and activates the MuSK receptor, thus providing muscle specificity. Constructs using agrin 0.0 were able to bind but not activate the MuSK receptor, thus demonstrating the use of this form of agrin for targeting muscle cells or tissue. Contacting C2C12 myotubes with the IGF1-GH fusion caused greater hypertrophy than IGF1 alone or GH alone.

Proliferin may be substituted for hGH in any of the above constructs (Wilder, E. L. et al. (1989) Mol. Cell Biol. 9(2): 430-441. Assessment of proliferin activity may include assays for neoangiogenesis (Jackson et al. Science (1994) 266:1581-1584. The human proliferin sequence is shown in SEQ ID NO:34.

Example 2

Muscle Targeting Fusion Polypeptides Using Cadherins

M-Cadherin containing fusion polypeptides for targeting muscle tissue were prepared using the following amino acid sequences: IGF1-muscle cadherin (SEQ ID NO:35) (containing 4 M-Cadherin domains)-IGF1; mature IGF1 (SEQ ID NO:36); full-length muscle cadherin (Cadherin 15) (SEQ ID NO:37); muscle cadherin extracellular domain containing 4 cadherin domains (SEQ ID NO:38); 4 muscle cadherin domains fused to SEAP (SEQ ID NO:39); 3 muscle cadherin domains (SEQ ID NO:40); 3 muscle cadherin domains fused to SEAP (SEQ ID NO:41); 2 muscle cadherin domains fused to SEAP (SEQ ID NO:42).

A fusion protein containing 4 N-terminal cadherin domains (SEQ ID NO:36) of human muscle cadherin (Cadherin 15) binds to skeletal muscle satellite cells. Secreted alkaline phosphatase (SeAP) was fused to the COOH terminus of a component containing 2 (SEQ ID NO:42), 3 (SEQ ID NO:41) or 4 (SEQ ID NO:39) cadherin domains of M-cadherin. Using antibodies to SEAP, it was determined that the fusion proteins containing either 3 or 4 N-terminal cadherin domains, but not the fusion protein containing 2 cadherin domains, bound C2C12 myoblast cells, but not fibroblasts, thus demonstrating their specificity for muscle cells.

In another embodiment, insulin-like growth factor 1 or a variant thereof (SEQ ID NOS:10 and 36) was fused to either four cadherin domains (SEQ ID NO:38) or 3 cadherin domains (SEQ ID NO:40) of M-cadherin to create muscle-specific polypeptides. In this case, C2C12 myotubes contacted with the fusion proteins hypertrophied, indicating that the IGF1 was active and that it bound to the C2C12 muscle cells. In an alternative embodiment, two IGF-1 molecules were fused to a polypeptide comprising 4 cadherin domains to create a muscle-specific fusion polypeptide (SEQ ID NO:35), which can also cause muscle hypertrophy.

Example 3

Muscle-Targeting Fusion Polypeptides Using Follistatin and Related Molecules The following protein sequences were also used to prepare muscle-specific fusion polypeptides that comprise the myostatin-inhibiting proteins follistatin (SEQ ID NO:43), FSTL1 (SEQ ID NO:44), and FLRG (also known as FSL3) (SEQ ID NO:45).

Follistatin, FSTLI and FLRG sequences (SEQ ID NOS: 43, 44 and 45) are fused to three or 4 N-terminal domains (SEQ ID NO:40 or 38) of M-cadherin. These fusion proteins all block myostatin-mediated phosphorylation of SMAD2, indicating that they are functional. Such fusion proteins can be used to block myostatin-mediated atrophy, or myostatin-mediated inhibition of differentiation, with the advantage of being muscle-specific.

Example 4

Vascular Endothelial Cell-Targeting Fusion Polypeptides

Fusion polypeptides comprising vascular endothelial (VE)-cadherin extracellular domains useful for targeting vascular tissue were prepared using the following amino acid sequences, as well as the human sequence set forth in Ludwig et al. (2000) supra. VE-cadherin Domain One (SEQ ID NO:46); VE-cadherin Domain Two (SEQ ID NO:47); VE-cadherin Domain Three (SEQ ID NO:48); VE-cadherin Domain Four (SEQ ID NO:49); and VE-cadherin Domain Five (SEQ ID NO:50).

Fusion proteins that comprise cadherin domains 1-5 (SEQ ID NOS 46-50), 1-4 (SEQ ID NOS:46-49), and 1-3 (SEQ ID NOS:46-48) of human VE cadherin (Cadherin 5), bind to vascular endothelial cells. When secreted alkaline phosphatase (SEAP) is fused to the COOH terminus of a component comprising four N-terminal domains of VE-cadherin (SEQ ID NOS:46-49), the protein binds endothelial cells but not fibroblasts.

In another embodiment of this example, vascular endothelial growth factor (VEGF) is fused to amino acids 18-583 of VE-Cadherin as described in Ludwig, D. et al. (2000) supra, which comprises SEQ ID NOS:46-49. In this case, endothelial cells demonstrate phosphorylation of the VEGF receptor, and activation of Akt, indicating that the VEGF receptor is bound and activated.

Example 5

Myostatin Inhibiting Fusion Polypeptide Constructs

The following fusion polypeptides were constructed to demonstrate the use of human myostatin propeptide in constructs which block myostatin activity: optional 23 amino acid signal sequence, human myostatin propeptide-human Fc1 (SEQ ID NO:51); optional 23 amino acid signal sequence, the active component is human myostatin propeptide, and the targeting component is human agrin (SEQ ID NO:520; optional SS of 23 amino acids, active agent is human myostatin propeptide, and targeting component is fragment of human agrin (SEQ ID NO:53); optional SS of 23 amino acids, active agent is human myostatin propeptide, and multimerizing component is human Fc protein (SEQ ID NO:54).

C2C12 myoblasts are grown to confluence and differentiated into myotubes. Differentiation is accomplished by switching to differentiation media—2% Horse Serum, in DMEM. Forty eight (48) to ninety six (96) hours post-differentiation, the myotubes are starved for four (4) hours, in serum-free media. For this experiment, plates of myotubes are treated in groups of two, for fifteen minutes, as follows: (a) untreated, (b) 100 ng/ml active myostatin, (c) a myostatin inhibitor of the instant invention (for example, the pre-pro domain of myostatin fused to an Fc, or the pre-pro domain of myostatin fused to agrin), at concentrations which could range from 10 ng/ml to 10 ug/ml (d) active myostatin plus a myostatin inhibitor of the instant invention. After treatment, the myotubes are lysed, for example, in NP40 lysis buffer containing phosphatase and protease inhibitors. The resulting lysates are then processed for Western blot analysis with an antibody specific for phosphorylated Smad2, and, as a control for total protein levels, a second Western was performed using an antibody which recognizes nonphosphorylated Smad2. The assay demonstrates that myostatin (GDF8) induces SMAD 2 phosphorylation and that the myostatin inhibitors described above block myostatin-mediated phosphorylation of Smad2.

We claim:

1. A method of treating a muscle atrophy or muscle dystrophy, comprising administering to a subject in need thereof a modified human insulin-like growth factor-1 (IGF-1) fusion polypeptide comprising a modified human IGF-1 in which amino acids 1-3 and 37 relative to mature human IGF-1 are deleted, and a multimerizing component capable of forming a multimer with another said modified IGF-1 fusion polypeptide, wherein the multimerizing component is an Fc domain from IgG1, IgG2, IgG3, or IgG4.

2. The method of claim 1, wherein the fusion polypeptide comprises the amino acid sequence of SEQ ID NO:9.

* * * * *